US012660788B2

(12) United States Patent
Ishikawa et al.

(10) Patent No.: US 12,660,788 B2
(45) Date of Patent: Jun. 23, 2026

(54) TOBAMOVIRUS-RESISTANT TOMATO PLANT, METHOD FOR PRODUCING TOBAMOVIRUS-RESISTANT TOMATO PLANT, METHOD FOR IMPARTING TOBAMOVIRUS RESISTANCE IN TOMATO PLANT, METHOD FOR SCREENING FOR TOBAMOVIRUS-RESISTANT TOMATO PLANT, AND METHOD FOR DETECTING TOBAMOVIRUS RESISTANCE IN TOMATO PLANT

(71) Applicants: National Agriculture and Food Research Organization, Ibaraki (JP); Takii & Company Limited, Kyoto (JP)

(72) Inventors: Masayuki Ishikawa, Tsukuba (JP); Kazuhiro Ishibashi, Tsukuba (JP); Akihito Kano, Kyoto (JP)

(73) Assignees: National Agriculture and Food Research Organization, Ibaraki (JP); Takii & Company Limited, Kyoto (JP)

( * ) Notice: Subject to any disclaimer, the term of this patent is extended or adjusted under 35 U.S.C. 154(b) by 464 days.

(21) Appl. No.: 17/799,398

(22) PCT Filed: Nov. 25, 2020

(86) PCT No.: PCT/JP2020/043863
§ 371 (c)(1),
(2) Date: Aug. 12, 2022

(87) PCT Pub. No.: WO2021/161615
PCT Pub. Date: Aug. 19, 2021

(65) Prior Publication Data
US 2023/0337621 A1 Oct. 26, 2023

(30) Foreign Application Priority Data

Feb. 12, 2020 (JP) ................................. 2020-021960
May 19, 2020 (JP) ................................. 2020-087665

(51) Int. Cl.
| | |
|---|---|
| *A01H 6/82* | (2018.01) |
| *A01H 1/00* | (2006.01) |
| *A01H 5/08* | (2018.01) |
| *C07K 14/415* | (2006.01) |

(52) U.S. Cl.
CPC ............. *A01H 6/825* (2018.05); *A01H 1/126* (2021.01); *A01H 5/08* (2013.01); *C07K 14/415* (2013.01)

(58) Field of Classification Search
None
See application file for complete search history.

(56) References Cited

U.S. PATENT DOCUMENTS

2020/0077614 A1* 3/2020 Ashkenazi ........... C07K 14/415

FOREIGN PATENT DOCUMENTS

| CN | 1721435 A | * | 1/2006 |
|---|---|---|---|
| JP | 2004254658 A | * | 9/2004 |

OTHER PUBLICATIONS

Wells, James A. "Additivity of mutational effects in proteins." Biochemistry 29.37 (1990): 8509-8517. (Year: 1990).*
Ngo, J. Thomas, Joe Marks, and Martin Karplus. "Computational complexity, protein structure prediction, and the Levinthal paradox." The protein folding problem and tertiary structure prediction. Boston, MA: Birkhäuser Boston, 1994. 433-506. (Year: 1994).*
Ng, Pauline C., and Steven Henikoff. "Predicting deleterious amino acid substitutions." Genome research 11.5 (2001): 863-874. (Year: 2001).*
Keskin, Ozlem, et al. "A new, structurally nonredundant, diverse data set of protein-protein interfaces and its implications." Protein Science 13.4 (2004): 1043-1055. (Year: 2004).*
Thornton, Janet M., et al. "From structure to function: approaches and limitations." nature structural biology 7.11 (2000): 991-994. (Year: 2000).*
Travella, Silvia, Theres E. Klimm, and Beat Keller. "RNA interference-based gene silencing as an efficient tool for functional genomics in hexaploid bread wheat." Plant physiology 142.1 (2006): 6-20. (Year: 2006).*
Nagai, Alice, et al. "Tomato mottle mosaic virus in Brazil and its relationship with Tm-2 2 gene." European Journal of Plant Pathology 155 (2019): 353-359. (Year: 2019).*
Li, Yueyue, et al. "The complete genome sequence, occurrence and host range of Tomato mottle mosaic virus Chinese isolate." Virology journal 14 (2017): 1-9. (Year: 2017).*
Sánchez-Sánchez, Mario, et al. "Understanding tobamovirus-plant interactions: implications for breeding resistance to tomato brown rugose fruit virus." Journal of Plant Pathology 105.1 (2023): 83-94. (Year: 2023).*
Ali, Md Emran, et al. "Conferring virus resistance in tomato by independent RNA silencing of three tomato homologs of *Arabidopsis* TOM1." Archives of virology 163 (2018): 1357-1362. (Year: 2018).*

(Continued)

*Primary Examiner* — Amjad Abraham
*Assistant Examiner* — Kelsey L Mcwilliams
(74) *Attorney, Agent, or Firm* — Morgan, Lewis & Bockius LLP

(57) ABSTRACT

The present invention provides a tomato plant which is resistant to ToBRFV. A *Tobamovirus* resistant tomato plant of the present invention is with loss of function for a SlTOM1a gene, a SlTOM1c gene, and a SlTOM1d gene.

12 Claims, 6 Drawing Sheets
Specification includes a Sequence Listing.

(56)     References Cited

OTHER PUBLICATIONS

Ishibashi, Kazuhiro, and Masayuki Ishikawa. "Replication of tobamovirus RNA." Annual Review of Phytopathology 54.1 (2016): 55-78. (Year: 2016).*

Doerks, Tobias, Amos Bairoch, and Peer Bork. "Protein annotation: detective work for function prediction." Trends in Genetics 14.6 (1998): 248-250 (Year: 1998).*

Smith, Temple F., and Xiaolin Zhang. "The challenges of genome sequence annotation or "the devil is in the details"." Nature biotechnology 15.12 (1997): 1222-1223. (Year: 1997).*

Bork, Peer, and Amos Bairoch. "Go hunting in sequence databases but watch out for the traps." Trends in Genetics 12.10 (1996): 425-427. (Year: 1996).*

Gutterson, Neal. "Anthocyanin biosynthetic genes and their application to flower color modification through sense suppression." HortScience 30.5 (1995): 964-966. (Year: 1995).*

Bruening, George. "Plant gene silencing regularized." Proceedings of the National Academy of Sciences 95.23 (1998): 13349-13351. (Year: 1998).*

Elomaa, Paula, et al. "Transformation of antisense constructs of the chalcone synthase gene superfamily into Gerbera hybrida: differential effect on the expression of family members." Molecular Breeding 2 (1996): 41-50. (Year: 1996).*

Colliver, S. P., P. Morris, and M. P. Robbins. "Differential modification of flavonoid and isoflavonoid biosynthesis with an antisense chalcone synthase construct in transgenic Lotus corniculatus." Plant Molecular Biology 35 (1997): 509-522. (Year: 1997).*

Emery, John F., et al. "Radial patterning of *Arabidopsis* shoots by class III HD-ZIP and KANADI genes." Current Biology 13.20 (2003): 1768-1774. (Year: 2003).*

Nunes, Aline CS, et al. "RNAi-mediated silencing of the myo-inositol-1-phosphate synthase gene (GmMIPS1) in transgenic soybean inhibited seed development and reduced phytate content." Planta 224 (2006): 125-132. (Year: 2006).*

Arziman, Zeynep, Thomas Horn, and Michael Boutros. "E-RNAi: a web application to design optimized RNAi constructs." Nucleic acids research 33.suppl_2 (2005): W582-W588. (Year: 2005).*

English Translation of CN 1721435 A, published Jan. 18, 2006) (Year: 2006).*

Demorest, Zachary L., et al. "Direct stacking of sequence-specific nuclease-induced mutations to produce high oleic and low linolenic soybean oil." BMC plant biology 16 (2016): 1-8 (Year: 2016).*

Extended European Search Report issued in the corresponding European Application No. 20918690.7, dated Feb. 21, 2024.

Ishikawa et al., "Tomato brown rugose fruit virus resistance generated by quadruple knockout of homologs of Tobamovirus Multiplication1 in tomato", 2022, Plant Physiol., 189:679-686.

Salem et al., "A new tobamovirus infecting tomato crops in Jordan," Archives of Virology, 161: 503-506 (2016).

Luria et al., "A New Israeli Tobamovirus Isolate Infects Tomato Plants Harboring Tm-22 Resistance Genes," PLOS One, 12 (1): e0170429 (2017).

Fauser et al., "Both CRISPR/Cas-based nucleases and nickases can be used efficiently for genome engineering in *Arabidopsis thaliana*," The Plant Journal, 79: 348-359 (2014).

Lei et al., "CRISPR-P: A Web Tool for Synthetic Single-Guide RNA Design of CRISPR-System in Plants," Molecular Plant, 7: 1494-1496 (2014).

Sun et al., "A Highly Efficient Transformation Protocol for Micro-Tom, a Model Cultivar for Tomato Functional Genomics," Plant Cell Physiology, 47 (3): 426-431 (2006).

Konieczny et al., "A procedure for mapping Arabidopsis mutations using co-dominant ecotype-specific PCR-based markers," The Plant Journal, 4 (2): 403-410 (1993).

Vouillot et al., "Comparison of T7E1 and Surveyor Mismatch Cleavage Assays to Detect Mutations Triggered by Engineered Nucleases," Genes, 5 (3): 407-415 (2015).

Neff et al., "dCAPS, a simple technique for the genetic analysis of single nucleotide polymorphisms: experimental applications in *Arabidopsis thaliana* genetics," The Plant Journal, 14 (3): 387-392 (1998).

Ohno et al., "Nucleotide Sequence of the Tobacco Mosaic Virus (Tomato Strain) Genome and Comparison with the Common Strain Genome," The Journal of Biochemistry, 96 (6): 1915-1923 (1984).

Ali et al., "Conferring virus resistance in tomato by independent RNA silencing of three tomato homologs of *Arabidopsis* TOM1," Archives of Virology, 163: 1357-1362 (2018).

Fujisaki et al., "Analysis of tobamovirus multiplication in *Arabidopsis thaliana* mutants defective in TOM2A homologues," Journal of General Virology, 89: 1519-1524 (2008).

Sato et al., "Selective involvement of members of the eukaryotic initiation factor 4E family in the infection of *Arabidopsis thaliana* by potyviruses", FEBS Letters, 579: 1167-1171 (2005).

International Search Report issued in corresponding International Patent Application No. PCT/JP2020/043863 dated Dec. 22, 2020.

NCBI Reference Sequence, "tobamovirus multiplication protein 3 [Solanum lycopersicum]", GenPept, Accession No. XP_010315372, Aug. 8, 2018, 2 pages.

* cited by examiner day24 day39 day70 day79 day79

```
                        SEQUENCE LISTING

<160> NUMBER OF SEQ ID NOS: 26

<210> SEQ ID NO 1
<211> LENGTH: 1324
<212> TYPE: DNA
<213> ORGANISM: Solanum lycopersicum

<400> SEQUENCE: 1
taatagtcaa aaagaataaa tcctagaacg ttcagggaac gccgctgtgt ttctctcctt      60
tctcgccggc cgttttaggc tcaataattt tctgatcaaa caaaaaattc tctaaaattt     120
catttatttc gtattttttg gtgtgtctaa tttcggatct ccggcgatgg gtcgggttga     180
aacagcggtg gacccgtcgt cgacggctgc ggtggcggcg taccgtttac atgaggcaat     240
aagctggtgg gatgaagtga atgaatctcc tatttggcaa gaccgtattt tctatgtcct     300
tgcgatctta tacggcgtcg tttctgctgt tgctcttgtg caattaatcc ggattcagat     360
gagagttccc gagtatggat ggaccactca gaaagtcttc catttcctca atttcttggt     420
gaatggggtt cgctctctgg tttttgtatt tcgtcgggat gttcagaagt tgaaccctga     480
gattatccaa cacatcttgc ttgatatgcc aagtcttgca ttcttcacaa cttttgcgct     540
tctagtattg ttctgggctg agatatacta tcaggcacgt gctgtatcta ctgatgctct     600
taggcctagt ttcttcacaa tcaatggagt tgtttatgct attcagatta ttttatggct     660
```

-continued

```
gataatatgg tggaagcctg ttccagtact cgtcatctta tcgaaggcat tctttgcagg       720
tgtatctcta tttgcagcct tggggtttct tctttatgga ggaaggcttt tccttatgtt       780
acggcgtttc cctgtagaat caagggggag acagaagaaa cttcaggaag ttggttatgt       840
gacaacaata tgttttttcat gcttcctgat tagatgcatt atgatgtgtt tcaatgcatt      900
tgataaagct gcggatcttg atgttttata tcatccaatg ttaaattttg tatactatct       960
gttggtagag attctacctt cttcacttgt ccttttcatt ttgaggaagt tgcctccaaa      1020
gcgagggatc acgcagtacc accctattcg ctgatacaac agcgtgcatc ggatgatgaa      1080
atcaagcgct gggatcaggt tatcagatga gttggctttt acgatactcg tcctacccat      1140
atagtgagat actgtacatg gagcatggtt catcaggact ctggaaaaat agtttgttct      1200
ctgcagatat tagttgtgtc tgtaatttgt ttgtagtctt gatacaagag ttgtggaaga      1260
agttgtgtta tttctagtgt aattatcttc atatttgtat gtttgagatt tcaattgatt      1320
attc                                                                    1324
```

<210> SEQ ID NO 2
<211> LENGTH: 1353
<212> TYPE: DNA
<213> ORGANISM: Solanum lycopersicum

<400> SEQUENCE: 2

```
gaaaaagaat aaatcctaga acgttcaggg aacgccgctg tgtttctctc ctttctcgcc        60
ggccgtttta ggctcaataa ttttctgatc aaacaaaaaa ttctctaaaa tttcatttat       120
ttcgtatttt ttggtgtgtc taatttcgga tctccggcga tgggtcgggt tgaaacagcg       180
gtggacccgt cgtcgacggc tgcggtggcg gcgtaccgtt tacatgaggc aataagctgg       240
tgggatgaag tgaatgaatc tcctatttgg caagaccgta ttttctatgt ccttgcgatc       300
ttatacggcg tcgtttctgc tgttgctctt gtgcaattaa tccggattca gatgagagtt       360
cccgagtatg gatggaccac tcagaaagtc ttccatttcc tcaatttctt ggtgaatggg       420
gttcgctctc tggttttttgt atttcgtcgg gatgttcaga agttgaaccc tgagattatc       480
caacacatct tgcttgatat gccaagtctt gcattcttca caacttttgc gcttctagta       540
ttgttctggg ctgagatata ctatcaggca cgtgctgtat ctactgatgc tcttaggcct       600
agtttcttca caatcaatgg agttgtttat gctattcaga ttattttatg ctgataata       660 tggtggaagc ctgttccagt actcgtcatc ttatcgaagg cattctttgc aggtgtatct       720
ctatttgcag cctggggtt tcttctttat ggaggaaggc ttttccttat gttacggcgt       780
ttccctgtag aatcaagggg gagacagaag aaacttcagg aagttggtta tgtgacaaca       840
atatgttttt catgcttcct gattagatgc attatgatgt gtttcaatgc atttgataaa       900
gctgcggatc ttgatgtttt atatcatcca atgttaaatt ttgtatacta tctgttggta       960
gagattctac cttcttcact tgtcctttttc attttgagga agttgcctcc aaagcgaggg      1020
atcacgcagt accaccctat tcgctgatac aacagcgtgc atcggatgat gaaatcaaag      1080
cgctgggatc aggttatcag atgagttggc ttttacgata ctcgtcctac ccatatagtg      1140
agatactgta catggagcat ggttcatcag gactctggaa aaatagtttg ttctctgcag      1200
atattagttg tgtctgtaat ttgtttgtag tcttgataca agagttgtgg aagaagttgt      1260
gttatttcta gtgtaattat cttcatattt gtatgtttga gatttcaatt gattattctt      1320
ttcccccaaa aaaaaaaaaa aaatcctgcg gca                                    1353
```

<210> SEQ ID NO 3
<211> LENGTH: 295
<212> TYPE: PRT
<213> ORGANISM: Solanum lycopersicum

<400> SEQUENCE: 3

```
Met Gly Arg Val Glu Thr Ala Val Asp Pro Ser Ser Thr Ala Ala Val
1               5                   10                  15

Ala Ala Tyr Arg Leu His Glu Ala Ile Ser Trp Trp Asp Glu Val Asn
            20                  25                  30

Glu Ser Pro Ile Trp Gln Asp Arg Ile Phe Tyr Val Leu Ala Ile Leu
        35                  40                  45

Tyr Gly Val Val Ser Ala Val Ala Leu Val Gln Leu Ile Arg Ile Gln
    50                  55                  60

Met Arg Val Pro Glu Tyr Gly Trp Thr Thr Gln Lys Val Phe His Phe
65                  70                  75                  80

Leu Asn Phe Leu Val Asn Gly Val Arg Ser Leu Val Phe Val Phe Arg
                85                  90                  95

Arg Asp Val Gln Lys Leu Asn Pro Glu Ile Ile Gln His Ile Leu Leu
            100                 105                 110

Asp Met Pro Ser Leu Ala Phe Phe Thr Thr Phe Ala Leu Leu Val Leu
            115                 120                 125

Phe Trp Ala Glu Ile Tyr Tyr Gln Ala Arg Ala Val Ser Thr Asp Ala
        130                 135                 140

Leu Arg Pro Ser Phe Phe Thr Ile Asn Gly Val Val Tyr Ala Ile Gln
145                 150                 155                 160

Ile Ile Leu Trp Leu Ile Ile Trp Trp Lys Pro Val Pro Val Leu Val
                165                 170                 175

Ile Leu Ser Lys Ala Phe Phe Ala Gly Val Ser Leu Phe Ala Ala Leu
            180                 185                 190

Gly Phe Leu Leu Tyr Gly Gly Arg Leu Phe Leu Met Leu Arg Arg Phe
            195                 200                 205

Pro Val Glu Ser Arg Gly Arg Gln Lys Lys Leu Gln Glu Val Gly Tyr
    210                 215                 220

Val Thr Thr Ile Cys Phe Ser Cys Phe Leu Ile Arg Cys Ile Met Met
225                 230                 235                 240

Cys Phe Asn Ala Phe Asp Lys Ala Ala Asp Leu Asp Val Leu Tyr His
            245                 250                 255

Pro Met Leu Asn Phe Val Tyr Tyr Leu Leu Val Glu Ile Leu Pro Ser
            260                 265                 270

Ser Leu Val Leu Phe Ile Leu Arg Lys Leu Pro Pro Lys Arg Gly Ile
        275                 280                 285

Thr Gln Tyr His Pro Ile Arg
    290                 295
```

<210> SEQ ID NO 4
<211> LENGTH: 1306
<212> TYPE: DNA
<213> ORGANISM: Solanum lycopersicum

<400> SEQUENCE: 4

```
tacatttgtc ctccttcccc cttcatccac gtgtggttcc tccaaaccct ccaccccact      60
cttcactcta tttgatttga acgaacatcc ccatcacttc actctctaca ttttttcttca    120 tctgtaaatc accattttg ttagacgtag tagctatggt aaaatctata agctttcttc     180
```

-continued

```
ttgaattcgc aaaagattac gatgatggaa caccacgagt tcgccccatc tttgattggt       240
tcaatgcgat gatggaggtc tccgattatg agaaacaagc catcttttat tctctctctg       300
ccgcctatgc cttagtctca tttgttgcac tggtacaact catccgcatc caattgcgcc       360
tttcaggaat tggttggaca acacaaaagg tttttcactt gatgaatttt gttgtctgtg       420
gattgagagc aatattattt gggttctaca gcagcgtgtt caatcttaga tcaaaagcac       480
ttgagatgat gcttctggat ctccccggtc ttctattctt ctccacatac acactattag       540
ttctgttttg ggctgaaata ttccatcagg caagaaacct tccaatcgat aaacttcgac       600
ctgcatatta tgcagttaat gcagtcgtat attttataca gatatgcata tggatcttca       660
tcggtgttgg cccagcttcg gctgctgttg aaactgctaa actttttttc gcagttattt       720
catttactgc tgctctggga tttgttatgt atggtggaag gttgttcgct atgcttcggc       780
gcttccctat tgaatctaga ggccgtcaaa agaagcttca tgaggttggt ttcgtgactg       840
gtatttgctg catttgtttc atgatcagat gtgttatggt tgctgtttct gcttttaacg       900
ggaacgctga tgttgatgtc attgaccatc cagttctcat tctcttctat tacgtggtgg       960
tggagatctt gccttctgtt ttggtgcttt ttattctgcg caaattacct ccaaaacgtg       1020
tatcagagca atatcatcct atccaataac tcatagaaga gcatccctga ttttagtact      1080
tcaccgtttt tgttcaaaga agcccttgtc atgccagcca agtttttagt tcttataata      1140
tcatttttgc ttttattgtt ttggcgcttg tctcgagtga cgtggaggag ttatagtttg      1200
atttcagtac agctctgtag aagtcttgaa ttataaatta ttcaaagtgc atgtgacttg      1260
taatcatttg gatagaatta gatgttcgaa gtttaaaggc cttggg                      1306
```

```
<210> SEQ ID NO 5
<211> LENGTH: 1316
<212> TYPE: DNA
<213> ORGANISM: Solanum lycopersicum

<400> SEQUENCE: 5
```

```
gacatttgtc ctccttcccc cctcatccac gtgtggttcc tccaaaccct ccaccccact        60
cttcactcta tttgatttga acgaacatcc ccatcacttc actctctaca ttttttcttca      120 tctgtaaatc accatttttg ttagacgtag tagctatggt aaaatctata agctttcttc      180
ttgaattcgc aaaagattac gatgatggaa caccacgagt tcgccccatc tttgattggt       240
tcaatgcgat gatggaggtc tccgattatg agaaacaagc catcttttat tctctctctg       300
ccgcctatgc cttagtctca tttgttgcac tggtacaact catccgcatc caattgcgcc       360
tttcaggaat tggttggaca acacaaaagg tttttcactt gatgaatttt gttgtctgtg       420
gattgagagc aatattattt gggttctaca gcagcgtgtt caatcttaga tcaaaagcac       480
ttgagatgat gcttctggat ctccccggtc ttctattctt ctccacatac acactattag       540
ttctgttttg ggctgaaata ttccatcagg caagaaacct tccaatcgat aaacttcgac       600
ctgcatatta tgcagtcaat gcagtcgtat attttataca gatatgcata tggatcttca       660
tcggtgttgg cccagcttcg gctgctgttg aaactgctaa actttttttc gcagttattt       720
catttactgc tgctctggga tttgttatgt atggtggaag gttgttcgct atgcttcggc       780
gcttccctat tgaatctaga ggccgtcaaa agaagcttca tgaggttggt ttcgtgactg       840
gtatttgctg catttgtttc atgatcagat gtgttatggt tgctgtttct gcttttaacg       900
ggaacgctga tgttgatgtc attgaccatc cagttctcat tctcttctat tacgtggtgg       960
tggagatctt gccttctgtt ttggtgcttt ttattctgcg caaattacct ccaaaacgtg       1020
```

-continued

```
tatcagagca atatcatcct atccaataac tcatagaaga gcatccctga ttttagtact   1080
tcaccgtttt tgttcaaaga agcccttgtc atgccagcca agtttttagt tcttataata   1140
tcatttttgc ttttattgtc ttgacgcttg tctcgagtga cgtggaggag ttatagtttg   1200
atttcagtac agctctgtag aagtcttgaa ttataaatta ttcaaagtgc atgtgacttg   1260
taatcatttg gatagaatta gatgttcgaa gtttaaaggc cttgggttat attgtg       1316
```

<210> SEQ ID NO 6
<211> LENGTH: 297
<212> TYPE: PRT
<213> ORGANISM: Solanum lycopersicum

<400> SEQUENCE: 6

```
Met Val Lys Ser Ile Ser Phe Leu Leu Glu Phe Ala Lys Asp Tyr Asp
1               5                   10                  15

Asp Gly Thr Pro Arg Val Arg Pro Ile Phe Asp Trp Phe Asn Ala Met
                20                  25                  30

Met Glu Val Ser Asp Tyr Glu Lys Gln Ala Ile Phe Tyr Ser Leu Ser
            35                  40                  45

Ala Ala Tyr Ala Leu Val Ser Phe Val Ala Leu Val Gln Leu Ile Arg
        50                  55                  60

Ile Gln Leu Arg Leu Ser Gly Ile Gly Trp Thr Thr Gln Lys Val Phe
65                  70                  75                  80

His Leu Met Asn Phe Val Val Cys Gly Leu Arg Ala Ile Leu Phe Gly
                85                  90                  95

Phe Tyr Ser Ser Val Phe Asn Leu Arg Ser Lys Ala Leu Glu Met Met
            100                 105                 110

Leu Leu Asp Leu Pro Gly Leu Leu Phe Phe Ser Thr Tyr Thr Leu Leu
        115                 120                 125

Val Leu Phe Trp Ala Glu Ile Phe His Gln Ala Arg Asn Leu Pro Ile
    130                 135                 140

Asp Lys Leu Arg Pro Ala Tyr Tyr Ala Val Asn Ala Val Val Tyr Phe
145                 150                 155                 160

Ile Gln Ile Cys Ile Trp Ile Phe Ile Gly Val Gly Pro Ala Ser Ala
                165                 170                 175

Ala Val Glu Thr Ala Lys Leu Phe Phe Ala Val Ile Ser Phe Thr Ala
            180                 185                 190

Ala Leu Gly Phe Val Met Tyr Gly Gly Arg Leu Phe Ala Met Leu Arg
        195                 200                 205

Arg Phe Pro Ile Glu Ser Arg Gly Arg Gln Lys Lys Leu His Glu Val
    210                 215                 220

Gly Phe Val Thr Gly Ile Cys Cys Ile Cys Phe Met Ile Arg Cys Val
225                 230                 235                 240

Met Val Ala Val Ser Ala Phe Asn Gly Asn Ala Asp Val Asp Val Ile
                245                 250                 255

Asp His Pro Val Leu Ile Leu Phe Tyr Tyr Val Val Val Glu Ile Leu
            260                 265                 270

Pro Ser Val Leu Val Leu Phe Ile Leu Arg Lys Leu Pro Pro Lys Arg
        275                 280                 285

Val Ser Glu Gln Tyr His Pro Ile Gln
    290                 295
```

<210> SEQ ID NO 7
<211> LENGTH: 1344

-continued

```
<212> TYPE: DNA
<213> ORGANISM: Solanum lycopersicum

<400> SEQUENCE: 7
tgctaatgaa cttgaatact tacagttatc ttaattgttt gtattaggaa gcatcagttt      60
tttgacttct ttcaatacaa caagataagc ggaggggaga gctgaaatgg ctaggttgcc     120
acttgggtcg tcgccgattg acatcgccgg tccggtgacc aactggtggg accacgtcaa     180
cgaatccgtt cagtggcaag atgggatttt ctactccctt tgtgcttcct atggtcttgt     240
ttcagcagtt gccctaattc aattaatacg aattgatttg agggtacccg agtatggctg     300
gacaacacaa aaggtgttcc atctgatgaa cttttgttgta aatggagttc gtgcaattgt     360
ctttggattt cacaaacatg ttttttctgct ccattataag gtgctgactc tggcaatatt     420
ggacctacca gggctccttt tcttttcaac attcacactc cttgttctat tttgggctga     480
gatatatcac caggctagga gtttaccaac agataagctc aggatttctt atattgccat     540
taatgatgcc atatacttca ttcaggcctg tatctgggtt tacctctgga tcaatgacaa     600
tagcacagtg gaattcattg ggaagatatt tatggcagtt gtatcagtta ttgcagcctt     660
gggctttctg ctatatggtg gaaggttatt tctcatgctg cggcgcttcc ctattgaatc     720
taaagggagg agaaagaagc ttcatgaggt tggatcggtg actgccatat gtttcacctg     780
tttcctcatt agatgctttg tggttgtgtt atctgctttt gattctgacg catctcttga     840
cgtcttggat catcctgttt tgaatctgat atactacctg ctggtagaaa ttcttccttc     900
agctcttgtg ctgtacatcc tgcgaaaact gcctccaaaa agagtgtctc cacaatacca     960
cccaatcagt tagctgcagc agaattttat cgttagtgat acacgttccc atggtttctg    1020
ttgcagaagc taactggagt tgttcaggaa aagtgaaact gcaaaaggat attcggttgc    1080
aataattctg cggaaaggca agattcaac gcttttttgg cagttgttaa aacagaggtt    1140
aagctgtttt gcttacatta tattgtttct gtggtttttag tgtgaagcat gagacaaata    1200
agtgttcccc acgtctgtga aaaatcctag tcatgatgta atgacgcaga gggtaaatct    1260
cagtatcgcc attgtactgg catgttgtaa ctatgatgtt ctggatctcc tttactgcaa    1320
tgactgatgt cctttgtttg gtca                                          1344

<210> SEQ ID NO 8
<211> LENGTH: 1278
<212> TYPE: DNA
<213> ORGANISM: Solanum lycopersicum

<400> SEQUENCE: 8
acaacaagat aagcggaggg gagagctgaa atggctaggt tgccacttgg gtcgtcgccg      60
attgacatcg ccggtccggt gaccaactgg tgggaccacg tcaacgaatc cgttcagtgg     120
caagatggga ttttctactc cctttgtgct tcctatggtc ttgtttcagc agttgcccta     180
attcaattaa tacgaattga tttgagggta cccgagtatg gctggacaac acaaaaggtg     240
ttccatctga tgaactttgt tgtaaatgga gttcgtgcaa ttgtctttgg atttcacaaa     300 catgttttttc tgctccatta taaggtgctg actctggcaa tattggacct accagggctc     360
ctttttcttt caacattcac actccttgtt ctattttggg ctgagatata tcaccaggct     420
aggagtttac caacagataa gctcaggatt tcttatattg ccattaatga tgccatatac     480
ttcattcagg cctgtatctg ggtttacctc tggatcaatg acaatagcac agtggaattc     540
attgggaaga tatttatggc agttgtatca gttattgcag ccttgggctt tctgctatat     600
```

-continued

```
ggtggaaggt tatttctcat gctgcggcgc ttccctattg aatctaaagg gaggagaaag      660
aagcttcatg aggttggatc ggtgactgcc atatgtttca cctgtttcct cattagatgc      720
tttgtggttg tgttatctgc ttttgattct gacgcatctc ttgacgtctt ggatcatcct      780
gttttgaatc tgatatacta cctgctggta gaaattcttc cttcagctct tgtgctgtac      840
atcctgcgaa aactgcctcc aaaaagagtg tctgcacaat accacccaat cagttagctg      900
cagcagaatt ttatcgttag tgatacacgt tcccatggtt tctgttgcag aagctaactg      960
gagttgttca ggaaaagtga aactgcaaaa ggatattcgg ttgcaataat tctgcggaaa     1020
ggcaaagatt caacgctttt ttggcagttg ttaaaacaga ggttaagctg ttttgcttac     1080
attatattgt ttctgtggtt ttagtgtgaa gcatgagaca aataagtgtt ccccacgtct     1140
gtgaaaaatc ctagtcatga tgtaatgacg cagagggtaa atctcagtat cgccattgta     1200
ctggcatgtt gtaactatga tgttctggat ctcctttact gcaatgactg atgtcctttg     1260
tttggtcaaa aaaaaaaa                                                    1278
```

<210> SEQ ID NO 9
<211> LENGTH: 288
<212> TYPE: PRT
<213> ORGANISM: Solanum lycopersicum

<400> SEQUENCE: 9

```
Met Ala Arg Leu Pro Leu Gly Ser Ser Pro Ile Asp Ile Ala Gly Pro
1               5                   10                  15

Val Thr Asn Trp Trp Asp His Val Asn Glu Ser Val Gln Trp Gln Asp
                20                  25                  30

Gly Ile Phe Tyr Ser Leu Cys Ala Ser Tyr Gly Leu Val Ser Ala Val
                35                  40                  45

Ala Leu Ile Gln Leu Ile Arg Ile Asp Leu Arg Val Pro Glu Tyr Gly
            50                  55                  60

Trp Thr Thr Gln Lys Val Phe His Leu Met Asn Phe Val Val Asn Gly
65                  70                  75                  80

Val Arg Ala Ile Val Phe Gly Phe His Lys His Val Phe Leu Leu His
                85                  90                  95

Tyr Lys Val Leu Thr Leu Ala Ile Leu Asp Leu Pro Gly Leu Leu Phe
            100                 105                 110

Phe Ser Thr Phe Thr Leu Leu Val Leu Phe Trp Ala Glu Ile Tyr His
            115                 120                 125

Gln Ala Arg Ser Leu Pro Thr Asp Lys Leu Arg Ile Ser Tyr Ile Ala
            130                 135                 140

Ile Asn Asp Ala Ile Tyr Phe Ile Gln Ala Cys Ile Trp Val Tyr Leu
145                 150                 155                 160

Trp Ile Asn Asp Asn Ser Thr Val Glu Phe Ile Gly Lys Ile Phe Met
                165                 170                 175

Ala Val Val Ser Val Ile Ala Ala Leu Gly Phe Leu Leu Tyr Gly Gly
            180                 185                 190

Arg Leu Phe Leu Met Leu Arg Arg Phe Pro Ile Glu Ser Lys Gly Arg
            195                 200                 205

Arg Lys Lys Leu His Glu Val Gly Ser Val Thr Ala Ile Cys Phe Thr
            210                 215                 220

Cys Phe Leu Ile Arg Cys Phe Val Val Val Leu Ser Ala Phe Asp Ser
225                 230                 235                 240

Asp Ala Ser Leu Asp Val Leu Asp His Pro Val Leu Asn Leu Ile Tyr
                245                 250                 255
```

```
Tyr Leu Leu Val Glu Ile Leu Pro Ser Ala Leu Val Leu Tyr Ile Leu
        260                 265                 270

Arg Lys Leu Pro Pro Lys Arg Val Ser Ala Gln Tyr His Pro Ile Ser
        275                 280                 285
```

<210> SEQ ID NO 10
<211> LENGTH: 1251
<212> TYPE: DNA
<213> ORGANISM: Solanum lycopersicum

<400> SEQUENCE: 10

```
ctgaaaaagg tagttgccga ttttggtgtt tgattttttt ttggggggat tttgaaattg      60
gtgagtttga ttttggaatc tccggtgatg ggacgggcgg agatggttgt aggcccgtcg     120
gagaaggtgg cggtggtggc atatcatctg aatgatgcaa tcaattggtg ggacgatgtg     180
aacagatctc ttgattggca aaaccgtata ttccatgtcc ttgctgttct ctacggcgtt     240
gtcgccgtcg ttgctcttgt acaattaatt cgcattcaaa tgagagttcc tgaatatggc     300
tggaccactc aaaaagtctt ccactttctc aatttctttg tgaatggagt tcgctcgcta     360 gttttttacat ttcgtcggga tgttcagaag ttgcacccgg agattgtgca acatattatg     420
cttgatatgc caagtcttgc attcttcaca acttatgctc tgctagtatt attctgggct     480
gagatatact accaggcacg tgctgtgtcc acggatgggc ttagacctag tttcttcaca     540
atcaacggag tggtttatgc tattcagatt atattatggc tgataatgtg gtggaaacct     600
attcgagtac tcttcatctt atccaagatg ttttttgcag gtgtatccct atttgcagca     660
ttgggattTc tcctctacgg tggaaggctt tttcttatgt tacagcggtt tccagtagaa     720
tcaagaggga gacgcaagaa gctgcaggag gttggttatg tcacgacaat atgtttttca     780
tgcttcctca ttagatgcgt tatgatgtgc ttcaatgcat ttgataaagc tgcagatctt     840
gatgttttgt atcatcctat tttgaatttg atatattacc tgttagtgga gatactgcct     900
tcttctcttg tcctttttat tttaaggaag ttgcctccaa agcgagggat cacacaatac     960
caccctattc actaatacat taagagggta gataatgatg aaaatcaggc tccgggatca    1020
ggtattaagt aagttggctt ttacctggat gtgatttgca agcaagaaat acgagaggag    1080
tgataatgta aattgaagta tggttcgtct atactgaaat atccgtctgt cctcacacta    1140
ggcagattgt agctctgttt tgtaccacta gttatagatg gaattgtgaa gtatcttacg    1200
acctttagtg tattatttcg cctttgtatg tgtcagattt caattgaatt c            1251
```

<210> SEQ ID NO 11
<211> LENGTH: 295
<212> TYPE: PRT
<213> ORGANISM: Solanum lycopersicum

<400> SEQUENCE: 11

```
Met Gly Arg Ala Glu Met Val Val Gly Pro Ser Glu Lys Val Ala Val
1               5                   10                  15

Val Ala Tyr His Leu Asn Asp Ala Ile Asn Trp Trp Asp Asp Val Asn
            20                  25                  30

Arg Ser Leu Asp Trp Gln Asn Arg Ile Phe His Val Leu Ala Val Leu
        35                  40                  45

Tyr Gly Val Val Ala Val Val Ala Leu Val Gln Leu Ile Arg Ile Gln
    50                  55                  60

Met Arg Val Pro Glu Tyr Gly Trp Thr Thr Gln Lys Val Phe His Phe
65                  70                  75                  80
```

```
Leu Asn Phe Phe Val Asn Gly Val Arg Ser Leu Val Phe Thr Phe Arg
             85                  90                  95

Arg Asp Val Gln Lys Leu His Pro Glu Ile Val Gln His Ile Met Leu
            100                 105                 110

Asp Met Pro Ser Leu Ala Phe Phe Thr Thr Tyr Ala Leu Leu Val Leu
            115                 120                 125

Phe Trp Ala Glu Ile Tyr Tyr Gln Ala Arg Ala Val Ser Thr Asp Gly
    130                 135                 140

Leu Arg Pro Ser Phe Phe Thr Ile Asn Gly Val Val Tyr Ala Ile Gln
145                 150                 155                 160

Ile Ile Leu Trp Leu Ile Met Trp Trp Lys Pro Ile Arg Val Leu Phe
            165                 170                 175

Ile Leu Ser Lys Met Phe Phe Ala Gly Val Ser Leu Phe Ala Ala Leu
            180                 185                 190

Gly Phe Leu Leu Tyr Gly Gly Arg Leu Phe Leu Met Leu Gln Arg Phe
            195                 200                 205

Pro Val Glu Ser Arg Gly Arg Arg Lys Lys Leu Gln Glu Val Gly Tyr
    210                 215                 220

Val Thr Thr Ile Cys Phe Ser Cys Phe Leu Ile Arg Cys Val Met Met
225                 230                 235                 240

Cys Phe Asn Ala Phe Asp Lys Ala Ala Asp Leu Asp Val Leu Tyr His
            245                 250                 255

Pro Ile Leu Asn Leu Ile Tyr Tyr Leu Leu Val Glu Ile Leu Pro Ser
            260                 265                 270

Ser Leu Val Leu Phe Ile Leu Arg Lys Leu Pro Pro Lys Arg Gly Ile
            275                 280                 285

Thr Gln Tyr His Pro Ile His
    290                 295

<210> SEQ ID NO 12
<211> LENGTH: 23
<212> TYPE: DNA
<213> ORGANISM: Solanum lycopersicum

<400> SEQUENCE: 12
gttgtgaaga atgcaagact tgg                                                23

<210> SEQ ID NO 13
<211> LENGTH: 23
<212> TYPE: DNA
<213> ORGANISM: Solanum lycopersicum

<400> SEQUENCE: 13
tcaaagatgg ggcgaactcg tgg                                                23

<210> SEQ ID NO 14
<211> LENGTH: 23
<212> TYPE: DNA
<213> ORGANISM: Solanum lycopersicum

<400> SEQUENCE: 14
gccgattgac atcgccggtc cgg                                                23

<210> SEQ ID NO 15
<211> LENGTH: 23
<212> TYPE: DNA
<213> ORGANISM: Solanum lycopersicum
```

-continued

```
<400> SEQUENCE: 15
ccaagtcttg cattcttcac aac                                          23

<210> SEQ ID NO 16
<211> LENGTH: 30
<212> TYPE: DNA
<213> ORGANISM: Solanum lycopersicum

<400> SEQUENCE: 16
atgccaagta cttgcattct tcacaacttt                                   30

<210> SEQ ID NO 17
<211> LENGTH: 23
<212> TYPE: DNA
<213> ORGANISM: Solanum lycopersicum

<400> SEQUENCE: 17
ccacgagttc gccccatctt tga                                          23

<210> SEQ ID NO 18
<211> LENGTH: 24
<212> TYPE: DNA
<213> ORGANISM: Solanum lycopersicum

<400> SEQUENCE: 18
acaccacgag cccatctttg attg                                         24

<210> SEQ ID NO 19
<211> LENGTH: 23
<212> TYPE: DNA
<213> ORGANISM: Solanum lycopersicum

<400> SEQUENCE: 19
gccgattgac atcgccggtc cgg                                          23

<210> SEQ ID NO 20
<211> LENGTH: 27
<212> TYPE: DNA
<213> ORGANISM: Solanum lycopersicum

<400> SEQUENCE: 20
tcgccgattg acatcgccgt ccggtga                                      27

<210> SEQ ID NO 21
<211> LENGTH: 6
<212> TYPE: PRT
<213> ORGANISM: Solanum lycopersicum

<400> SEQUENCE: 21

Ser Pro Ile Asp Ile Ala
1               5

<210> SEQ ID NO 22
<211> LENGTH: 23
<212> TYPE: DNA
<213> ORGANISM: Solanum lycopersicum

<400> SEQUENCE: 22
ccaagtcttg cattcttcac aac                                          23

<210> SEQ ID NO 23
<211> LENGTH: 27
<212> TYPE: DNA
```

-continued

```
<213> ORGANISM: Solanum lycopersicum

<400> SEQUENCE: 23
atgccaagtt gcattcttca caacttt                                      27

<210> SEQ ID NO 24
<211> LENGTH: 307
<212> TYPE: RNA
<213> ORGANISM: Artificial Sequence
<220> FEATURE:
<223> OTHER INFORMATION: detection probe for CP gene sequence

<400> SEQUENCE: 24
ggguucgccu gauuuucgac uucuauaauc cuauuucuag uaucgaaagc uccuaacaaa      60
gcaguaacua gaggaucuag uaccgcauug uaccuauaca ccuuaaaacc acugucagga     120
aaccuaacag ugacuugagg gacaggguuc cacacuucgc uaaauugccg uugaacgguu     180
guucuagcuu guuguguuug gaacugauua ccuagugaau uaguacauaa auuuauuaau     240
ucuauagggu cggcccaugc ugaugacaaa aacacaaauu gcgauggagu ugcgauugug     300
uaagaca                                                            307

<210> SEQ ID NO 25
<211> LENGTH: 22
<212> TYPE: DNA
<213> ORGANISM: Artificial Sequence
<220> FEATURE:
<223> OTHER INFORMATION: forward primer for CP gene sequence detection
      probe

<400> SEQUENCE: 25
tgtcttacac aatcgcaact cc                                           22

<210> SEQ ID NO 26
<211> LENGTH: 45
<212> TYPE: DNA
<213> ORGANISM: Artificial Sequence
<220> FEATURE:
<223> OTHER INFORMATION: reverse primer for CP gene sequence detection
      probe

<400> SEQUENCE: 26
cgtacgtaat acgactcact atagggttcg cctgattttc gactt                  45
```

TOBAMOVIRUS-RESISTANT TOMATO PLANT, METHOD FOR PRODUCING TOBAMOVIRUS-RESISTANT TOMATO PLANT, METHOD FOR IMPARTING TOBAMOVIRUS RESISTANCE IN TOMATO PLANT, METHOD FOR SCREENING FOR TOBAMOVIRUS-RESISTANT TOMATO PLANT, AND METHOD FOR DETECTING TOBAMOVIRUS RESISTANCE IN TOMATO PLANT

SEQUENCE LISTING SUBMISSION VIA EFS-WEB

A computer readable text file, entitled "SequenceListing.txt," created on or about Sep. 10, 2020 with a file size of 26,588 bytes and contains the sequence listing for this application and is hereby incorporated by reference in its entirety.

TECHNICAL FIELD

The present invention relates to a *Tobamovirus*-resistant tomato plant, a method for producing a *Tobamovirus*-resistant tomato plant, a method for imparting *Tobamovirus* resistance to a tomato plant, a method for screening a *Tobamovirus*-resistant tomato plant, and a method for detecting *Tobamovirus* resistance in a tomato plant.

BACKGROUND ART

In tomato cultivation, the control of tomato mosaic virus (ToMV) of the genus *Tobamovirus* is essential, and tomato plants for cultivation are introduced with tomato mosaic virus resistance genes.

Tm-$2^2$ (Tm-2a) is known as a ToMV resistance gene that is less likely to be defeated and has been introduced into tomato plants of nearly all commercial cultivars. However, in 2015, Tomato brown rugose fruit virus (ToBRFV), which is a new *Tobamovirus* to which Tm-$2^2$ is ineffective, was discovered in the Middle East, and the spread of infected areas worldwide has become an issue (Non-Patent Literatures 1 and 2).

CITATION LIST

Non-Patent Literature

[Non-Patent Literature 1]: N. Salem et. al., "Anew *Tobamovirus* infecting tomato crops in Jordan," Arch. Virol., 2016, vol. 161, pages 503-506; and

[Non-Patent Literature 2]: Neta Luria et. al., "A New Israeli *Tobamovirus* Isolate Infects Tomato Plants Harboring Tm-$2^2$ Resistance Genes," PLOS One, 2017, vol. 12, No. 1, e0170429

SUMMARY OF INVENTION

Technical Problem

With the foregoing in mind, it is an object of the present invention to provide a tomato plant which is resistant to ToBRFV.

Solution to Problem

In order to achieve the above object, the present invention provides a *Tobamovirus* resistant tomato plant (hereinafter, also referred to as a "resistant plant") with loss of function for a SlTOM1a gene, a SlTOM1c gene, and a SlTOM1d gene.

The present invention also provides a method for producing a *Tobamovirus* resistant tomato plant (hereinafter, also referred to as a "first production method"), including the following step (a):

(a) crossing the *Tobamovirus* resistant tomato plant according to the present invention with another tomato plant.

The present invention also provides a method for imparting *Tobamovirus* resistance to a tomato plant (hereinafter, also referred to as an "imparting method"), including the step of: causing loss of function for a SlTOM1a gene, a SlTOM1c gene, and a SlTOM1d gene of a target tomato plant.

The present invention also provides a method for producing a *Tobamovirus* resistant tomato plant (hereinafter, also referred to as a "second production method"), including the step of: imparting *Tobamovirus* resistance to a target tomato plant, wherein the imparting is carried out by the method for imparting *Tobamovirus* resistance to a tomato plant according to the present invention.

The present invention also provides a method for screening a *Tobamovirus* resistant tomato plant (hereinafter, also referred to as a "screening method"), including the step of: selecting a tomato plant to be examined with loss of function for a SlTOM1a gene, a SlTOM1c gene, and a SlTOM1d gene from one or more tomato plants to be examined as a *Tobamovirus* resistant tomato plant.

The present invention also provides a method for producing a *Tobamovirus* resistant tomato plant (hereinafter, also referred to as a "third production method"), including the step of: screening a tomato plant to be examined with loss of function for a SlTOM1a gene, a SlTOM1c gene, and a SlTOM1d gene from one or more tomato plants to be examined, wherein the screening is carried out by the method for screening a *Tobamovirus* resistant tomato plant according to the present invention.

The present invention also provides a method for detecting *Tobamovirus* resistance in a tomato plant (hereinafter, also referred to as a "detection method"), including the step of: detecting whether or not a SlTOM1a gene, a SlTOM1c gene, and a SlTOM1d gene lose function in a tomato plant to be examined.

The present invention also provides a tomato plant processed food using the *Tobamovirus* resistant tomato plant according to the present invention.

Advantageous Effects of Invention

The tomato plant of the present invention is resistant to ToBRFV.

DESCRIPTION OF EMBODIMENTS

*Tobamovirus* Resistant Tomato Plant

Figure 1A:
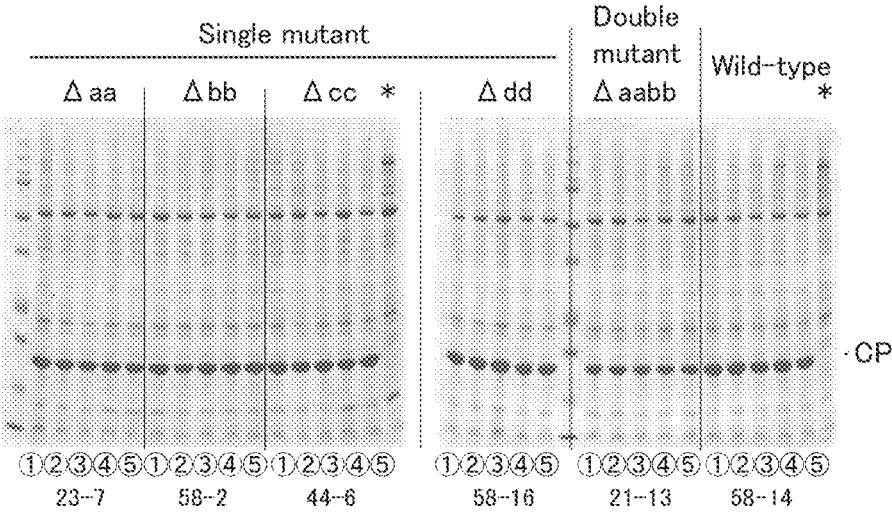
FIGS. 1A to 1C are photographs each showing a staining diagram after CBB staining in Example 1.

As described above, a *Tobamovirus* resistant tomato plant of the preset invention is with loss of function for a SlTOM1a gene, a SlTOM1c gene, and a SlTOM1d gene. The *Tobamovirus* resistant tomato plant of the present invention is characterized in that it is with loss of function for a SlTOM1a gene, a SlTOM1c gene, and a SlTOM1d gene, and other configurations and conditions are not particularly limited.

As a result of intensive studies, the inventors of the present invention have found that *Tobamovirus* utilizes *Solanum lycopersicum* TOM1 (SlTOM1) genes in infecting tomato plants. The inventors have found that tomato plants become resistant to ToBRFV in addition to ToMV by causing loss of function for a SlTOM1a gene, a SlTOM1c gene, and a SlTOM1d gene in the SlTOM1 gene group, in particular, by combining the loss of function for a SlTOM1d gene with loss of function for another gene in the SlTOM1 gene group, and have established the present invention. This is presumed to be because, while *Tobamovirus* uses the SlTOM1 gene group in RNA replication, *Tobamovirus* cannot grow due to loss of function for a SlTOM1a gene, a SlTOM1c gene, and a SlTOM1d gene. It should be noted that the present invention is not limited in any way to the foregoing presumption. Accordingly, the present invention can provide a tomato plant which is resistant to *Tobamovirus* in particular to ToBRFV.

*Tobamovirus*, as used herein, means a virus belonging to the genus *Tobamovirus*. Examples of the virus belonging to the genus *Tobamovirus* include Tomato mosaic virus (ToMV), Tomato brown rugose fruit virus (ToBRFV), Tomato mottle mosaic virus (ToMMV), Tobacco mosaic virus, Cucumber green mottle mosaic virus, Pepper mild mottle virus, Tobacco mild green mosaic virus, Paprika mild mottle virus, Kyuri green mottle mosaic virus, Hibiscus latent Fort Pierce virus, Odontoglossum ringspot virus, Rehmannia mosaic virus, Sammon's Opuntia virus, Wasabi mottle virus, Youcai mosaic virus, and Sunn-hemp mosaic virus. The *Tobamovirus* is preferably a *Tobamovirus* capable of infecting tomato plants. Examples of the *Tobamovirus* capable of infecting tomato plants include ToMV, ToBRFV, and ToMMV.

In the present invention, "*Tobamovirus* resistance" also may be referred to as "*Tobamovirus* tolerance", for example. The resistance means the ability to inhibit or suppress the occurrence and progression of damage due to the infection with the *Tobamovirus*, for example. Specifically, the resistance may mean any of the following, for example: to prevent the damage from occurring; to stop the progression of the damage that has occurred already; and to suppress (also referred to as "inhibit") the progression of the damage that has occurred already.

In the present invention, the *Tobamovirus* resistant tomato plant may be resistant to any one or more Tobamoviruses, preferably to ToBRFV or ToMV, and more preferably to ToBRFV and ToMV.

In the present invention, "*Tobamovirus* resistance" is meant to be significantly resistant to *Tobamovirus*, for example, compared to a tomato plant having a wild-type SlTOM1 gene group (normal SlTOM1 gene group). In the present invention, "*Tobamovirus* resistance" can be evaluated, for example, by inoculating the cotyledons of the tomato plant to be examined (about 10 days after water absorption) with *Tobamovirus*, on the basis of measurement of the presence or absence or level of expression of the coat protein of *Tobamovirus* in a predetermined period (about 7 days) after inoculation, or the onset of disease or severity of disease caused by *Tobamovirus* after a predetermined period (about 20 days) after inoculation.

In the case of evaluating *Tobamovirus* resistance on the basis of expression of the coat protein, regarding the expression of the coat protein, reference can be made to the description of Example 1 to be described below. If the expression level of the coat protein in the tomato plant to be examined is the same as (not significantly different from) that of the coat protein in a tomato plant including a loss-of-function gene (also referred to as the loss of function body) of a SlTOM1a gene, a loss-of-function gene for a SlTOM1c gene, and a loss-of-function gene for a SlTOM1d gene in a homozygous form, and/or if the expression level of the coat protein in the tomato plant to be examined is (significantly) lower than that of the coat protein in a tomato plant including a loss-of-function gene for a SlTOM1a gene, a loss-of-function gene for a SlTOM1c gene, and a loss-of-function gene for a SlTOM1d gene in a homozygous form, for example, the tomato plant to be examined can be evaluated as a tomato plant resistant to *Tobamovirus*. If the expression level of the coat protein in the tomato plant to be examined is the same as (not significantly different from) or (significantly) higher than that of the coat protein in a tomato plant including a wild-type SlTOM1a gene, a wild-type SlTOM1c gene, and a wild-type SlTOM1d gene in a homozygous form, and/or if the expression level of the coat protein in the tomato plant to be examined is (significantly) higher than that of the coat protein in a tomato plant including a loss-of-function gene for a SlTOM1a gene, a loss-of-function gene for a SlTOM1c gene, and a loss-of-function gene for a SlTOM1d gene in a homozygous form, for example, the tomato plant to be examined can be evaluated as a tomato plant susceptible to *Tobamovirus*.

In the case of evaluating *Tobamovirus* resistance on the basis of the onset of disease caused by *Tobamovirus*, the onset of the disease caused by *Tobamovirus* can be judged, for example, based on whether or not to form filiform leaf and/or present or absence of growth retardation with reference to the symptoms described in the following Reference Information 1. The filiform leaf means, for example, that a part of the leaf shrinks and exhibits a filiform form, and as a specific example, reference can be made to the examples of Symptoms of ToBRFV (German DSMZ isolate) on *Solanum lycopersicum* cv. 'moneymaker' obtained by artificial inoculation under quarantine facilities (France, 2019) in the following Reference 1 Information. When the tomato plant to be examined is infected with *Tobamovirus*, for example, the formation of filiform leaf and/or growth retardation is observed in the tomato plant to be examined. Thus, if the tomato plant to be examined forms filiform leaf and/or is delayed in growth, the tomato plant to be examined can be evaluated to be suffering from *Tobamovirus*, i.e., susceptible to *Tobamovirus*. On the other hand, if the tomato plant to be examined does not form filiform leaf and/or is not delayed in growth, the tomato plant to be examined can be evaluated to be not suffering from *Tobamovirus*, i.e., resistant to *Tobamovirus*. The growth retardation may be evaluated by comparison with tomato plants not infected with *Tobamovirus* (e.g., individuals not inoculated with *Tobamovirus*), or may be evaluated by comparison with the growth state of general tomato plants in consideration of the number of cultivation days of the tomato plants to be examined.

Reference Information 1: European and Mediterranean Plant Protection Organization (EPPO), "EPPO Global Database", [online], [searched on Feb. 12, 2020], <gd.eppo.int/taxon/tobrfv/photos>

As a specific example, the "*Tobamovirus* resistance" can be expressed by evaluating the disease index of the tomato plant and calculating the severity from the disease index in the same manner as in the method of Example 2 described below. Regarding the calculation of the severity according to this method, reference can be made to the description of Example 2 to be described below, and the disease index of less than 1 can be evaluated as being resistant (tolerant) to *Tobamovirus* and the disease index of 1 or more can be evaluated as being susceptible to *Tobamovirus*, for example. When the *Tobamovirus* resistance is determined according to the severity, the severity may be, for example, the severity of a single tomato plant or the average severity of two or more tomato plants, and the latter is preferable. In the latter case, the number of tomato plants used for determining the *Tobamovirus* resistance is not particularly limited, and may be, for example, sufficient to conduct statistical test in comparison with *Tobamovirus* susceptible tomato plants. As a specific example, the number of tomato plants may be 5 to 20, or 5.

In the present invention, a "tomato plant" refers to a plant classified in Section Lycopersicon in the Subgenus *Solmum sensu stricto* of the genus *Solanum*. Specific examples of the tomato plant include *S. lycopersicum, S. peruvianum, S. arcanum* Peralta, *S. chilense, S. corneliomulleri, S. huaylasense* Peralta, *S. cheesmaniae* (L. Riley) Fosberg, *S. chmielewskii, S. galapagense,* S. C. Darwin & Peralta, *S. habrochaites, S. neorickii, S. pennelli,* and *S. pimpinellifolium*. Among them, *S. lycopersicum* is preferable because it can be crossed easily. In the present invention, the tomato plant is, for example, a tomato plant for cultivation. The tomato plant for cultivation can also be referred to as, for example, a cultivar of a tomato plant.

The term "plant body" as used in the present invention may refer to either a plant individual representing the whole plant or a part of the plant individual. The part of the plant individual may be any of organs, tissues, cells, and propagules, for example. Examples of the organs include petals, corollas, flowers, leaves, seeds, fruits, stems, and roots. The tissue is a part of the organ, for example. The part of the plant body may be one type of organ, tissue, and/or cell, or two or more types of organs, tissues, and/or cells, for example.

As described above, *Tobamovirus* is presumed to utilize a SlTOM1 gene group in infecting tomato plants. In other words, the SlTOM1 gene group can be referred to as genes having *Tobamovirus* resistance control activity. In the present invention, a gene having the *Tobamovirus* resistance control activity means that the appearance of the trait of *Tobamovirus* resistance is suppressed if the gene is present in a normal state (e.g., a wild-type gene), that is, the *Tobamovirus* resistance is negatively controlled. Therefore, the "*Tobamovirus* resistance control activity" can also be referred to as, for example, "*Tobamovirus* resistance suppression activity". Further, since the SlTOM1 gene group is a gene group having *Tobamovirus* resistance control activity, the genes constituting the SlTOM1 gene group can also be referred to as *Tobamovirus* resistance control genes, for example. The "*Tobamovirus* resistance control activity gene" can be referred to as, for example, a "*Tobamovirus* resistance suppression activity gene." In addition, the genes constituting the SlTOM1 gene group are presumed to contribute to *Tobamovirus* resistance by controlling *Tobamovirus* growth or RNA replication, as described above. Thus, the genes constituting the SlTOM1 gene group can also be referred to as, for example, *Tobamovirus* growth control genes or *Tobamovirus* replication-control genes. In the following description, the genes constituting the SlTOM1 gene group refer to a SlTOM1a gene, a SlTOM1b gene, a SlTOM1c gene, and/or a SlTOM1d gene, unless otherwise mentioned.

In the present invention, the SlTOM1 gene group and the genes constituting the SlTOM1 gene group described below may exist in the form of RNA (e.g., mRNA) or in the form of DNA (e.g., cDNA or genomic DNA). The DNA may be a double-stranded DNA or a single-stranded DNA. In the present invention, the gene may include an additional sequence such as a sequence of an untranslated region (UTR).

In tomato plants, the SlTOM1 gene group includes a SlTOM1b gene in addition to a SlTOM1a gene, a SlTOM1c gene, and a SlTOM1d gene. Each of the genes will be described below. In the following description, the SlTOM1a gene, the SlTOM1b gene, the SlTOM1c gene, and the SlTOM1d gene mean to be a normal SlTOM1a gene, a normal SlTOM1b gene, a normal SlTOM1c gene, and a normal SlTOM1d gene, respectively, i.e., a wild-type SlTOM1a gene, a wild-type SlTOM1b gene, a wild-type SlTOM1c gene, and a wild-type SlTOM1d gene, respectively, each of which having *Tobamovirus* resistance control activity. The SlTOM1a gene can also be referred to as LeTH1. Examples of the SlTOM1a gene include a polynucleotide consisting of a base sequence (SEQ ID NO: 1) registered under Accession No.: Solyc04g008540 in Sol genomics network (Solyc: solgenomics.net/) and a polynucleotide consisting of a base sequence (SEQ ID NO: 2) registered under Accession No.: AB193041 in a Genbank. In each of the following base sequences, the underlined base sequence is a base sequence encoding a protein unless otherwise specified. Further, examples of the protein encoded by the SlTOM1a gene include a polypeptide consisting of an amino acid sequence (SEQ ID NO: 3) registered under Accession No.: Solyc04g008540 in the Solyc and a polypeptide consisting of a base sequence (SEQ ID NO: 3) registered under Accession No.: AB193041 in the Genbank.

cDNA sequence of SlTOM1a gene (SEQ ID NO: 1, Solyc04g008540):
5'-TAATAGTCAAAAAGAATAAATCCTAGAACGTTCAGGGAACGCCGCTGT

GTTTCTCTCCTTTCTCGCCGGCCGTTTTAGGCTCAATAATTTTCTGATCAA

ACAAAAAATTCTCTAAAATTTCATTTATTTCGTATTTTTTGGTGTGTCTAA

TTTCGGATCTCCGGCGATGGGTCGGGTTGAAACAGCGGTGGACCCGTCGTC

GACGGCTGCGGTGGCGGCGTACCGTTTACATGAGGCAATAAGCTGGTGGGA

TGAAGTGAATGAATCTCCTATTTGGCAAGACCGTATTTTCTATGTCCTTGC

GATCTTATACGGCGTCGTTTCTGCTGTTGCTCTTGTGCAATTAATCCGGAT

TCAGATGAGAGTTCCCGAGTATGGATGGACCACTCAGAAAGTCTTCCATTT

CCTCAATTTCTTGGTGAATGGGGTTCGCTCTCTGGTTTTTGTATTTCGTCG

GGATGTTCAGAAGTTGAACCCTGAGATTATCCAACACATCTTGCTTGATAT

GCCAAGTCTTGCATTCTTCACAACTTTTGCGCTTCTAGTATTGTTCTGGGC

TGAGATATACTATCAGGCACGTGCTGTATCTACTGATGCTCTTAGGCCTAG

-continued

```
TTTCTTCACAATCAATGGAGTTGTTTATGCTATTCAGATTATTTTATGGCT

GATAATATGGTGGAAGCCTGTTCCAGTACTCGTCATCTTATCGAAGGCATT

CTTTGCAGGTGTATCTCTATTTGCAGCCTTGGGGTTTCTTCTTTATGGAGG

AAGGCTTTTCCTTATGTTACGGCGTTTCCCTGTAGAATCAAGGGGGAGACA

GAAGAAACTTCAGGAAGTTGGTTATGTGACAACAATATGTTTTTCATGCTT

CCTGATTAGATGCATTATGATGTGTTTCAATGCATTTGATAAAGCTGCGGA

TCTTGATGTTTTATATCATCCAATGTTAAATTTTGTATACTATCTGTTGGT

AGAGATTCTACCTTCTTCACTTGTCCTTTTCATTTTGAGGAAGTTGCCTCC

AAAGCGAGGGATCACGCAGTACCACCCTATTCGCTGATACAACAGCGTGCA

TCGGATGATGAAATCAAGCGCTGGGATCAGGTTATCAGATGAGTTGGCTTT

TACGATACTCGTCCTACCCATATAGTGAGATACTGTACATGGAGCATGGTT

CATCAGGACTCTGGAAAAATAGTTTGTTCTCTGCAGATATTAGTTGTGTCT

GTAATTTGTTTGTAGTCTTGATACAAGAGTTGTGGAAGAAGTTGTGTTATT

TCTAGTGTAATTATCTTCATATTTGTATGTTTGAGATTTCAATTGATTATT

C-3' cDNA sequence of S1TOM1a gene (SEQ ID NO: 2,
AB193041):
5'-GAAAAGAATAAATCCTAGAACGTTCAGGGAACGCCGCTGTGTTTCTC

TCCTTTCTCGCCGGCCGTTTTAGGCTCAATAATTTTCTGATCAAACAAAAA

ATTCTCTAAAATTTCATTTATTTCGTATTTTTTGGTGTGTCTAATTTCGGA

TCTCCGGCGATGGGTCGGGTTGAAACAGCGGTGGACCCGTCGTCGACGGCT

GCGGTGGCGGCGTACCGTTTACATGAGGCAATAAGCTGGTGGGATGAAGTG

AATGAATCTCCTATTTGGCAAGACCGTATTTTCTATGTCCTTGCGATCTTA

TACGGCGTCGTTTCTGCTGTTGCTCTTGTGCAATTAATCCGGATTCAGATG

AGAGTTCCCGAGTATGGATGGACCACTCAGAAAGTCTTCCATTTCCTCAAT

TTCTTGGTGAATGGGGTTCGCTCTCTGGTTTTTGTATTTCGTCGGGATGTT

CAGAAGTTGAACCCTGAGATTATCCAACACATCTTGCTTGATATGCCAAGT

CTTGCATTCTTCACAACTTTTGCGCTTCTAGTATTGTTCTGGGCTGAGATA

TACTATCAGGCACGTGCTGTATCTACTGATGCTCTTAGGCCTAGTTTCTTC

ACAATCAATGGAGTTGTTTATGCTATTCAGATTATTTTATGGCTGATAATA

TGGTGGAAGCCTGTTCCAGTACTCGTCATCTTATCGAAGGCATTCTTTGCA

GGTGTATCTCTATTTGCAGCCTTGGGGTTTCTTCTTTATGGAGGAAGGCTT

TTCCTTATGTTACGGCGTTTCCCTGTAGAATCAAGGGGGAGACAGAAGAAA

CTTCAGGAAGTTGGTTATGTGACAACAATATGTTTTTCATGCTTCCTGATT

AGATGCATTATGATGTGTTTCAATGCATTTGATAAAGCTGCGGATCTTGAT

GTTTTATATCATCCAATGTTAAATTTTGTATACTATCTGTTGGTAGAGATT

CTACCTTCTTCACTTGTCCTTTTCATTTTGAGGAAGTTGCCTCCAAAGCGA

GGGATCACGCAGTACCACCCTATTCGCTGATACAACAGCGTGCATCGGATG

ATGAAATCAAAGCGCTGGGATCAGGTTATCAGATGAGTTGGCTTTTACGAT

ACTCGTCCTACCCATATAGTGAGATACTGTACATGGAGCATGGTTCATCAG

GACTCTGGAAAAATAGTTTGTTCTCTGCAGATATTAGTTGTGTCTGTAATT
```

-continued

```
TGTTTGTAGTCTTGATACAAGAGTTGTGGAAGAAGTTGTGTTATTTCTAGT

GTAATTATCTTCATATTTGTATGTTTGAGATTTCAATTGATTATTCTTTTC

CCCCAAAAAAAAAAAAAAAATCCTGCGGCA-3'
```

```
Protein encoded by S1TOM1a gene (SEQ ID NO: 3,
Solyc04g008540, AB193041):
MGRVETAVDPSSTAAVAAYRLHEAISWWDEVNESPIWQDRIFYVLAILYGV

VSAVALVQLIRIQMRVPEYGWTTQKVFHFLNFLVNGVRSLVFVFRRDVQKL

NPEIIQHILLDMPSLAFFTTFALLVLFWAEIYYQARAVSTDALRPSFFTIN

GVVYAIQIILWLIIWWKPVPVLVILSKAFFAGVSLFAALGFLLYGGRLFLM

LRRFPVESRGRQKKLQEVGYVTTICFSCFLIRCIMMCFNAFDKAADLDVLY

HPMLNFVYYLLVEILPSSLVLFILRKLPPKRGITQYHPIR
```

As a specific example, the SlTOM1a gene is, for example, a *Tobamovirus* resistance control gene including the following polynucleotide (NA):

(NA) any of the following polynucleotides (NA1) to (NA7):

(NA1) a polynucleotide consisting of a base sequence of SEQ ID NO: 1 or 2;

(NA2) a polynucleotide consisting of a base sequence obtained by deletion, substitution, insertion, and/or addition of one or several bases in a base sequence of the polynucleotide (NA1), and encoding a protein having *Tobamovirus* resistance control activity;

(NA3) a polynucleotide consisting of a base sequence having at least 80% sequence identity to the base sequence of the polynucleotide (NA1), and encoding a protein having *Tobamovirus* resistance control activity;

(NA4) a polynucleotide consisting of a base sequence complementary to a polynucleotide that hybridizes to a polynucleotide consisting of the base sequence of the polynucleotide (NA1) under stringent conditions, and encoding a protein having *Tobamovirus* resistance control activity;

(NA5) a polynucleotide encoding a protein consisting of an amino acid sequence of SEQ ID NO: 3;

(NA6) a polynucleotide consisting of an amino acid sequence obtained by deletion, substitution, insertion, and/or addition of one or several amino acids in the amino acid sequence of SEQ ID NO: 3, and encoding a protein having *Tobamovirus* resistance control activity; and (NA7) a polynucleotide consisting of an amino acid sequence having at least 80% sequence identity to the amino acid sequence of SEQ ID NO: 3, and encoding a protein having *Tobamovirus* resistance control activity.

In the polynucleotides (NA2) to (NA4) and (NA6) to (NA7), "having *Tobamovirus* resistance control activity" means, for example, having *Tobamovirus* resistance control activity equivalent to (not significantly different from) that of the polynucleotide (NA1) or (NA5).

In the polynucleotide (NA1), the base sequence of SEQ ID NO: 1 is a coding sequence of the polynucleotide (NA5). The base sequence of SEQ ID NO: 1 can be obtained, for example, from *S. lycopersicum* cv. Heinz 1706. In addition, in the polynucleotide (NA1), the base sequence of SEQ ID NO: 2 is a coding sequence of the polynucleotide (NA5). The base sequence of SEQ ID NO: 2 can be obtained, for example, from *S. lycopersicum* cv. Craigella GCR26.

In the polynucleotide (NA2), "one or several" bases may be, for example, in a range in which the protein encoded by the polynucleotide (NA2) has the *Tobamovirus* resistance control activity. The "one or several" bases in the polynucleotide (NA2) is, for example, 1 to 264, 1 to 198, 1 to 132, 1 to 66, 1 to 52, 1 to 39, 1 to 26, 1 to 13, 1 to 6, 1 to 3, 1 to 2, or 1 in the sequence of the polynucleotide (NA1). In the present invention, the numerical range regarding the number of bases or amino acids discloses all the positive integers falling within that range, for example. That is, for example, the description "one to five bases" discloses all of "one, two, three, four, and five bases" (the same applies hereinafter).

In the polynucleotide (NA3), "sequence identity" may be, for example, in a range in which the protein encoded by the polynucleotide (NA3) has the *Tobamovirus* resistance control activity. The sequence identity of the polynucleotide (NA3) relative to the base sequence of the polynucleotide (NA1) is, for example, at least 80%, at least 85%, at least 90%, at least 95%, at least 96%, at least 97%, at least 98%, or at least 99%. The "sequence identity" can be determined by aligning two base sequences or amino acid sequences (the same applies hereinafter). The alignment can be calculated by, for example, using a BLAST, FASTA or the like with default parameters.

In the polynucleotide (NA4), "polynucleotide that hybridizes" is, for example, a polynucleotide that is completely or partially complementary to the polynucleotide (NA1). The hybridization can be detected, for example, by various hybridization assays. The hybridization assays are not particularly limited, and methods described, for example, in Sambrook et al., "Molecular Cloning: A Laboratory Manual 2$^{nd}$ Ed." [Cold Spring Harbor Laboratory Press (1989)] and the like may also be employed.

In the polynucleotide (NA4), "stringent conditions" may be, for example, low stringent conditions, medium stringent conditions, or high stringent conditions. The "low stringent conditions" are, for example, conditions of 5×SSC, 5× Denhart's solution, 0.5% SDS, 50% formamide, and 32° C. The "medium stringent conditions" are, for example, conditions of 5×SSC, 5× Denhart's solution, 0.5% SDS, 50% formamide, and 42° C. The "high stringent conditions" are, for example, conditions of 5×SSC, 5× Denhart's solution, 0.5% SDS, 50% formamide, and 50° C. The degree of stringency can be set by those skilled in the art, for example, by appropriately selecting conditions such as the temperature, the salt concentration, the concentration and length of the probe, the ionic strength, the time, and the like. As the "stringent conditions", the conditions described in, for example, Sambrook et al., "Molecular Cloning: A Laboratory Manual 2$^{nd}$ Ed." [Cold Spring Harbor Laboratory Press (1989)] and the like may also be employed.

The sequence of the polynucleotide (NA5) is not particularly limited as long as, for example, the protein encoded by the polynucleotide (NA5) has the *Tobamovirus* resistance control activity. The base sequence of the polynucleotide (NA5) can be designed, for example, by substituting with the corresponding codon based on the amino acid sequence of SEQ ID NO: 3.

In the polynucleotide (NA6), "one or several" bases regarding an amino acid sequence may be, for example, in a range in which the protein encoded by the polynucleotide (NA6) has the *Tobamovirus* resistance control activity. The "one or several" bases in the polynucleotide (NA6) is, for example, 1 to 59, 1 to 58, 1 to 44, 1 to 43, 1 to 30, 1 to 29, 1 to 15, 1 to 14, 1 to 11, 1 to 8, 1 to 6, 1 to 5, 1 to 3, 1 to 2, or 1 in the amino acid sequence of SEQ ID NO: 3.

In the polynucleotide (NA7), "sequence identity" regarding an amino acid sequence may be, for example, in a range in which the protein encoded by the polynucleotide (NA7)

has the *Tobamovirus* resistance control activity. The sequence identity of the polynucleotide (NA7) relative to the amino acid sequence of SEQ ID NO: 3 is, for example, at least 80%, at least 85%, at least 90%, at least 95%, at least 96%, at least 97%, at least 98%, or at least 99%.

The SlTOM1b gene can also be referred to as LeTH2. Examples of the SlTOM1b gene include a polynucleotide consisting of a base sequence (SEQ ID NO: 4) registered under Accession No.: Solyc01g105270 in the Solyc and a polynucleotide consisting of a base sequence (SEQ ID NO: 5) registered under Accession No.: AB193042 in the Genbank. Examples of the protein encoded by the SlTOM1b gene include a polypeptide consisting of an amino acid sequence (SEQ ID NO: 6) registered under Accession No.: Solyc01g105270 in the Solyc and a polynucleotide consisting of a base sequence (SEQ ID NO: 6) registered under Accession No.: AB193043 in the Genbank.

cDNA base sequence of SlTOM1b gene (SEQ ID NO: 4, Solyc01g105270):

5'-TACATTTGTCCTCCTTCCCCCTTCATCCACGTGTGGTTCCTCCAAACC

CTCCACCCCACTCTTCACTCTATTTGATTTGAACGAACATCCCCATCACTT

CACTCTCTACATTTTTCTTCATCTGTAAATCACCATTTTTGTTAGACGTAG

TAGCTATGGTAAAATCTATAAGCTTTCTTCTTGAATTCGCAAAAGATTACG

ATGATGGAACACCACGAGTTCGCCCCATCTTTGATTGGTTCAATGCGATGA

TGGAGGTCTCCGATTATGAGAAACAAGCCATCTTTTATTCTCTCTCTGCCG

CCTATGCCTTAGTCTCATTTGTTGCACTGGTACAACTCATCCGCATCCAAT

TGCGCCTTTCAGGAATTGGTTGGACAACACAAAAGGTTTTTCACTTGATGA

ATTTTGTTGTCTGTGGATTGAGAGCAATATTATTTGGGTTCTACAGCAGCG

TGTTCAATCTTAGATCAAAAGCACTTGAGATGATGCTTCTGGATCTCCCCG

GTCTTCTATTCTTCTCCACATACACACTATTAGTTCTGTTTTGGGCTGAAA

TATTCCATCAGGCAAGAAACCTTCCAATCGATAAACTTCGACCTGCATATT

ATGCAGTTAATGCAGTCGTATATTTTATACAGATATGCATATGGATCTTCA

TCGGTGTTGGCCCAGCTTCGGCTGCTGTTGAAACTGCTAAACTTTTTTTCG

CAGTTATTTCATTTACTGCTGCTCTGGGATTTGTTATGTATGGTGGAAGGT

TGTTCGCTATGCTTCGGCGCTTCCCTATTGAATCTAGAGGCCGTCAAAAGA

AGCTTCATGAGGTTGGTTTCGTGACTGGTATTTGCTGCATTTGTTTCATGA

TCAGATGTGTTATGGTTGCTGTTTCTGCTTTTAACGGGAACGCTGATGTTG

ATGTCATTGACCATCCAGTTCTCATTCTCTTCTATTACGTGGTGGTGGAGA

TCTTGCCTTCTGTTTTGGTGCTTTTTATTCTGCGCAAATTACCTCCAAAAC

GTGTATCAGAGCAATATCATCCTATCCAATAACTCATAGAAGAGCATCCCT

GATTTTAGTACTTCACCGTTTTTGTTCAAAGAAGCCCTTGTCATGCCAGCC

AAGTTTTTAGTTCTTATAATATCATTTTTGCTTTTATTGTTTTGGCGCTTG

CTCTCGAGTGAGTGGAGGAGTTATAGTTTGATTTCAGTACAGCTCTGTAGA

AGTCTTGAATTATAAATTATTCAAAGTGCATGTGACTTGTAATCATTTGGA

TAGAATTAGATGTTCGAAGTTTAAAGGCCTTGGG-3'

-continued

```
cDNA base sequence of SlTOM1b gene (SEQ ID NO: 5,
AB193042):
5'-GACATTTGTCCTCCTTCCCCCCTCATCCACGTGTGGTTCCTCCAAACC

CTCCACCCCACTCTTCACTCTATTTGATTTGAACGAACATCCCCATCACTT

CACTCTCTACATTTTTCTTCATCTGTAAATCACCATTTTTGTTAGACGTAG

TAGCTATGGTAAAATCTATAAGCTTTCTTCTTGAATTCGCAAAAGATTACG

ATGATGGAACACCACGAGTTCGCCCCATCTTTGATTGGTTCAATGCGATGA

TGGAGGTCTCCGATTATGAGAAACAAGCCATCTTTTATTCTCTCTCTGCCG

CCTATGCCTTAGTCTCATTTGTTGCACTGGTACAACTCATCCGCATCCAAT

TGCGCCTTTCAGGAATTGGTTGGACAACACAAAAGGTTTTTCACTTGATGA

ATTTTGTTGTCTGTGGATTGAGAGCAATATTATTTGGGTTCTACAGCAGCG

TGTTCAATCTTAGATCAAAAGCACTTGAGATGATGCTTCTGGATCTCCCCG

GTCTTCTATTCTTCTCCACATACACACTATTAGTTCTGTTTTGGGCTGAAA

TATTCCATCAGGCAAGAAACCTTCCAATCGATAAACTTCGACCTGCATATT

ATGCAGTCAATGCAGTCGTATATTTTATACAGATATGCATATGGATCTTCA

TCGGTGTTGGCCCAGCTTCGGCTGCTGTTGAAACTGCTAAACTTTTTTTCG

CAGTTATTTCATTTACTGCTGCTCTGGGATTTGTTATGTATGGTGGAAGGT

TGTTCGCTATGCTTCGGCGCTTCCCTATTGAATCTAGAGGCCGTCAAAAGA

AGCTTCATGAGGTTGGTTTCGTGACTGGTATTTGCTGCATTTGTTTCATGA

TCAGATGTGTTATGGTTGCTGTTTCTGCTTTTAACGGGAACGCTGATGTTG

ATGTCATTGACCATCCAGTTCTCATTCTCTTCTATTACGTGGTGGTGGAGA

TCTTGCCTTCTGTTTTGGTGCTTTTTATTCTGCGCAAATTACCTCCAAAAC

GTGTATCAGAGCAATATCATCCTATCCAATAACTCATAGAAGAGCATCCCT

GATTTTAGTACTTCACCGTTTTTGTTCAAAGAAGCCCTTGTCATGCCAGCC

AAGTTTTTAGTTCTTATAATATCATTTTTGCTTTTATTGTCTTGACGCTTG

TCTCGAGTGACGTGGAGGAGTTATAGTTTGATTTCAGTACAGCTCTGTAGA

AGTCTTGAATTATAAATTATTCAAAGTGCATGTGACTTGTAATCATTTGGA

TAGAATTAGATGTTCGAAGTTTAAAGGCCTTGGGTTATATTGTG-3'

Protein encoded by SlTOM1b gene (SEQ ID NO: 6,
Solyc01g105270, AB193042):
MVKSISFLLEFAKDYDDGTPRVRPIFDWFNAMMEVSDYEKQAIFYSLSAAY

ALVSFVALVQLIRIQLRLSGIGWTTQKVFHLMNFVVCGLRAILFGFYSSVF

NLRSKALEMMLLDLPGLLFFSTYTLLVLFWAEIFHQARNLPIDKLRPAYYA

VNAVVYFIQICIWIFIGVGPASAAVETAKLFFAVISFTAALGFVMYGGRLF

AMLRRFPIESRGRQKKLHEVGFVTGICCICFMIRCVMVAVSAFNGNADVDV

IDHPVLILFYYVVVEILPSVLVLFILRKLPPKRVSEQYHPIQ
```

As a specific example, the SlTOM1b gene is, for example, a *Tobamovirus* resistance control gene including the following polynucleotide (NB):

(NB) any of the following polynucleotides (NB1) to (NB7):

(NB1) a polynucleotide consisting of a base sequence of SEQ ID NO: 4 or 5;

(NB2) a polynucleotide consisting of a base sequence obtained by deletion, substitution, insertion, and/or addition of one or several bases in a base sequence of the polynucleotide (NB1), and encoding a protein having *Tobamovirus* resistance control activity;

(NB3) a polynucleotide consisting of a base sequence having at least 80% sequence identity to the base sequence of the polynucleotide (NB1), and encoding a protein having *Tobamovirus* resistance control activity;

(NB4) a polynucleotide consisting of a base sequence complementary to a polynucleotide that hybridizes to a polynucleotide consisting of the base sequence of the polynucleotide (NB1) under stringent conditions, and encoding a protein having *Tobamovirus* resistance control activity;

(NB5) a polynucleotide encoding a protein consisting of an amino acid sequence of SEQ ID NO: 6;

(NB6) a polynucleotide consisting of an amino acid sequence obtained by deletion, substitution, insertion, and/or addition of one or several amino acids in the amino acid sequence of SEQ ID NO: 6, and encoding a protein having *Tobamovirus* resistance control activity; and (NB7) a polynucleotide consisting of an amino acid sequence having at least 80% sequence identity to the amino acid sequence of SEQ ID NO: 6, and encoding a protein having *Tobamovirus* resistance control activity.

In the polynucleotides (NB2) to (NB4) and (NB6) to (NB7), "having *Tobamovirus* resistance control activity" means, for example, having *Tobamovirus* resistance control activity equivalent to (not significantly different from) that of the polynucleotide (NB1) or (NB5).

In the polynucleotide (NB1), the base sequence of SEQ ID NO: 4 is a coding sequence of the polynucleotide (NB5). The base sequence of SEQ ID NO: 4 can be obtained, for example, from *S. lycopersicum* cv. Heinz 1706. In addition, in the polynucleotide (NB1), the base sequence of SEQ ID NO: 5 is a coding sequence of the polynucleotide (NB5). The base sequence of SEQ ID NO: 5 can be obtained, for example, from *S. lycopersicum* cv. Craigella GCR26.

In the polynucleotide (NB2), "one or several" bases may be, for example, in a range in which the protein encoded by the polynucleotide (NB2) has the *Tobamovirus* resistance control activity. The "one or several" bases in the polynucleotide (NB2) is, for example, 1 to 264, 1 to 262, 1 to 260, 1 to 198, 1 to 195, 1 to 132, 1 to 131, 1 to 130, 1 to 66, 1 to 65, 1 to 52, 1 to 39, 1 to 26, 1 to 13, 1 to 6, 1 to 3, 1 to 2, or 1 in the sequence of the polynucleotide (NB1).

In the polynucleotide (NB3), "sequence identity" may be, for example, in a range in which the protein encoded by the polynucleotide (NB3) has the *Tobamovirus* resistance control activity. The sequence identity of the polynucleotide (NB3) relative to the base sequence of the polynucleotide (NB1) is, for example, at least 80%, at least 85%, at least 90%, at least 95%, at least 96%, at least 97%, at least 98%, or at least 99%.

In the polynucleotide (NB4), "polynucleotide that hybridizes" is, for example, a polynucleotide that is completely or partially complementary to the polynucleotide (NB1). The hybridization can be detected, for example, by various hybridization assays. The hybridization assays are not particularly limited, and methods described, for example, in Sambrook et al., "Molecular Cloning: A Laboratory Manual 2$^{nd}$ Ed." [Cold Spring Harbor Laboratory Press (1989)] and the like may also be employed. In the polynucleotide (NB4), regarding the "stringent conditions", for example, reference can be made to the foregoing description.

The sequence of the polynucleotide (NB5) is not particularly limited as long as, for example, the protein encoded by the polynucleotide (NB5) has the *Tobamovirus* resistance control activity. The base sequence of the polynucleotide (NB5) can be designed, for example, by substituting with the corresponding codon based on the amino acid sequence of SEQ ID NO: 6.

In the polynucleotide (NB6), "one or several" bases may be, for example, in a range in which the protein encoded by the polynucleotide (NB6) has the *Tobamovirus* resistance control activity. The "one or several" bases in the polynucleotide (NB6) is, for example, 1 to 59, 1 to 58, 1 to 44, 1 to 43, 1 to 30, 1 to 29, 1 to 15, 1 to 14, 1 to 11, 1 to 8, 1 to 7, 1 to 6, 1 to 3, 1 to 2, or 1 in the amino acid sequence of SEQ ID NO: 6.

In the polynucleotide (NB7), "sequence identity" regarding an amino acid sequence may be, for example, in a range in which the protein encoded by the polynucleotide (NB7) has the *Tobamovirus* resistance control activity. The sequence identity of the polynucleotide (NB7) relative to the amino acid sequence of SEQ ID NO: 6 is, for example, at least 80%, at least 85%, at least 90%, at least 95%, at least 96%, at least 97%, at least 98%, or at least 99%.

The SlTOM1c gene can also be referred to as LeTH3. Examples of the SlTOM1c gene include a polynucleotide consisting of a base sequence (SEQ ID NO: 7) registered under Accession No.: Solyc02g080370 in the Solyc and a polynucleotide consisting of a base sequence (SEQ ID NO: 8) registered under Accession No.: AB193043 in the Genbank. Examples of the protein encoded by the SlTOM1c gene include a polypeptide consisting of an amino acid sequence (SEQ ID NO: 9) registered under Accession No.: Solyc02g080370 in the Solyc and a polynucleotide consisting of a base sequence (SEQ ID NO: 9) registered under Accession No.: AB193043 in the Genbank.

cDNA base sequence of SlTOM1c gene (SEQ ID NO: 7,
Solyc02g080370):
5'-TGCTAATGAACTTGAATACTTACAGTTATCTTAATTGTTTGTATTAGG

AAGCATCAGTTTTTTGACTTCTTTCAATACAACAAGATAAGCGGAGGGGAG

AGCTGAAATGGCTAGGTTGCCACTTGGGTCGTCGCCGATTGACATCGCCGG

TCCGGTGACCAACTGGTGGGACCACGTCAACGAATCCGTTCAGTGGCAAGA

TGGGATTTTCTACTCCCTTTGTGCTTCCTATGGTCTTGTTTCAGCAGTTGC

CCTAATTCAATTAATACGAATTGATTTGAGGGTACCCGAGTATGGCTGGAC

AACACAAAAGGTGTTCCATCTGATGAACTTTGTTGTAAATGGAGTTCGTGC

AATTGTCTTTGGATTTCACAAACATGTTTTTCTGCTCCATTATAAGGTGCT

GACTCTGGCAATATTGGACCTACCAGGGCTCCTTTTCTTTTCAACATTCAC

ACTCCTTGTTCTATTTTGGGCTGAGATATATCACCAGGCTAGGAGTTTACC

AACAGATAAGCTCAGGATTTCTTATATTGCCATTAATGATGCCATATACTT

CATTCAGGCCTGTATCTGGGTTTACCTCTGGATCAATGACAATAGCACAGT

GGAATTCATTGGGAAGATATTTATGGCAGTTGTATCAGTTATTGCAGCCTT

GGGCTTTCTGCTATATGGTGGAAGGTTATTTCTCATGCTGCGGCGCTTCCC

TATTGAATCTAAAGGGAGGAGAAAGAAGCTTCATGAGGTTGGATCGGTGAC

TGCCATATGTTTCACCTGTTTCCTCATTAGATGCTTTGTGGTTGTGTTATC

TGCTTTTGATTCTGACGCATCTCTTGACGTCTTGGATCATCCTGTTTTGAA

TCTGATATACTACCTGCTGGTAGAAATTCTTCCTTCAGCTCTTGTGCTGTA

-continued
CATCCTGCGAAAACTGCCTCCAAAAGAGTGTCTGCACAATACCACCCAAT

CAGTTAGCTGCAGCAGAATTTTATCGTTAGTGATACACGTTCCCATGGTTT

CTGTTGCAGAAGCTAACTGGAGTTGTTCAGGAAAAGTGAAACTGCAAAAGG

ATATTCGGTTGCAATAATTCTGCGGAAAGGCAAAGATTCAACGCTTTTTTG

GCAGTTGTTAAAACAGAGGTTAAGCTGTTTTGCTTACATTATATTGTTTCT

GTGGTTTTAGTGTGAAGCATGAGACAAATAAGTGTTCCCCACGTCTGTGAA

AAATCCTAGTCATGATGTAATGACGCAGAGGGTAAATCTCAGTATCGCCAT

TGTACTGGCATGTTGTAACTATGATGTTCTGGATCTCCTTTACTGCAATGA

CTGATGTCCTTTGTTTGGTCA-3' cDNA base sequence of SlTOM1c gene (SEQ ID NO: 8,
AB193043):
5'-ACAACAAGATAAGCGGAGGGGAGAGCTGAAATGGCTAGGTTGCCACTT

GGGTCGTCGCCGATTGACATCGCCGGTCCGGTGACCAACTGGTGGGACCAC

GTCAACGAATCCGTTCAGTGGCAAGATGGGATTTTCTACTCCCTTTGTGCT

TCCTATGGTCTTGTTTCAGCAGTTGCCCTAATTCAATTAATACGAATTGAT

TTGAGGGTACCCGAGTATGGCTGGACAACACAAAAGGTGTTCCATCTGATG

AACTTTGTTGTAAATGGAGTTCGTGCAATTGTCTTTGGATTTCACAAACAT

GTTTTTCTGCTCCATTATAAGGTGCTGACTCTGGCAATATTGGACCTACCA

GGGCTCCTTTTCTTTTCAACATTCACACTCCTTGTTCTATTTTGGGCTGAG

ATATATCACCAGGCTAGGAGTTTACCAACAGATAAGCTCAGGATTTCTTAT

ATTGCCATTAATGATGCCATATACTTCATTCAGGCCTGTATCTGGGTTTAC

CTCTGGATCAATGACAATAGCACAGTGGAATTCATTGGGAAGATATTTATG

GCAGTTGTATCAGTTATTGCAGCCTTGGGCTTTCTGCTATATGGTGGAAGG

TTATTTCTCATGCTGCGGCGCTTCCCTATTGAATCTAAAGGGAGGAGAAAG

AAGCTTCATGAGGTTGGATCGGTGACTGCCATATGTTTCACCTGTTTCCTC

ATTAGATGCTTTGTGGTTGTGTTATCTGCTTTTGATTCTGACGCATCTCTT

GACGTCTTGGATCATCCTGTTTTGAATCTGATATACTACCTGCTGGTAGAA

ATTCTTCCTTCAGCTCTTGTGCTGTACATCCTGCGAAAACTGCCTCCAAAA

AGAGTGTCTGCACAATACCACCCAATCAGTTAGCTGCAGCAGAATTTTATC

GTTAGTGATACACGTTCCCATGGTTTCTGTTGCAGAAGCTAACTGGAGTTG

TTCAGGAAAAGTGAAACTGCAAAAGGATATTCGGTTGCAATAATTCTGCGG

AAAGGCAAAGATTCAACGCTTTTTTGGCAGTTGTTAAAACAGAGGTTAAGC

TGTTTTGCTTACATTATATTGTTTCTGTGGTTTTAGTGTGAAGCATGAGAC

AAATAAGTGTTCCCCACGTCTGTGAAAAATCCTAGTCATGATGTAATGACG

CAGAGGGTAAATCTCAGTATCGCCATTGTACTGGCATGTTGTAACTATGAT

GTTCTGGATCTCCTTTACTGCAATGACTGATGTCCTTTGTTTGGTCAAAAA

AAAAAA-3'

Protein encoded by SlTOM1c gene (SEQ ID NO: 9,
Solyc02g080370, AB193043):
MARLPLGSSPIDIAGPVTNWWDHVNESVQWQDGIFYSLCASYGLVSAVALI

QLIRIDLRVPEYGWTTQKVFHLMNFVVNGVRAIVFGFHKHVFLLHYKVLTL

AILDLPGLLFFSTFTLLVLFWAEIYHQARSLPTDKLRISYIAINDAIYFIQ

ACIWVYLWINDNSTVEFIGKIFMAVVSVIAALGFLLYGGRLFLMLRRFPIE

-continued

```
SKGRRKKLHEVGSVTAICFTCFLIRCFVVVLSAFDSDASLDVLDHPVLNLI

YYLLVEILPSALVLYILRKLPPKRVSAQYHPIS
```

As a specific example, the SlTOM1c gene is, for example, a *Tobamovirus* resistance control gene including the following polynucleotide (NC):

(NC) any of the following polynucleotides (NC1) to (NC7):

(NC1) a polynucleotide consisting of a base sequence of SEQ ID NO:7 or 8;

(NC2) a polynucleotide consisting of a base sequence obtained by deletion, substitution, insertion, and/or addition of one or several bases in a base sequence of the polynucleotide (NC1), and encoding a protein having *Tobamovirus* resistance control activity;

(NC3) a polynucleotide consisting of a base sequence having at least 80% sequence identity to the base sequence of the polynucleotide (NC1), and encoding a protein having *Tobamovirus* resistance control activity;

(NC4) a polynucleotide consisting of a base sequence complementary to a polynucleotide that hybridizes to a polynucleotide consisting of the base sequence of the polynucleotide (NC1) under stringent conditions, and encoding a protein having *Tobamovirus* resistance control activity;

(NC5) a polynucleotide encoding a protein consisting of an amino acid sequence of SEQ ID NO: 9;

(NC6) a polynucleotide consisting of an amino acid sequence obtained by deletion, substitution, insertion, and/or addition of one or several amino acids in the amino acid sequence of SEQ ID NO: 9, and encoding a protein having *Tobamovirus* resistance control activity; and (NC7) a polynucleotide consisting of an amino acid sequence having at least 80% sequence identity to an amino acid sequence of SEQ ID NO: 9, and encoding a protein having *Tobamovirus* resistance control activity.

In the polynucleotides (NC2) to (NC4) and (NC6) to (NC7), "having *Tobamovirus* resistance control activity" means, for example, having *Tobamovirus* resistance control activity equivalent to (not significantly different from) that of the polynucleotide (NC1) or (NC5).

In the polynucleotide (NC1), the base sequence of SEQ ID NO: 7 is a coding sequence of the polynucleotide (NC5). The base sequence of SEQ ID NO: 7 can be obtained, for example, from *S. lycopersicum* cv. Heinz 1706. In addition, in the polynucleotide (NC1), the base sequence of SEQ ID NO: 8 is a coding sequence of the polynucleotide (NC5). The base sequence of SEQ ID NO: 8 can be obtained, for example, from *S. lycopersicum* cv. Craigella GCR26.

In the polynucleotide (NC2), "one or several" bases may be, for example, in a range in which the protein encoded by the polynucleotide (NC2) has the *Tobamovirus* resistance control activity. The "one or several" bases in the polynucleotide (NC2) is, for example, 1 to 268, 1 to 264, 1 to 254, 1 to 201, 1 to 198, 1 to 190, 1 to 134, 1 to 132, 1 to 127, 1 to 67, 1 to 66, 1 to 63, 1 to 53, 1 to 52, 1 to 50, 1 to 40, 1 to 39, 1 to 38, 1 to 26, 1 to 25, 1 to 13, 1 to 12, 1 to 6, 1 to 3, 1 to 2, or 1 in the sequence of the polynucleotide (NC1).

In the polynucleotide (NC3), "sequence identity" may be, for example, in a range in which the protein encoded by the polynucleotide (NC3) has the *Tobamovirus* resistance control activity. The sequence identity of the polynucleotide (NC3) relative to the base sequence of the polynucleotide (NC1) is, for example, at least 80%, at least 85%, at least 90%, at least 95%, at least 96%, at least 97%, at least 98%, or at least 99%.

In the polynucleotide (NC4), "polynucleotide that hybridizes" is, for example, a polynucleotide that is completely or partially complementary to the polynucleotide (NC1). The hybridization can be detected, for example, by various hybridization assays. The hybridization assays are not particularly limited and, methods described, for example, in Sambrook et al., "Molecular Cloning: A Laboratory Manual $2^{nd}$ Ed." [Cold Spring Harbor Laboratory Press (1989)] and the like may also be employed. In the polynucleotide (NC4), regarding the "stringent conditions", for example, reference can be made to the foregoing description.

The sequence of the polynucleotide (NC5) is not particularly limited as long as, for example, the protein encoded by the polynucleotide (NC5) has the *Tobamovirus* resistance control activity. The base sequence of the polynucleotide (NC5) can be designed, for example, by substituting with the corresponding codon based on the amino acid sequence of SEQ ID NO: 9.

In the polynucleotide (NC6), "one or several" bases regarding an amino acid sequence may be, for example, in a range in which the protein encoded by the polynucleotide (NC6) has the *Tobamovirus* resistance control activity. The "one or several" bases in the polynucleotide (NC6) is, for example, 1 to 59, 1 to 56, 1 to 44, 1 to 42, 1 to 30, 1 to 28, 1 to 15, 1 to 14, 1 to 11, 1 to 8, 1 to 6, 1 to 5, 1 to 3, 1 to 2, or 1 in the amino acid sequence of SEQ ID NO: 9.

In the polynucleotide (NC7), "sequence identity" regarding an amino acid sequence may be, for example, in a range in which the protein encoded by the polynucleotide (NC7) has the *Tobamovirus* resistance control activity. The sequence identity of the polynucleotide (NC7) relative to the amino acid sequence of SEQ ID NO: 9 is, for example, at least 80%, at least 85%, at least 90%, at least 95%, at least 96%, at least 97%, at least 98%, or at least 99%.

The SlTOM1d gene may be, for example, a polynucleotide consisting of a base sequence (SEQ ID NO: 10) registered under Accession No.: Solyc01g007900 in the Solyc. The protein encoded by the SlTOM1d gene may be, for example, a polypeptide consisting of an amino acid sequence (SEQ ID NO: 11) registered under Accession No.: Solyc01g007900 in the Solyc.

```
cDNA base sequence of S1TOM1d gene (SEQ ID NO: 10,
Solyc01g007900):
5'-CTGAAAAAGGTAGTTGCCGATTTTGGTGTTTGATTTTTTTTTGGGGGG

ATTTTGAAATTGGTGAGTTTGATTTTGGAATCTCCGGTGATGGGACGGGCG

GAGATGGTTGTAGGCCCGTCGGAGAAGGTGGCGGTGGTGGCATATCATCTG

AATGATGCAATCAATTGGTGGGACGATGTGAACAGATCTCTTGATTGGCAA

AACCGTATATTCCATGTCCTTGCTGTTCTCTACGGCGTTGTCGCCGTCGTT

GCTCTTGTACAATTAATTCGCATTCAAATGAGAGTTCCTGAATATGGCTGG

ACCACTCAAAAAGTCTTCCACTTTCTCAATTTCTTTGTGAATGGAGTTCGC

TCGCTAGTTTTTACATTTCGTCGGGATGTTCAGAAGTTGCACCCGGAGATT

GTGCAACATATTATGCTTGATATGCCAAGTCTTGCATTCTTCACAACTTAT

GCTCTGCTAGTATTATTCTGGGCTGAGATATACTACCAGGCACGTGCTGTG

TCCACGGATGGGCTTAGACCTAGTTTCTTCACAATCAACGGAGTGGTTTAT

GCTATTCAGATTATATTATGGCTGATAATGTGGTGGAAACCTATTCGAGTA
```

-continued

```
CTCTTCATCTTATCCAAGATGTTTTTTGCAGGTGTATCCCTATTTGCAGCA

TTGGGATTTCTCCTCTACGGTGGAAGGCTTTTTCTTATGTTACAGCGGTTT

CCAGTAGAATCAAGAGGGAGACGCAAGAAGCTGCAGGAGGTTGGTTATGTC

ACGACAATATGTTTTTCATGCTTCCTCATTAGATGCGTTATGATGTGCTTC

AATGCATTTGATAAAGCTGCAGATCTTGATGTTTTGTATCATCCTATTTTG

AATTTGATATATTACCTGTTAGTGGAGATACTGCCTTCTTCTCTTGTCCTT

TTTATTTTAAGGAAGTTGCCTCCAAAGCGAGGGATCACACAATACCACCCT

ATTCACTAATACATTAAGAGGGTAGATAATGATGAAAATCAGGCTCCGGGA

TCAGGTATTAAGTAAGTTGGCTTTTACCTGGATGTGATTTGCAAGCAAGAA

ATACGAGAGGAGTGATAATGTAAATTGAAGTATGGTTCGTCTATACTGAAA

TATCCGTCTGTCCTCACACTAGGCAGATTGTAGCTCTGTTTTGTACCACTA

GTTATAGATGGAATTGTGAAGTATCTTACGACCTTTAGTGTATTATTTCGC

CTTTGTATGTGTCAGATTTCAATTGAATTC-3'
```

Protein encoded by SlTOM1d gene (SEQ ID NO: 11, Solyc01g007900):
```
MGRAEMVVGPSEKVAVVAYHLNDAINWWDDVNRSLDWQNRIFHVLAVLYGV

VAVVALVQLIRIQMRVPEYGWTTQKVFHFLNFFVNGVRSLVFTFRRDVQKL

HPEIVQHIMLDMPSLAFFTTYALLVLFWAEIYYQARAVSTDGLRPSFFTIN

GVVYAIQIILWLIMWWKPIRVLFILSKMFFAGVSLFAALGFLLYGGRLFLM

LQRFPVESRGRRKKLQEVGYVTTICFSCFLIRCVMMCFNAFDKAADLDVLY

HPILNLIYYLLVEILPSSLVLFILRKLPPKRGITQYHPIH
```

As a specific example, the SlTOM1d gene is, for example, a *Tobamovirus* resistance control gene including the following polynucleotide (ND):

(ND) any of the following polynucleotides (ND1) to (ND7):

(ND1) a polynucleotide consisting of a base sequence of SEQ ID NO: 10;

(ND2) a polynucleotide consisting of a base sequence obtained by deletion, substitution, insertion, and/or addition of one or several bases in a base sequence of the polynucleotide (ND1), and encoding a protein having *Tobamovirus* resistance control activity;

(ND3) a polynucleotide consisting of a base sequence having at least 80% sequence identity to the base sequence of the polynucleotide (ND1), and encoding a protein having *Tobamovirus* resistance control activity;

(ND4) a polynucleotide consisting of a base sequence complementary to a polynucleotide that hybridizes to a polynucleotide consisting of the base sequence of the polynucleotide (ND1) under stringent conditions, and encoding a protein having *Tobamovirus* resistance control activity;

(ND5) a polynucleotide encoding a protein consisting of an amino acid sequence of SEQ ID NO: 11;

(ND6) a polynucleotide consisting of an amino acid sequence obtained by deletion, substitution, insertion, and/or addition of one or several amino acids in the amino acid sequence of SEQ ID NO: 11, and encoding a protein having *Tobamovirus* resistance control activity; and (ND7) a polynucleotide consisting of an amino acid sequence having at least 80% sequence identity to the amino acid sequence of SEQ ID NO: 11, and encoding a protein having *Tobamovirus* resistance control activity.

In the polynucleotides (ND2) to (ND4) and (ND6) to (ND7), "having *Tobamovirus* resistance control activity" means, for example, having *Tobamovirus* resistance control activity equivalent to (not significantly different from) that of the polynucleotide (ND1) or (ND5).

In the polynucleotide (ND1), the base sequence of SEQ ID NO: 10 is a coding sequence of the polynucleotide (ND5). The base sequence of SEQ ID NO: 10 can be obtained, for example, from *S. lycopersicum* cv. Heinz 1706.

In the polynucleotide (ND2), "one or several" bases may be, for example, in a range in which the protein encoded by the polynucleotide (ND2) has the *Tobamovirus* resistance control activity. The "one or several" bases in the polynucleotide (ND2) is, for example, 1 to 264, 1 to 250, 1 to 198, 1 to 187, 1 to 132, 1 to 125, 1 to 66, 1 to 62, 1 to 52, 1 to 50, 1 to 39, 1 to 37, 1 to 26, 1 to 25, 1 to 13, 1 to 12, 1 to 6, 1 to 3, 1 to 2, or 1 in the sequence of the polynucleotide (ND1).

In the polynucleotide (ND3), "sequence identity" may be, for example, in a range in which the protein encoded by the polynucleotide (ND3) has the *Tobamovirus* resistance control activity. The sequence identity of the polynucleotide (ND3) relative to the base sequence of the polynucleotide (ND1) is, for example, at least 80%, at least 85%, at least 90%, at least 95%, at least 96%, at least 97%, at least 98%, or at least 99%.

In the polynucleotide (ND4), "polynucleotide that hybridizes" is, for example, a polynucleotide that is completely or partially complementary to the polynucleotide (ND1). The hybridization can be detected, for example, by various hybridization assays. The hybridization assays are not particularly limited, and methods described, for example, in Sambrook et al., "Molecular Cloning: A Laboratory Manual 2nd Ed." [Cold Spring Harbor Laboratory Press (1989)] and the like may also be employed. In the polynucleotide (ND4), regarding "stringent conditions", for example, reference can be made to the foregoing description.

The sequence of the polynucleotide (ND5) is not particularly limited as long as, for example, the protein encoded by the polynucleotide (ND5) has the *Tobamovirus* resistance control activity. The base sequence of the polynucleotide (ND5) can be designed, for example, by substituting with the corresponding codon based on the amino acid sequence of SEQ ID NO: 11.

In the polynucleotide (ND6), "one or several" bases regarding an amino acid sequence may be, for example, in a range in which the protein encoded by the polynucleotide (ND6) has the *Tobamovirus* resistance control activity. The "one or several" bases in the polynucleotide (ND6) is, for example, 1 to 59, 1 to 58, 1 to 44, 1 to 43, 1 to 30, 1 to 29, 1 to 15, 1 to 14, 1 to 11, 1 to 8, 1 to 6, 1 to 5, 1 to 3, 1 to 2, or 1 in the amino acid sequence of SEQ ID NO: 11.

In the polynucleotide (ND7), "sequence identity" regarding an amino acid sequence may be, for example, in a range in which the protein encoded by the polynucleotide (ND7) has the *Tobamovirus* resistance control activity. The sequence identity of the polynucleotide (ND7) relative to the amino acid sequence of SEQ ID NO: 11 is, for example, at least 80%, at least 85%, at least 90%, at least 95%, at least 96%, at least 97%, at least 98%, or at least 99%.

In the present invention, "loss of function" means, for example, a state in which the inherent function of the gene is (significantly) decreased or lost. That is, in the present invention, "loss-of-function mutation" may be used in the meaning of either a mutation in which the inherent function of the gene is (significantly) attenuated, or a mutation causing complete loss of function. The "mutation causing complete loss of function" can also be referred to, for example, as a null mutation or an amorph.

The loss of function for each of the genes in the SlTOM1 gene group means, for example, a state of a tomato plant having the loss-of-function genes in which the functions of the genes are (significantly) decreased or lost to such an extent that the tomato plant is resistant to *Tobamovirus* as compared with a tomato plant having a normal SlTOM1a gene, a normal SlTOM1b gene, a normal SlTOM1c gene, and a normal SlTOM1d gene (hereinafter also referred to as a "wild-type tomato plant"). The loss of function of the gene may specifically mean, for example, a state in which the expression level of the mRNA of the gene or the protein encoded by the gene is (significantly) decreased, a state in which the mRNA of the gene or the protein encoded by the gene is not expressed at all, a state in which the expression level of the mRNA of the functional gene or the protein encoded by the functional gene is decreased, or a state in which the mRNA of the functional gene or the protein encoded by the functional gene is not expressed at all. Therefore, the loss of function for each of the genes in the SlTOM1 gene group may be carried out by introducing a loss-of-function mutation into each of the genes, or may be carried out by introducing a polynucleotide suppressing expression of each of the genes. The "suppressing expression of each of the genes" may be suppressing transcription of a gene or suppressing translation into a protein.

In the present invention, the resistant tomato plant with loss of function for a SlTOM1a gene, a SlTOM1c gene, and a SlTOM1d gene includes, for example, a loss-of-function gene for a SlTOM1a gene, a loss-of-function gene for a SlTOM1c gene, and a loss-of-function gene for a SlTOM1d gene. The resistant tomato plant may include a loss-of-function gene for a SlTOM1b gene for further improving the resistance to *Tobamovirus*. The present invention is not limited thereto, and the resistant tomato plant of the present invention may include at least one loss-of-function gene selected from the group consisting of, for example, a loss-of-function gene for a SlTOM1a gene, a loss-of-function gene for a SlTOM1b gene, a loss-of-function gene for a SlTOM1c gene, and a loss-of-function gene for a SlTOM1d gene. That is, the resistant tomato plant of the present invention may be with loss of function for at least one selected from the group consisting of a SlTOM1a gene, a SlTOM1b gene, a SlTOM1c gene, and a SlTOM1d gene, for example. The resistant tomato plant of the present invention may include at least one loss-of-function gene selected from the group consisting of a loss-of-function gene for a SlTOM1d gene, a loss-of-function gene for a SlTOM1a gene, a loss-of-function gene for a SlTOM1b gene, and a loss-of-function gene for a SlTOM1c gene.

The loss of function of each of the genes in the SlTOM1 gene group can be caused, for example, by introducing a mutation, more specifically, a loss-of-function mutation into a SlTOM1a gene, a SlTOM1b gene, a SlTOM1c gene, and/or a SlTOM1d gene. The types of the mutation are not particularly limited, and examples thereof include point mutation, missense mutation, nonsense mutation, frameshift mutation, and large deletion of bases in a wide range. The mutation may, for example, result in the deletion of part or whole of each of the genes. The frameshift mutation is a mutation that occurs when a base deletion or insertion is caused and the triplet reading frame (codon) is misaligned. The frameshift mutation has a much greater influence on gene function as compared to the base pair substitution mutation. This is because, when the frameshift mutation occurs, the genetic code after the point where the frameshift mutation is introduced in the gene is greatly shifted, and not only the amino acid is changed, but also the stop codon and the like are shifted.

The loss-of-function gene for each of the genes is, for example, a gene into which a mutation is introduced by insertion, deletion, and/or substitution of one or several bases (hereinafter also referred to as "one or more bases") in the base sequence of a normal gene of each of the genes in the SlTOM1 gene group. As a specific example, the loss-of-function gene for the SlTOM1a gene is, for example, a gene obtained by introducing a mutation by insertion, deletion, and/or substitution of one or more bases in the base sequence of the normal gene of the SlTOM1a gene. In the loss-of-function gene for the SlTOM1a gene, regarding "one or more bases", for example, reference can be made to the description as to the number of bases in the polynucleotide (NA2). The loss-of-function gene for the SlTOM1b gene is, for example, a gene obtained by introducing a mutation by insertion, deletion, and/or substitution of one or more bases in the base sequence of a normal gene of the SlTOM1b gene. In the loss-of-function gene for the SlTOM1b gene, regarding "one or more bases", for example, reference can be made to the description as to the number of bases in the polynucleotide (NB2). The loss-of-function gene for the SlTOM1c gene is, for example, a gene obtained by introducing a mutation by insertion, deletion, and/or substitution of one or more bases in the base sequence of a normal gene of the SlTOM1c gene. In the loss-of-function gene for the SlTOM1c gene, regarding "one or more bases", for example, reference can be made to the description as to the number of bases in the polynucleotide (NC2). The loss-of-function gene for the SlTOM1d gene is, for example, a gene obtained by introducing a mutation by insertion, deletion, and/or substitution of one or more bases in the base sequence of a normal gene of the SlTOM1d gene. In the loss-of-function gene for the SlTOM1d gene, regarding "one or more bases", for example, reference can be made to the description as to the number of bases in the polynucleotide (ND2). The frameshift mutation occurs, for example, by insertion or deletion of $3m+1$ bases or $3m+2$ bases ($m$ is an integer of 0 or more).

In the present invention, mutation to each of the genes in the SlTOM1 gene group can be caused, for example, by introducing a mutation into a target gene in a genome of a target tomato plant in a conventional manner. Examples of the mutation introduction method include homologous recombination; and a genome editing technique using ZFN, TALEN, CRISPR-CAS9, CRISPR-CPF1, and the like. The mutation may be introduced by, for example, mutagenesis such as site-directed mutagenesis. The mutation may be introduced by, for example, random mutagenesis. Examples of the random mutagenesis include radiation treatment with α-ray, β-ray, γ-ray, X-ray, or the like; chemical treatment with a mutagen such as ethyl methanesulfonate (EMS), ethinyl nitrosourea (ENU), or the like; and heavy ion beam treatment. Regarding the mutation introduction method using the genome editing technique, for example, reference can be made to Example 1 to be described below. Specifically, introduction of mutation using the genome editing technique can be performed, for example, by introducing proteins and nucleic acids constituting the genome editing technique, or vectors encoding them. The protein may be, for example, Clustered Regularly Interspaced Short Palindromic Repeats (CRISPR) enzyme, and specific examples thereof include Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4. The nucleic acid may be, for example, crRNA and tracrRNA, or a single-stranded nucleic acid to which crRNA and tracrRNA are linked via a linker. In this case, the nucleic acid is obtained by designing a base sequence annealing with the target sequence in crRNA so as to be complementary to a base sequence encoding each of the genes. One kind of the nucleic acids may be used alone, or two or more of them may be used in combination. The mutation may be introduced by, for example, mutagenesis such as site-directed mutagenesis.

The position of the mutation in the loss-of-function gene for each of the genes in the SlTOM1 gene group is not particularly limited, and may be any region related to each of the genes. Specific examples of the position of the mutation in the loss-of-function gene for each of the genes in the SlTOM1 gene group include an expression control region such as a promoter region of each of the genes, a transmembrane region of a protein encoded by each of the genes, an exon region including an encoding region encoding a protein encoded by each of the genes such as a ligand-binding region, and a non-encoding region not encoding a protein encoded by each of the genes (for example, an intron region, an enhancer region, or the like), and the exon region is preferred.

As a specific example, when the gene in the SlTOM1 gene group is the SlTOM1a gene, it is preferable that the position of the mutation include 1st to 514th bases, preferably 167th to 514th bases in the base sequence of SEQ ID NO: 1, or 1st to 507th bases, preferably 160th to 507th bases in the base sequence of SEQ ID NO: 2. When the gene in the SlTOM1 gene group is the SlTOM1b gene, it is preferable that the position of the mutation include 1st to 224th bases, preferably 156th to 224th bases in the base sequence of SEQ ID NO: 4, or 1st to 224th bases, preferably 156th to 224th bases in the base sequence of SEQ ID NO: 5. When the gene in the SlTOM1 gene group is the SlTOM1c gene, it is preferable that the position of the mutation include 1st to 149th bases, preferably 107th to 149th bases in the base sequence of SEQ ID NO: 7, or 1st to 73th bases, preferably 31st to 73rd bases in the base sequence of SEQ ID NO: 8. When the gene in the SlTOM1 gene group is the SlTOM1d gene, it is preferable that the position of the mutation include 1st to 437th bases and 88th to 437th bases in the base sequence of SEQ ID NO: 10. The mutations to be introduced into these mutation positions are preferably nonsense mutations or frameshift mutations.

The loss-of-function gene for the SlTOM1a gene is, for example, a gene including the following polynucleotide (MA):

(MA) any of the following polynucleotides (MA1) to (MA5);

(MA1) a polynucleotide consisting of a base sequence obtained by deletion, substitution, insertion, and/or addition of one or several bases in the base sequence of the polynucleotide (NA1);

(MA2) a polynucleotide consisting of a base sequence having at least 80% sequence identity to the base sequence of the polynucleotide (NA1);

(MA3) a polynucleotide consisting of a base sequence complementary to a polynucleotide that hybridizes to a polynucleotide consisting of the base sequence of the polynucleotide (NA1) under stringent conditions;

(MA4) a polynucleotide encoding a protein consisting of an amino acid sequence obtained by deletion, substitution, insertion, and/or addition of one or several amino acids in an amino acid sequence of SEQ ID NO: 3; and (MA5) a polynucleotide encoding a protein consisting of an amino acid sequence having at least 80% sequence identity to the amino acid sequence of SEQ ID NO: 3.

It is preferable that the polynucleotides (MA1) to (MA5) be polynucleotides encoding proteins having no *Tobamovirus* resistance control activity.

In the polynucleotides (MA1) to (MA5), "having no *Tobamovirus* resistance control activity" means, for example, that the *Tobamovirus* resistance control activity is significantly suppressed as compared to a protein encoded by the polynucleotide (NA1) or (NA5), and preferably means that the *Tobamovirus* resistance control activity is completely lost.

The "one or several" bases in the polynucleotide (MA1) is, for example, 1 to 264, 1 to 198, 1 to 132, 1 to 66, 1 to 52, 1 to 39, 1 to 26, 1 to 13, 1 to 6, 1 to 3, 1 to 2, or 1 in the sequence of the polynucleotide (NA1).

The sequence identity of the polynucleotide (MA2) relative to the base sequence of the polynucleotide (NA1) is, for example, at least 80%, at least 85%, at least 90%, at least 95%, at least 96%, at least 97%, at least 98%, or at least 99%.

In the polynucleotide (MA3), "polynucleotide that hybridizes" is, for example, a polynucleotide that is completely or partially complementary to the polynucleotide (NA1). The hybridization can be detected, for example, by various hybridization assays. The hybridization assays are not particularly limited, and methods described, for example, in Sambrook et al., "Molecular Cloning: A Laboratory Manual $2^{nd}$ Ed." [Cold Spring Harbor Laboratory Press (1989)] and the like may also be employed. In the polynucleotide (MA3), regarding the "stringent conditions" reference can be made to the above description, for example.

The "one or several" bases in the polynucleotide (MA4) is, for example, 1 to 59, 1 to 44, 1 to 30, 1 to 15, 1 to 11, 1 to 8, 1 to 6, 1 to 3, 1 to 2, or 1 in the amino acid sequence of SEQ ID NO: 3.

The sequence identity of the polynucleotide (MA5) relative to the amino acid sequence of SEQ ID NO: 3 is, for example, at least 80%, at least 85%, at least 90%, at least 95%, at least 96%, at least 97%, at least 98%, or at least 99%.

As a specific example, the loss-of-function gene for a SlTOM1b gene is a gene including the following polynucleotide (MB):

(MB) any of the following polynucleotides (MB1) to (MB5);

(MB1) a polynucleotide consisting of a base sequence obtained by deletion, substitution, insertion, and/or addition of one or several bases in a base sequence of the polynucleotide (NB1);

(MB2) a polynucleotide consisting of a base sequence having at least 80% sequence identity to the base sequence of the polynucleotide (NB1);

(MB3) a polynucleotide consisting of a base sequence complementary to a polynucleotide that hybridizes to a polynucleotide consisting of the base sequence of the polynucleotide (NB1) under stringent conditions;

(MB4) a polynucleotide encoding a protein consisting of an amino acid sequence obtained by deletion, substitution, insertion, and/or addition of one or several amino acids in an amino acid sequence of SEQ ID NO: 6; and (MB5) a polynucleotide encoding a protein consisting of an amino acid sequence having at least 80% sequence identity to the amino acid sequence of SEQ ID NO: 6.

It is preferable that the polynucleotides (MB1) to (MB5) be polynucleotides encoding a protein having no *Tobamovirus* resistance control activity.

In the polynucleotides (MB1) to (MB5), "having no *Tobamovirus* resistance control activity" means, for example, that the *Tobamovirus* resistance control activity is significantly suppressed as compared to the protein encoded by the polynucleotide (NB1) or (NB5), and preferably means that the *Tobamovirus* resistance control activity is completely lost.

The "one or several" bases in the polynucleotide (MB1) is, for example, 1 to 264, 1 to 198, 1 to 132, 1 to 66, 1 to 52, 1 to 39, 1 to 26, 1 to 13, 1 to 6, 1 to 3, 1 to 2, or 1 in the sequence of the polynucleotide (NB1).

The sequence identity of the polynucleotide (MB2) relative to the base sequence of the polynucleotide (NB1) is, for example, at least 80%, at least 85%, at least 90%, at least 95%, at least 96%, at least 97%, at least 98%, or at least 99%.

In the polynucleotide (MB3), "polynucleotide that hybridizes" is, for example, a polynucleotide that is completely or partially complementary to the polynucleotide (NB1). The hybridization can be detected, for example, by various hybridization assays. The hybridization assays are not particularly limited, and methods described, for example, in Sambrook et al., "Molecular Cloning: A Laboratory Manual 2$^{nd}$ Ed." [Cold Spring Harbor Laboratory Press (1989)] and the like may also be employed. In the polynucleotide (MB3), regarding the "stringent conditions", reference can be made to the above description, for example.

The "one or several" bases in the polynucleotide (MB4) is, for example, 1 to 59, 1 to 44, 1 to 30, 1 to 15, 1 to 11, 1 to 8, 1 to 6, 1 to 3, 1 to 2, or 1 in the amino acid sequence of SEQ ID NO: 6.

The sequence identity of the polynucleotide (MB5) relative to the amino acid sequence of SEQ ID NO: 6 is, for example, at least 80%, at least 85%, at least 90%, at least 95%, at least 96%, at least 97%, at least 98%, or at least 99%.

As a specific example, the loss-of-function gene for a SITOM1c gene is a gene including the following polynucleotide (MC):

(MC) any of the following polynucleotides (MC1) to (MC5);

(MC1) a polynucleotide consisting of a base sequence obtained by deletion, substitution, insertion, and/or addition of one or several bases in the base sequence of the polynucleotide (NC1);

(MC2) a polynucleotide consisting of a base sequence having at least 80% sequence identity to the base sequence of the polynucleotide (NC1);

(MC3) a polynucleotide consisting of a base sequence complementary to a polynucleotide that hybridizes to a polynucleotide consisting of the base sequence of the polynucleotide (NC1) under stringent conditions;

(MC4) a polynucleotide encoding a protein consisting of an amino acid sequence obtained by deletion, substitution, insertion, and/or addition of one or several amino acids in an amino acid sequence of SEQ ID NO: 9; and (MC5) a polynucleotide encoding a protein consisting of an amino acid sequence having at least 80% sequence identity to the amino acid sequence of SEQ ID NO: 9.

It is preferable that the polynucleotides (MC1) to (MC5) be polynucleotides encoding a protein having no *Tobamovirus* resistance control activity.

In the polynucleotides (MC1) to (MC5), "having no *Tobamovirus* resistance control activity" means, for example, that the *Tobamovirus* resistance control activity is significantly suppressed as compared to the protein encoded by the polynucleotide (NC1) or (NC5), and preferably means that the *Tobamovirus* resistance control activity is completely lost.

The "one or several" bases in the polynucleotide (MC1) is, for example, 1 to 264, 1 to 198, 1 to 132, 1 to 66, 1 to 52, 1 to 39, 1 to 26, 1 to 13, 1 to 6, 1 to 3, 1 to 2, or 1 in the sequence of the polynucleotide (NC1).

The sequence identity of the polynucleotide (MC2) relative to the base sequence of the polynucleotide (NC1) is, for example, at least 80%, at least 85%, at least 90%, at least 95%, at least 96%, at least 97%, at least 98%, or at least 99%.

In the polynucleotide (MC3), "polynucleotide that hybridizes" is, for example, a polynucleotide that is completely or partially complementary to the polynucleotide (NC1). The hybridization can be detected, for example, by various hybridization assays. The hybridization assays are not particularly limited, and methods described, for example, in Sambrook et al., "Molecular Cloning: A Laboratory Manual 2$^{nd}$ Ed." [Cold Spring Harbor Laboratory Press (1989)] and the like may also be employed. In the polynucleotide (MC3), regarding the "stringent conditions", reference can be made to the above description, for example.

The "one or several" bases in the polynucleotide (MC4) is, for example, 1 to 59, 1 to 44, 1 to 30, 1 to 15, 1 to 11, 1 to 8, 1 to 6, 1 to 3, 1 to 2, or 1 in the amino acid sequence of SEQ ID NO: 9.

The sequence identity of the polynucleotide (MC5) relative to the amino acid sequence of SEQ ID NO: 9 is, for example, at least 80%, at least 85%, at least 90%, at least 95%, at least 96%, at least 97%, at least 98%, or at least 99%.

As a specific example, the loss-of-function gene for a SITOM1d gene is a gene including the following polynucleotide (MD):

(MD) any of the following polynucleotides (MD1) to (MD5);

(MD1) a polynucleotide consisting of a base sequence obtained by deletion, substitution, insertion, and/or addition of one or several bases in the base sequence of the polynucleotide (ND1);

(MD2) a polynucleotide consisting of a base sequence having at least 80% sequence identity to the base sequence of the polynucleotide (ND1);

(MD3) a polynucleotide consisting of a base sequence complementary to a polynucleotide that hybridizes to a polynucleotide consisting of the base sequence of the polynucleotide (ND1) under stringent conditions;

(MD4) a polynucleotide encoding a protein consisting of an amino acid sequence obtained by deletion, substitution, insertion, and/or addition of one or several amino acids in an amino acid sequence of SEQ ID NO: 11; and (MD5) a polynucleotide encoding a protein consisting of an amino acid sequence having at least 80% sequence identity to the amino acid sequence of SEQ ID NO: 11.

It is preferable that the polynucleotides (MD1) to (MD5) be polynucleotides encoding a protein having no *Tobamovirus* resistance control activity.

In the polynucleotides (MD1) to (MD5), "having no *Tobamovirus* resistance control activity" means, for example, that the *Tobamovirus* resistance control activity is significantly suppressed as compared to the protein encoded by the polynucleotide (ND1) or (ND5), and preferably means that the *Tobamovirus* resistance control activity is completely lost.

The "one or several" bases in the polynucleotide (MD1) is, for example, 1 to 264, 1 to 198, 1 to 132, 1 to 66, 1 to 52, 1 to 39, 1 to 26, 1 to 13, 1 to 6, 1 to 3, 1 to 2, or 1 in the sequence of the polynucleotide (ND1).

The sequence identity of the polynucleotide (MD2) relative to the base sequence of the polynucleotide (ND1) is, for example, at least 80%, at least 85%, at least 90%, at least 95%, at least 96%, at least 97%, at least 98%, or at least 99%.

In the polynucleotide (MD3), "polynucleotide that hybridizes" is, for example, a polynucleotide that is completely or partially complementary to the polynucleotide (ND1). The hybridization can be detected, for example, by various hybridization assays. The hybridization assays are not particularly limited, and methods described, for example, in Sambrook et al., "Molecular Cloning: A Laboratory Manual 2$^{nd}$ Ed." [Cold Spring Harbor Laboratory Press (1989)] and the like may also be employed. In the polynucleotide (MD3), regarding the "stringent conditions", reference can be made to the above description, for example.

The "one or several" bases in the polynucleotide (MD4) is, for example, 1 to 59, 1 to 44, 1 to 30, 1 to 15, 1 to 11, 1 to 8, 1 to 6, 1 to 3, 1 to 2, or 1 in the amino acid sequence of SEQ ID NO: 11.

The sequence identity of the polynucleotide (MD5) relative to the amino acid sequence of SEQ ID NO: 11 is, for example, at least 80%, at least 85%, at least 90%, at least 95%, at least 96%, at least 97%, at least 98%, or at least 99%.

In the present invention, the genotype of each of the genes can be any genotype as long as, for example, the resistant tomato plant of the present invention is resistant to *Tobamovirus*. The genotype of each of the genes may be, for example, a homozygous form of a normal gene, a heterozygous form of a normal gene and a loss-of-function gene, or a homozygous form of a loss-of-function gene. That is, the SITOM1a gene, the SITOM1b gene, the SITOM1c gene, and the SITOM1d gene may be, for example, a homozygous form of the normal gene, a heterozygous form of the normal gene and the loss-of-function gene, or a homozygous form of the loss-of-function gene to the extent that the resistant tomato plant is resistant to *Tobamovirus*.

The combination of the genotypes of each of the genes is not particularly limited, and examples of the combination are as follows.

SITOM1a gene (normal gene): A, loss-of-function gene of SITOM1a gene: a

SITOM1b gene (normal gene): B, loss-of-function gene of SITOM1b gene: b

SITOM1c gene (normal gene): C, loss-of-function gene of SITOM1c gene: c

SITOM1d gene (normal gene): D, loss-of-function gene of SITOM1d gene: d (Combination of Genotypes)

aaBBccdd, aaBbccdd, aabbccdd, aabbccDd, aaBbccDd, aaBBccDd (Preferred Combination)

aaBBccdd, aaBbccdd, aabbccdd, aabbccDd

In the present invention, in the case of causing the loss of function for each of the genes by suppressing the expression of the *Tobamovirus* resistance control gene, the loss of function for each of the genes can be carried out, for example, by introducing a polynucleotide which suppresses the expression of each of the genes into a target tomato plant. The method of introducing the polynucleotide is not particularly limited, and may be carried out by, for example, a method such as RNA interference, antisense RNA, genome editing technology, or the like. An expression cassette such as an expression vector containing the polynucleotide can be introduced into a target tomato plant by, for example, a polyethylene glycol method, an electroporation method, a method via *Agrobacterium*, a particle gun method, or the like. The target tomato plant may be any of, for example, plant cells, calluses, plant tissues, and plant individuals.

Examples of the genes whose expression is to be suppressed include a SITOM1a gene, a SITOM1c gene, and a SITOM1d gene. The gene whose expression is to be suppressed may include, for example, a SITOM1b gene. However, the present invention is not limited thereto, the gene whose expression is to be suppressed may be at least one selected from the group consisting of, for example, a SITOM1a gene, a SITOM1b gene, a SITOM1c gene, and a SITOM1d gene. The gene whose expression is to be suppressed may be at least one selected from the group consisting of, for example, a SITOM1d gene, a SITOM1a gene, a SITOM1b gene, and a SITOM1c gene.

In the resistant tomato plant of the present invention, a SITOM1a gene, a SITOM1c gene, and a SITOM1d gene lose function, but the present invention is not limited thereto, and at least one selected from the group consisting of a SITOM1a gene, a SITOM1b gene, a SITOM1c gene, and a SITOM1d gene may be lost in function. The gene whose function is lost may be at least one selected from the group consisting of, for example, a SITOM1d gene a SITOM1a gene, a SITOM1b gene, and a SITOM1c gene.

The resistant tomato plant of the present invention can be obtained by causing a loss-of-function mutation in the wild-type SITOM1 gene group, as described above. Thus, the resistant tomato plant of the present invention can also be referred to as, for example, "a mutant of a tomato plant resistant to *Tobamovirus*". The resistant tomato plant of the present invention may be a progeny line of "a mutant of a tomato plant resistant to *Tobamovirus*", and may be a tomato plant having a loss-of-function mutation in the SITOM1 gene group. The tomato plant of the present invention may also be referred to as a mutant of a tomato plant having a genetic mutation introduced into the base sequence of the SITOM1 gene group by the aforementioned mutation introduction method, for example. The resistant tomato plant of the present invention can also be referred to as a *Tobamovirus* resistant tomato plant, except for, for example, tomato plants obtained solely by means of an essentially biological process.

Regarding the method for producing the resistant tomato plant of the present invention, reference can be made to the descriptions as to the imparting method, the second production method, the screening method, and the third production method to be described below.

<First Production Method>

As described above, a method for producing a *Tobamovirus* resistant tomato plant of the present invention includes the following step (a):

(a) crossing the *Tobamovirus* resistant tomato plant according to the present invention with another tomato plant.

The first production method of the present invention is characterized in that the resistant tomato plant of the present invention is used in the step (a), and other steps and conditions are not particularly limited. According to the first production method of the present invention, tomato plants resistant to *Tobamovirus* can be produced. Regarding the first production method of the present invention, reference can be made to the description of the tomato plant of the present invention.

In the step (a), a plant used as a first parent is not limited as long as it is the resistant tomato plant of the present invention. As described above, the resistant tomato plant of the present invention can also be obtained, for example, by the imparting method, the second production method, the screening method, and the third production method of the present invention to be described below. For this reason, the first production method of the present invention may carry out any one or more of the imparting methods, the second production method, the screening method, and the third production method of the present invention prior to the step (a), for example. In this case, regarding these methods, reference can be made to the descriptions as to these methods to be described below.

As a specific example, the first production method of the present invention may include the following step (x) or step (y):

(x) selecting a *Tobamovirus* resistant tomato plant according to the present invention from one or more tomato plants to be examined (selecting); or (y) constructing a *Tobamovirus* resistant tomato plant of the present invention from one of more target tomato plants (producing).

In the step (x), selection of the *Tobamovirus* resistant tomato plant can be referred to as selection of a tomato plant with loss of function for a SITOM1a gene, a SITOM1c gene, and a SITOM1d gene. Thus, the step (x) can be performed, for example, by the following step (x1) and step (x2):

(x1) detecting whether or not a SITOM1a gene, a SITOM1c gene, and a SITOM1d gene of the tomato plant to be examined lose function; and (x2) selecting, if the SITOM1a gene, the SITOM1c gene, and the SITOM1d gene lose function, the tomato plant to be examined as a *Tobamovirus* resistant tomato plant.

When the step (x) includes the step (x1) and the step (x2), the step (x) may be performed, for example, using the base sequence or the expression level of each of the genes as an indicator.

When the base sequence of each of the genes is used as an indicator, in the step (x1), detection of the loss of function for each of the genes may be carried out, for example, by decoding the base sequence of each of the genes of the tomato plant to be examined and comparing it with the base sequence of the corresponding normal gene. The base sequence can be decoded using, for example, a sequencer. In the step (x2), for example, when the base sequence of each of the genes of the tomato plant to be examined is a base sequence obtained by introducing a loss-of-function mutation into the base sequence of the corresponding normal gene, the tomato plant is selected as a *Tobamovirus* resistant tomato plant. The conditions of the selection will be described below. Regarding the base sequence of the normal gene, reference can be made to the base sequence of each of the genes described above. Comparison of the base sequences can be carried out, for example, by analysis software of the base sequence (e.g., the aforementioned BLAST, and the like). In the step (x2), the region where the base sequences are compared may be an intron region of each of the genes or an exon region of each of the genes, but the latter is preferable. When the loss of function for each of the genes is caused by introducing a mutation by insertion, deletion, and/or substitution of one or more bases with respect to the base sequence of the corresponding normal gene, the step (x1) may be performed using, for example, a primer set, a probe, or a combination thereof capable of detecting at least one mutation. The primer set and probe can be designed using a known design method, for example, based on the type of the mutation.

In the step (x2), for example, when insertion, deletion, and/or substitution of one or more bases is done with respect to the normal gene of each of the genes, the gene may be determined to be a loss-of-function gene. In the step (x2), for example, when a frameshift mutation is introduced into the normal gene of each of the genes, the gene may be determined to be a loss-of-function gene. Further, in the step (x2), for example, when the normal gene of each of the genes is partially or completely deleted, the gene may be determined to be a loss-of-function gene.

In the step (x2), the selection may further be performed based on the genotype of each of the genes. As a specific example, in the step (x2), when the genotype of each of the genes corresponds to the combination of the genotypes described above, the plant may be selected as the *Tobamovirus* resistant tomato plant. As a specific example, in the step (x2), for example, when a tomato plant includes loss-of-function genes for a SITOM1a gene, a SITOM1c gene, and a SITOM1d gene in a homozygous form, the tomato plant to be examined may be selected as a *Tobamovirus* resistant tomato plant. In the step (x2), for example, when a tomato plant includes loss-of-function genes for a SITOM1a gene, a SITOM1b gene, a SITOM1c gene, and a SITOM1d gene in a homozygous form, the tomato plant to be examined may be selected as a *Tobamovirus* resistant tomato plant.

When the expression level of each of the genes is used as an indicator, in the step (x1), the loss of function for each of the genes may be detected by, for example, detecting the function of mRNA of each of the genes of the tomato plant to be examined or the function of a protein encoded by each of the genes. Further, in the step (x1), detection of the loss of function for each of the genes may be performed by detecting, for example, the presence or absence of expression of each of the genes or a protein encoded by each of the genes, or the expression level of each of the genes or a protein encoded by each of the genes in the tomato plant to be examined.

In the step (x), when selection is performed based on the expression of each of the genes or a protein encoded by each of the genes, in the step (x1), for example, the expression level of at least one of each of the genes and a protein encoded by each of the genes in the biological sample of the tomato plant to be examined is measured. Then, in the step (x2), based on the expression level of at least one of each of the genes and a protein encoded by each of the genes in the biological sample of the tomato plant to be examined and the reference value, a plant with loss of function for each of the genes is selected. More specifically, in the step (x2), selection of the plant with loss of function from one or more tomato plants to be examined can be carried out, for example, by comparing the expression level of at least one of each of the genes and the protein encoded by each of the genes in the biological sample of the tomato plant to be examined with the reference value.

The biological sample of the tomato plant to be examined is not particularly limited, and may be, for example, either a plant individual of the tomato plant to be examined or a part of the plant individual. The number of types of the biological sample used in the step (x1) may be, for example, one or two or more.

In the step (x1), the expression level of each of the genes can be measured by, for example, semi-quantitative PCR, quantitative PCR, Northern blotting, digital PCR, RNA sequence analysis (RNAseq), or the like. In addition, in the step (x1), the expression level of a protein encoded by each of the genes can be measured by, for example, a method using a spectrophotometer such as an ultraviolet absorption method or a bicinchoninic acid method, a protein quantitative method such as ELISA or Western blotting, or the like.

Examples of the reference value include the expression level of each of the genes or a protein encoded by each of the genes in the wild-type tomato plant and the expression level of each of the genes or a protein encoded by each of the genes in a plant with loss of function for a gene/genes corresponding to the target gene/genes (e.g., tomato plant with completely loss of a SlTOM1a gene, a SlTOM1b gene, a SlTOM1c gene, and/or a SlTOM1d gene). When the expression level of each of the genes in a plant with loss of function is used as the reference value, the plant with loss of function may be, for example, a plant with loss of function for one of two SlTOM1a genes, SlTOM1b genes, SlTOM1c genes, and/or SlTOM1d genes, which are respectively located on a pair of chromosomes, or may be a plant with loss of function for both of two SlTOM1a genes, SlTOM1b genes, SlTOM1c genes, and/or SlTOM1d genes. The expression level of each of the genes or a protein encoded by each of the genes used as the reference value can be obtained, for example, by measuring the expression level of each of the genes or a protein encoded by each of the genes in a biological sample collected under the same conditions as the biological sample of the tomato plant to be examined by the same method as the biological sample of the tomato plant to be examined. The reference value may be measured in advance or may be measured simultaneously with the biological sample of the tomato plant to be examined, for example.

In this case, in the step (x2), a method for evaluating whether or not each of the genes in the tomato plant to be examined has lost in function is not particularly limited, and can be appropriately determined depending on the type of the reference value. As a specific example, when the expression level of each of the genes in a biological sample of the tomato plant to be examined is lower than the expression level of the corresponding gene in a corresponding wild-type tomato plant, when the expression level of each of the genes in a biological sample of the tomato plant to be examined is the same as (not significantly different from) the expression level of the gene in a plant with loss of function for each of the genes, and/or the expression level of each of the genes in a biological sample of the tomato plant to be examined is lower than the expression level of the gene in a plant with loss of function for each of the genes, the tomato plant to be examined can be evaluated as having lost in function for each of the genes, for example. In addition, when the expression level of a protein encoded by each of the genes in a biological sample of the tomato plant to be examined is lower than the expression level of a protein encoded by the corresponding gene in a corresponding wild-type tomato plant, when the expression level of a protein encoded by each of the genes in a biological sample of the tomato plant to be examined is the same as (not significantly different from) the expression level of a protein encoded by each of the genes in a plant with loss of function for each of the genes, and/or when the expression level of a protein encoded by each of the genes in a biological sample of the tomato plant to be examined is lower than the expression level of the gene in a plant with loss of function for each of the genes, the tomato plant to be examined can be evaluated as having lost in function for each of the genes, for example. In the step (x2), for example, a tomato plant evaluated as having lost in function for the SlTOM1a gene, SlTOM1c gene, and SlTOM1d gene is selected as the *Tobamovirus* resistant tomato plant.

In the step (x2), for example, the genotype of each of the genes may be evaluated based on the expression level of each of the genes, specifically, a homozygous form of normal genes, a heterozygous form of a normal gene and a loss-of-function gene, or a homozygous form of loss-of-function genes may be evaluated. In this case, the evaluation can be made by using, as the reference value, a wild-type tomato plant, a tomato plant (heterozygous tomato plant) in which one of two genes seated on a pair of chromosomes is a normal gene and the other is a loss-of-function gene, or a tomato plant (homozygous tomato plant with loss of function) in which both of two genes seated on a pair of chromosomes are loss-of-function genes. Specifically, in the step (x2), when the expression level of the target gene in the tomato plant to be examined is the same as the expression level of the target gene in a wild-type tomato plant, a heterozygous tomato plant, or a homozygous tomato plant with loss of function, the tomato plant to be examined can be evaluated to be, for example, the same genotype as the tomato plant having the same expression level.

Further, in the step (x2), selection can be made based on the evaluation of the resulting genotype of each of the genes. As a specific example, in the step (x2), when the genotype of each of the genes corresponds to the combination of the genotypes described above, the plant is selected as a *Tobamovirus* resistant tomato plant. As a specific example, in the step (x2), for example, when the plant includes loss-of-function genes for a SlTOM1a gene, a SlTOM1c gene, and a SlTOM1d gene in a homozygous form, the tomato plant to be examined may be selected as a *Tobamovirus* resistant tomato plant. In the step (x2), for example, when the plant includes loss-of-function genes for a SlTOM1a gene, a SlTOM1c gene, and a SlTOM1c gene in a homozygous form and includes a loss-of-function gene for a SlTOM1d gene in a heterozygous, the tomato plant to be examined may be selected as a *Tobamovirus* resistant tomato plant. Further, in the step (x2), for example, when the plant includes loss-of-function genes for a SlTOM1a gene, a SlTOM1b gene, a SlTOM1c gene, and a SlTOM1d gene in a homozygous form, the tomato plant to be examined may be selected as a *Tobamovirus* resistant tomato plant.

In the selection in the step (x), a *Tobamovirus* resistant tomato plant with loss of function for a SlTOM1b gene may be selected. In this case, the step (x1) is a step of detecting whether or not a SlTOM1a gene, a SlTOM1b gene, a SlTOM1c gene, and a SlTOM1d gene of the tomato plant to be examined lose function. The step (x2) is a step of selecting, when the SlTOM1a gene, the SlTOM1b gene, the SlTOM1c gene, and the SlTOM1d gene lose function, the tomato plant to be examined selected as a *Tobamovirus* resistant tomato plant. The present invention is not limited thereto, and, in the step (x), a plant in which at least one selected from the group consisting of the SlTOM1a gene, the SITOM1b gene, the SITOM1c gene, and the SITOM1d gene has lost in function may be selected from one or more tomato plants to be examined. Further, in the step (x), a plant in which a SITOM1d gene and at least one selected from the group consisting of a SITOM1a gene, a SITOM1b gene, and a SITOM1c gene lose function may be selected.

The step (y) may also be referred to as a step of causing loss of function for a SITOM1a gene, a SITOM1c gene, and a SITOM1d gene of the target tomato plant, for example (causing loss of function). Regarding the causing loss of function, reference can be made to the description as to the causing loss of function in the imparting method of the present invention to be described below.

Next, in the step (a), a tomato plant used as the other parent is not particularly limited, and may be, for example, a known *Tobamovirus* resistant tomato plant (for example, tomato plant having Tm-2$^2$), a tomato plant having another resistance, or the resistant tomato plant of the present invention.

In the step (a), the method of crossing the *Tobamovirus* resistant tomato plant with the other tomato plant is not particularly limited, and a known method can be employed.

In the step (b), a plant to be selected as a *Tobamovirus* resistant tomato plant may be, for example, a tomato plant obtained in the step (a), or a progeny line obtained from such a tomato plant. Specifically, a plant to be selected as a *Tobamovirus* resistant tomato plant may be, for example, a F1 tomato plant obtained by the crossing in the step (a) or a progeny line obtained from such a tomato plant. The progeny line may be, for example, a selfed progeny or a backcross progeny of the F1 tomato plant obtained by the crossing in the step (a), or may be a tomato plant obtained by crossing the progeny line of the F1 tomato plant with another tomato plant.

In the step (b), selection of a *Tobamovirus* resistant tomato plant can be performed, for example, by directly or indirectly examining the *Tobamovirus* resistance.

In the step (b), the selection by the direct examination can be achieved, for example, based on the presence or absence of filiform leaf and/or presence or absence of growth retardation with reference to the symptom described in the Reference Information 1. The filiform leaf means, for example, that a part of a leaf shrinks and exhibits a filiform form, and as a specific example, reference can be made to the example of Symptoms of ToBRFV (German DSMZ isolate) on *Solanum lycopersicum* cv. 'moneymaker' obtained by artificial inoculation under quarantine facilities (France, 2019) in the following Reference 1 Information. When the tomato plant to be examined is infected with *Tobamovirus*, for example, filiform leaf formation and/or growth retardation is observed in the tomato plant to be examined. Thus, if the tomato plant to be examined forms filiform leaf and/or is delayed in growth, the tomato plant to be examined can be evaluated as suffering from *Tobamovirus*, i.e., susceptible to *Tobamovirus*. On the other hand, if the tomato plant to be examined does not form filiform leaf and/or is not delayed in growth, the tomato plant to be examined can be evaluated as not suffering from *Tobamovirus*, i.e., resistant to *Tobamovirus*. The growth retardation may be evaluated by comparison with tomato plants not infected with *Tobamovirus* (e.g., individuals not inoculated with *Tobamovirus*), or may be evaluated by comparison with the growth state of general tomato plants in consideration of the number of cultivation days of the tomato plants to be examined.

In the step (b), selection by the indirect examination can be achieved, for example, by the following steps (b1) and (b2):

(b1) detecting whether or not a SITOM1a gene, a SITOM1c gene, and a SITOM1d gene of the tomato plant to be examined lose function by the step (a); and (b2) selecting, when the SITOM1a gene, the SITOM1c gene, and the SITOM1d gene lose function, the tomato plant to be examined as a *Tobamovirus* resistant tomato plant.

The selection of the *Tobamovirus* resistant tomato plant in the step (b) is, for example, the same as that described in the step (x), and the step (b1) can be performed in the same manner as in the step (x1) and the step (b2) can be performed in the same manner as in the step (x2).

The production method of the present invention is, preferably, to further breed the *Tobamovirus* resistant tomato plant selected in the step (b). The breeding condition and the breeding method of the tomato plant can be appropriately determined, for example, according to the growth stage of the tomato plant and the cultivar of the tomato plant. In the breeding, for example, the plant may be bred to any growth stage of the tomato plant.

As described above, in the step (b), the tomato plant determined to be resistant to *Tobamovirus* or the progeny line of such a tomato plant can be selected as a *Tobamovirus* resistant tomato plant.

The production method of the present invention may further include the step of collecting seeds from the progeny line obtained by the crossing.

<Imparting Method>

As described above, the method for imparting *Tobamovirus* resistance to a tomato plant of the present invention includes the step of causing loss of function for a SITOM1a gene, a SITOM1c gene, and a SITOM1d gene of a target tomato plant. The imparting method of the present invention is characterized in that it causes loss of function for a SITOM1a gene, a SITOM1c gene, and a SITOM1d gene of the target tomato plant, and other steps and conditions are not particularly limited. According to the imparting method of the present invention, *Tobamovirus* resistance can be imparted to a tomato plant. Regarding the imparting method of the present invention, reference can be made to the descriptions as to the *Tobamovirus* resistant tomato plant and the first production method of the present invention.

In the present invention, as described above, the loss of function for each of the genes in the SITOM1 gene group may be carried out by introducing a loss-of-function mutation into each of the genes, by introducing a polynucleotide for suppressing the expression of each of the genes, or by crossing the tomato plant of the present invention with the target tomato plant. When loss of function for each of the genes is caused by the crossing, the imparting method of the present invention can be carried out, for example, in the same manner as in the first production method of the present invention described above.

When a loss of function for each of the genes is caused by introducing a loss-of-function mutation into each of the genes, in the causing loss of function, a loss-of-function mutation is introduced into the SITOM1a gene, the SITOM1c gene, and the SITOM1d gene of the target tomato plant, for example. The target tomato plant includes the SITOM1a gene, the SITOM1c gene, and the SITOM1d gene in each of a pair of chromosomes, for example. Therefore, in the causing loss of function, for example, one of the SITOM1a genes, the SITOM1c genes, and the SITOM1d genes of the SITOM1a genes, the SITOM1c genes, and the SITOM1d genes seated on a pair of chromosomes in the target tomato plant or both of them may be lost in function, but the latter is preferable. In the causing loss of function, it is preferable to introduce a loss-of-function mutation so that the genotype of each of the genes corresponds to the combination of the aforementioned genotypes. As a specific example, in the causing loss of function, a loss-of-function mutation is introduced so as to include the loss-of-function genes for a SITOM1a gene, a SITOM1c gene, and a SITOM1d gene in a homozygous form. Also, in the causing loss of function, a loss-of-function mutation is introduced so as to include the loss-of-function genes for the pair of SITOM1a genes, the pair of SITOM1b genes, and the pair of SITOM1c genes in a homozygous form and to include the loss-of-function genes for the pair of SITOM1d genes in a heterozygous form. In addition, in the causing loss of function, for example, a loss-of-function mutation is introduced so as to have the loss-of-function genes for the SITOM1a gene, the SITOM1b gene, the SITOM1c gene, and the SITOM1d gene in a homozygous form.

The loss of function for each of the genes can be carried out, for example, by introducing a mutation as described above. Regarding the mutation, for example, reference can be made to the aforementioned description, and the mutation is preferably a nonsense mutation or a frameshift mutation. The loss-of-function mutation may be introduced, for example, by deletion, substitution, insertion, and/or addition of one or several bases with respect to each of the genes (base sequence of each of the genes), and is preferably introduced by partial deletion or complete deletion of a normal gene of each of the genes.

In the causing loss of function, the region where a loss-of-function mutation is introduced into each of the genes may be an intron region or an exon region of each of the genes, and the latter is preferable.

The loss of function for each of the genes can be caused, for example, by introducing mutations into target genes of target tomato plants in a conventional manner. The method of introducing such mutations can be carried out, for example, by homologous recombination and genome editing techniques using ZFN, TALEN, CRISPR-CAS9, CRISPR-CPF1, and the like. Regarding the method of introducing a mutation using the genome editing technique, for example, reference may be made to Example 1 to be described below. The method of introducing the mutation may be carried out by, for example, random mutagenesis. Examples of the random mutagenesis include radiation treatment with α-ray, β-ray, γ-ray, X-ray, or the like; chemical treatment with a mutagen such as ethyl methanesulfonate (EMS), ethinyl nitrosourea (ENU), or the like; and heavy ion beam treatment. Note that the method of introducing a mutation described above may be performed using, for example, a commercially available kit or the like.

The target tomato plant may be any of, for example, plant cells, calluses, plant tissues, and plant individuals.

In the imparting method of the present invention, it is preferable to select a plant in which a function loss mutation is introduced into each of the genes after the causing loss of function. The tomato plant to be selected may be, for example, a tomato plant obtained in the causing loss of function, or a progeny line of such a plant. The selection can be performed, for example, in the same manner as the step (x), and reference can be made to the description as to the step (x).

Next, in the case of introducing a polynucleotide for suppressing expression of each of the genes, the method of introducing the polynucleotide is not particularly limited, and may be carried out by, for example, a method such as RNA interference, antisense RNA, genome editing technology, or the like. An expression cassette such as an expression vector containing the polynucleotide can be introduced into a target tomato plant by, for example, a polyethylene glycol method, an electroporation method, a method via *Agrobacterium*, a particle gun method, or the like. The target tomato plant may be any of, for example, plant cells, calluses, plant tissues, and plant individuals.

<Second Production Method>

As described above, a method for producing a *Tobamovirus* resistant tomato plant of the present invention includes the step of imparting *Tobamovirus* resistance to a target tomato plant, and the imparting is carried out by the method for imparting *Tobamovirus* resistance to a tomato plant of the present invention. The second production method of the present invention is characterized in that the imparting is carried out by the method for imparting *Tobamovirus* resistance to a tomato plant of the present invention, and other steps and conditions are not particularly limited. According to the second production method of the present invention, a *Tobamovirus* resistant tomato plant can be produced. Regarding the second production method of the present invention, reference can be made to the descriptions as to the resistant tomato plant, the first production method, and the imparting method of the present invention.

<Screening Method>

As described above, a method for screening a *Tobamovirus* resistant tomato plant of the present invention includes the step of: selecting a tomato plant to be examined with loss of function for a SITOM1a gene, a SITOM1c gene, and a SITOM1d gene from one or more tomato plants to be examined as a *Tobamovirus* resistant tomato plant. The screening method of the present invention is characterized in that the loss of function for a SITOM1a gene, a SITOM1c gene, and a SITOM1d gene is used as an indicator, and other steps and conditions are not particularly limited. According to the screening method of the present invention, a *Tobamovirus* resistant tomato plant can be screened. Regarding the screening method of the present invention, reference can be made to the descriptions as to the resistant tomato plant, the first production method, and the imparting method of the present invention.

In the screening method of the present invention, the selecting can be performed in the same manner as in the step (x), and reference can be made to the description as to the step (x).

<Third Production Method>

As described above, a method for producing a *Tobamovirus* resistant tomato plant of the present invention includes the step of: screening a tomato plant to be examined with loss of function for a SITOM1a gene, a SITOM1c gene, and a SITOM1d gene from one or more tomato plants to be examined, wherein the screening is carried out by the method for screening a *Tobamovirus* resistant tomato plant according to the present invention. The third production method of the present invention is characterized in that the screening is carried out by the screening method of the present invention, and other steps and conditions are not particularly limited. Regarding the third production method of the present invention, reference can be made to the descriptions as to the resistant tomato plant, the first production method, the imparting method, and the screening method of the present invention.

<Second Tomato Plant>

The *Tobamovirus* resistant tomato plant of the present invention (hereinafter, also referred to as "second tomato plant") can be obtained by the first production method, the second production method, or the third production method of the present invention. The second tomato plant of the present invention is characterized in that it is obtained by the first production method, the second production method, or the third production method of the present invention, and other configurations and conditions are not particularly limited. Regarding the second tomato plant of the present invention, reference can be made to the descriptions as to the resistant tomato plant, the first production method, the imparting method, the second production method, the screening method, and the third production method of the present invention.

<Processed Food>

As described above, a tomato plant processed food uses the *Tobamovirus* resistant tomato plant according to the present invention. The plant processed food of the present invention is characterized in that the resistant tomato plant of the present invention is used as a tomato plant to be processed, and other configurations and conditions are not particularly limited. Regarding the processed food of the present invention, reference can be made to the descriptions as to the resistant tomato plant, the first production method, the imparting method, the second production method, the screening method, the third production method, and the second tomato plant of the present invention.

In the processed food of the present invention, "processing" is not particularly limited, and means any processing on a tomato plant, for example. Specific examples of the processing include cutting, slicing, mincing, backing, drying, canning, bottling, washing, packaging, freezing, heating, and seasoning. One or two or more types of processing may be performed in the production of the processed food. In addition, in the production of the processed food, the same processing may be performed one time or may be performed a plurality of times.

<Detection Method>

As described above, a method for detecting *Tobamovirus* resistance in a tomato plant of the present invention includes the step of: detecting whether or not a SlTOM1a gene, a SlTOM1c gene, and a SlTOM1d gene lose function in a tomato plant to be examined. The detection method of the present invention is characterized in that it detects whether or not a SlTOM1a gene, a SlTOM1c gene, and a SlTOM1d gene lose function in the detecting, and other steps and conditions of the detection method are not particularly limited. According to the detection method of the present invention, it is possible to detect whether or not the tomato plant to be examined is resistant to *Tobamovirus*. Regarding the detection method of the present invention, reference can be made to the descriptions as to the resistant tomato plant, the first production method, the imparting method, the second production method, the screening method, the third production method, and the second tomato plant of the present invention.

The detection method of the present invention includes, for example, the step of detecting a loss-of-function mutation in a SlTOM1a gene, a SlTOM1c gene, and a SlTOM1d gene of a tomato plant to be examined. Regarding the detecting, for example, reference can be made to the description as to the step (x) or the indirect selection in the selecting of the first production method of the present invention. As a specific example, in the detecting, gene expression or the base sequence thereof is detected, for example, for a SlTOM1a gene, a SlTOM1c gene, and a SlTOM1d gene. In the detecting, for example, the gene expression or the base sequence thereof is further detected for a SlTOM1b gene.

The detection method of the present invention preferably further includes the step of determining whether or not the SlTOM1a gene, the SlTOM1c gene, and the SlTOM1d gene of the tomato plant to be examined are normal genes or loss-of-function genes on the basis of the gene expression or the base sequence thereof. The determining can be performed, for example, by comparing the SlTOM1a gene, the SlTOM1c gene, and the SlTOM1d gene of the tomato plant to be examined with the SlTOM1a gene, the SlTOM1c gene, and the SlTOM1d gene of the corresponding wild-type tomato plant. Specifically, in the determining, when the SlTOM1a gene, the SlTOM1c gene, and the SlTOM1d gene of the tomato plant to be examined include the same base sequence as the SlTOM1a gene, the SlTOM1c gene, and the SlTOM1d gene of the wild-type tomato plant, or have a mutation that is not a loss-of-function mutation, the SlTOM1a gene, the SlTOM1c gene, and the SlTOM1d gene of the tomato plant to be examined can be determined to be normal genes. On the other hand, in the determining, when the SlTOM1a gene, the SlTOM1c gene, and the SlTOM1d gene of the tomato plant to be examined have a loss-of-function mutation, the SlTOM1a gene, the SlTOM1c gene, and the SlTOM1d gene of the tomato plant to be examined can be determined to be loss-of-function genes. When the detection method of the present invention detects a loss-of-function mutation for a SlTOM1b gene in the detecting, the detection method of the present invention preferably further includes the step of determining whether or not the SlTOM1b gene of the tomato plant to be examined is a normal gene or a loss-of-function gene based on the gene expression or the base sequence. In the determining, when the SlTOM1b gene of the tomato plant to be examined includes the same base sequence as the SlTOM1b gene of the wild-type tomato plant or has a mutation that is not a loss-of-function mutation, the SlTOM1b gene of the tomato plant to be examined can be determined to be a normal gene. On the other hand, in the determining, when the SlTOM1b gene of the tomato plant to be examined has a loss-of-function mutation, the SlTOM1b gene of the tomato plant to be examined can be determined to be a loss-of-function gene. In the detecting, the SlTOM1a gene, the SlTOM1c gene, and the SlTOM1d gene are used as indicators, but the present invention is not limited thereto, and for example, at least one gene selected from the group consisting of the SlTOM1a gene, the SlTOM1b gene, the SlTOM1c gene, and the SlTOM1d gene may be used as an indicator.

EXAMPLES

The present invention will be described in detailed below with reference to examples. It is to be noted, however, that the present invention is by no means limited to examples described in the following examples.

Example 1

It was examined that a tomato plant of the present invention is resistant to *Tobamovirus*.

(1) Introduction of Loss-of-Function Mutation

Introduction of loss-of-function mutations into SlTOM1a to d genes was performed by a genome editing technique using a CRISPR-CAS9 system. Specifically, pDe-Cas9_Kan (Reference 2), which is a binary vector having a Cas9 and a guide sequence insertion site on T-DNA, was used as an expression vector to be introduced into a plant cell. The guide RNA sequence for each of the genes was designed using a CRISPR-P program (Reference 3). From the resulting candidate guide RNAs, a guide RNA sequence that was predicted to be less susceptible to cleavage of off-target sites (non-target sites) was selected. Using purified Cas9 protein, the selected candidate guide RNA, and DNA having a target sequence, the cleavage activity of the DNA having the target sequence was examined in a test tube, and the guide RNA sequence having the cleavage activity was used as a guide RNA to be introduced into a tomato plant to be described below.

Reference 2: Friedrich Fauser et. al., "Both CRISPR/Cas-based nucleases and nickases can be used efficiently for genome engineering in *Arabidopsis thaliana*", *The Plant Journal*, 2014, vol. 79, pages 348-359

Reference 3: Yang Lei et. al, "CRISPR-P: A Web Tool for Synthetic Single-Guide RNA Design of CRISPR-System in Plants", Molecular Plant, 2014, vol. 7, pages 1494-1496

The guide RNA sequences and protospacer adjacent motifs (PAMs) for each of the genes are as follows. In the sequences below, the underlined base sequence is PAM.

Target sequence of guide RNA for SITOM1a gene and SITOM1d gene

```
                                      (SEQ ID NO: 12)
5'-GTTGTGAAGAATGCAAGACTTGG-3'
```

Target sequence of guide RNA for SITOM1b gene

```
                                      (SEQ ID NO: 13)
5'-TCAAAGATGGGGCGAACTCGTGG-3'
```

Target sequence of guide RNA for SITOM1c gene

```
                                      (SEQ ID NO: 14)
5'-GCCGATTGACATCGCCGGTCCGG-3'
```

Next, gene cassettes, in which three types of guide RNA sequences selected were inserted downstream of the U6 promoters, respectively, were produced. The resulting gene cassettes were tandemly inserted into the cloning site of the pDe-Cas9_Kan vector (so that the three types of guide RNA sequences were arranged consecutively) to generate an expression vector for Cas9 and guide RNA. In addition, the resulting expression vector was introduced into a cotyledon piece of a tomato plant (GCR26 line: ToMV-sensitive) using *Agrobacterium*. After selection using kanamycin resistance by nptII of selectable marker on T-DNA as an indicator, a transformant (T0 generation) was obtained through callus induction, shoot induction, and rooting. A series of operations involved in the transformation of tomatoes were carried out according to the method of Reference 4.

Reference 4: Hyeon-Jin Sun et. al, "A Highly Efficient Transformation Protocol", Plant Cell Physiol., 2006, vol. 47, No. 3, pages 426-431

Genomic DNA was purified from each individual of the resulting T0 plant by a conventional method. The presence or absence of mutation in the vicinity of the target site of the SITOM1c gene in the genomic DNA was detected by a method using Cleaved Amplified Polymorphic Sequence (CAPS) (Reference 5). In the genomic DNA, the presence or absence of mutation in the vicinity of the target site of the SITOM1a gene, the SITOM1b gene, and the SITOM1d gene was detected by a method using T7 endonuclease 1 (Reference 6). The results suggested that 18 shoots from 11 independent calli had mutations in any one or more genes of the SITOM1 gene group.

Reference 5: Andrzej Konieczny et. al., "A procedure for mapping *Arabidopsis* mutations using co-dominant ecotype-specific PCR-based markers.", The Plant Journal, 1993, vol. 4, No. 2, pages 403-410

Reference 6: Lena Vouillot et. al., "Comparison of T7E1 and Surveyor Mismatch Cleavage Assays to Detect Mutations Triggered by Engineered Nucleases", 2015, vol. 5, No. 3, pages 407-415

Next, plant individuals (T0 generation) derived from the 18 shoots were self-crossed, and T1 seeds were obtained from four strains (#4d, #47, #57, and #106). The four strains are derived from different calli. After seeding and breeding the resulting T1 seeds, genomic DNA was purified from each individual of the resulting T1 plant by a conventional method. Then, the base sequence in the vicinity of the target sequence of the genomic DNA of each individual was determined. As a result, mutations were found in T1 plants derived from three T0 plants (#47, #57, and #106). In one of these three lines, Cas9 and nptII genes were found in the T1 plant. On the other hand, in the other two lines (#57-1, #106-1), none of these genes were present at least in perfect forms (assayed by PCR). The Cas9 gene and the nptII gene were detected by PCR. The results of the two lines (#57-1 and #106-1) are summarized in Table 1 below. As summarized in Table 1, in the T1 plant #57-1-3, the SITOM1b gene, the SITOM1c gene, and the SITOM1d gene had frameshift mutations due to deletions of 5, 1, and 2 bases, respectively, i.e., loss-of-function mutations were introduced into the SITOM1b gene, the SITOM1c gene, and the SITOM1d gene. In the T1 plant #106-1-4, the SITOM1a gene, and the SITOM1c gene had frameshift mutations due to insertion of 1 base, i.e., loss-of-function mutations were introduced into the SITOM1a gene and the SITOM1c gene. As evidenced by the analysis described below, mutations were introduced into the exon region in all of the SITOM1a gene, the SITOM1b gene, the SITOM1c gene, and the SITOM1d gene.

TABLE 1

| T1 individual | SITOM1a | SITOM1b | SITOM1c | SITOM1d | Cas9 | NptII |
|---|---|---|---|---|---|---|
| #57-1-3 | 3 bp del/6 bp del | 5 bp del (homo) | 1 bp del (homo) | 2 bp del (homo) | — | — |
| #106-1-4 | 1 bp ins/wt | wt (homo) | 1 bp ins/wt | wt (homo) | — | — | wt: wild-type, del: deletion, ins: insertion,

—: none

Next, the T1 plants #57-1-3 and #106-1-4 were crossed with the non-transformed plant (GCR26 line). From the resulting line, lines (test lines) having Sltom1a-1 (#106-1-4-derived), Sltom1b-1 (#57-1-3 derived), Sltom1c-1 (#57-1-3 derived), and Sltom1d-1 (#57-1-3 derived) mutations in various combinations were established. For the genotyping of the progeny line, fragment analysis (analysis by DNA sequencer of amplified fragment length polymorphism), CAPS analysis, dCAPS (derived cleaved amplified polymorphic sequence, Reference 7) analysis, and DNA sequencing analysis were used in combination. The results of each mutant allele are shown below.

Reference 7: Michael M. Neff et. al., "dCAPS, a simple technique for the genetic analysis of single nucleotide polymorphisms: experimental applications in *Arabidopsis thaliana* genetics", The Plant Journal, 1998, vol. 14, No. 3, pages 387-392

(Mutant Allele)

Mutant allele of SlTOM1a

SlTOM1ad consensus guide sequence (complementary strand):

```
                                      (SEQ ID NO: 15)
              CCAAGT-CTTGCATTCTTCACAAC
```

Sltom1a-1 (106-1-4-derived) (ins1):

```
                                      (SEQ ID NO: 16)
          ATGCCAAGTACTTGCATTCTTCACAACTTT
```

Amino acid sequence of Sltom1a-1:

```
              M  P  S  (frameshift mutation)
```

Amino acid residue number (full length 295 residue): 105

Mutant allele of SlTOM1b

SlTOM1b guide sequence (complementary strand):

```
                                      (SEQ ID NO: 17)
              CCACGAGTTCGCCCCATCTTTGA
```

Sltom1b-1 (57-1-3-derived) (del5):

```
                                      (SEQ ID NO: 18)
          ACACCACGAG-----CCCATCTTTGATTG
```

Amino acid sequence of Sltom1b-1:

```
              T  P  R  (frameshift mutation)
```

Amino acid residue number (full length 297 residue): 21

Mutant allele of SlTOM1c

SlTOM1c guided sequence:

```
                                      (SEQ ID NO: 19)
              GCCGATTGACATCGCCGGTCCGG
```

Sltom1c-1 (57-1-3-derived) (del1):

```
                                      (SEQ ID NO: 20)
          TCGCCGATTGACATCGCC-GTCCGGTGA
```

Amino acid sequence of Sltom1c-1:

```
                                      (SEQ ID NO: 21)
              S  P  I  D  I  A  (frameshift mutation)
```

Amino acid residue number (full length 288 residue): 14

Mutant allele of SlTOM1d

SlTOM1ad consensus guide sequence (complementary strand):

```
                                      (SEQ ID NO: 22)
              CCAAGTCTTGCATTCTTCACAAC
```

Sltom1d-1 (57-1-3-derived) (del2):

```
                                      (SEQ ID NO: 23)
          ATGCCAAGT--TGCATTCTTCACAACTTT
```

Amino acid sequence of Sltom1d-1:

```
              M  P  S  (frameshift mutation)
```

Amino acid residue number (full length 295 residue): 105

Abbreviations del: deletion, ins: insertion, —: deleted base

The underlined sequence indicates PAM.

(2) Examination of *Tobamovirus* Resistance

The seeds of the test line were allowed to absorb water, seeded, and developed cotyledons. The cotyledons of the test line 10 days after water absorption were inoculated with purified *Tobamovirus* (ToMV-L, 0.1 g/l of tobacco mosaic virus tomato strain (L) in Reference 8) by applying the purified *Tobamovirus* to the entire surface of the cotyledons so as to achieve 10 ∥l per cotyledon, and then the purified *Tobamovirus* was washed away with water. The genomic base sequence of ToMV-L is consisting of the base sequence registered under Genbank Accession No.: X02144. After the inoculation, the cotyledons were further cultivated for 7 days. The cultivation was carried out using an artificial meteorological device under conditions of 25° C. (constant), 16 hours light phase, and 8 hours dark phase. After the cultivation, samples were prepared from inoculated cotyledons (inoculated leaves) and the accumulation of coat protein (CP) in the inoculated leaves was examined. Specifically, about half (about 20 mg) of the inoculated leaves were collected into a 1.5 ml tube containing two zirconia balls (3 mm in diameter). Then, 30 μl of extraction buffer was added, and grinding (Qiagen Tissue Lyser, one set of "28 times per second for 30 seconds" was performed 2 times) was performed. The composition of the extraction buffer was as follows: 225 mmol/l Tris-HCl pH 7.5, 2.5 mmol/l EDTA-Na pH 8, and 1 mg/ml ascorbic acid. The resulting product was collected at the bottom of the tube by centrifugation, and then 120 μl of gel sample buffer diluted 4 times with water was added and mixed. The composition of the gel sample buffer was as follows: 0.624 mol/l Tris-HCl pH 6. 8, 0.2 g/ml SDS, 0.8 mg/ml bromophenol blue, 10% (vol/vol) glycerol, and 1 mol/l DTT. After centrifugation (14 krpm, 5 min, 23° C.), the supernatant was obtained as a sample for SDS-PAGE. The resulting sample was subjected to SDS-PAGE, followed by staining with Coomassie Brilliant Blue (CBB), and the CP accumulation was examined. In addition, the CP accumulation was examined in the same manner except that the GCR26 line was used as the wild-type strain instead of the test strain. The results are shown in FIG. 1.

Reference 8: Takeshi OHNO et. al., "Nucleotide sequence of the tobacco mosaic virus (tomato strain) genome and comparison with the common strain genome.", 1984, J. Biochem., vol. 96, No. 6 pages 1915-1923

Figure 1B:
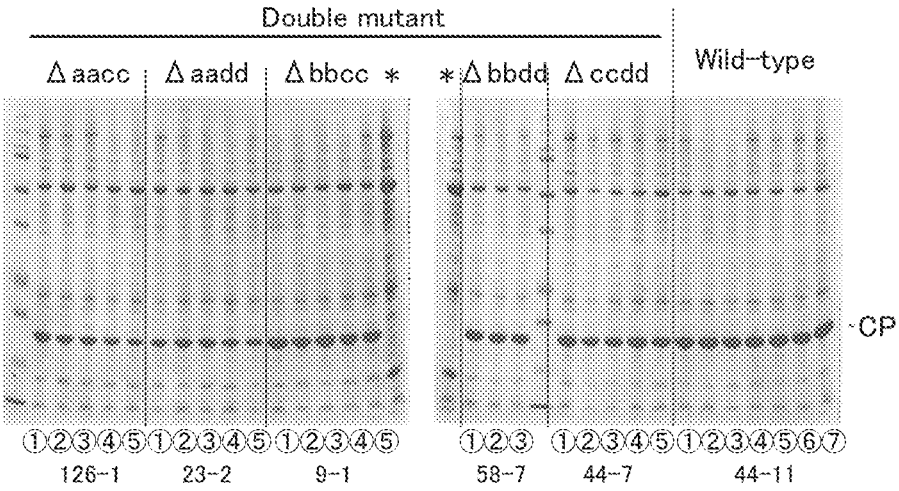
Figure 1C:
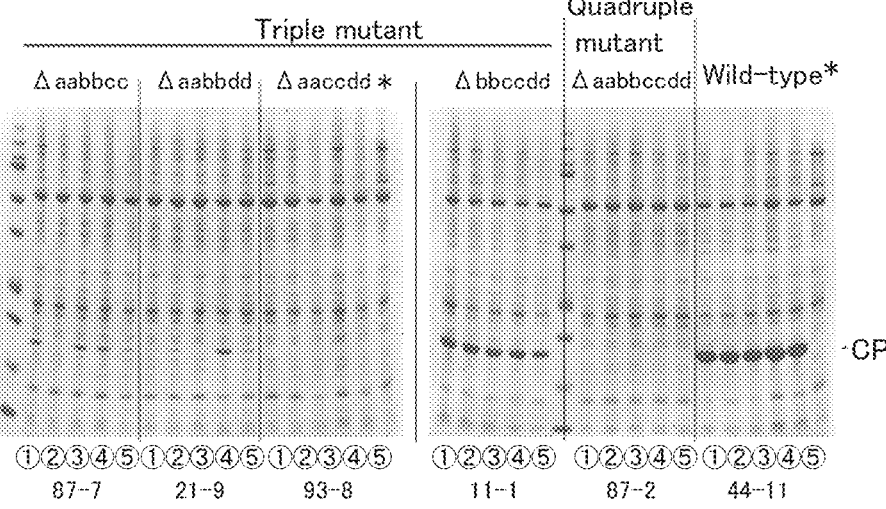

FIGS. 1A to 1C are photographs each showing a staining diagram after CBB staining. FIG. 1A shows the results of the single mutant, the double-mutant, and the wild-type. FIG. 1B shows the results of the double-mutant and the wild-type. FIG. 1C shows the results of the triple-mutant, the quadruple mutant, and the wild-type. In FIGS. 1A to 1C, the genotype of each test line and non-inoculation (*) are written above the photograph, and the strain names of the test lines from which the samples were derived are written below the photograph. Note that in FIGS. 1A to 1C, the test lines with mutant alleles of the Sltom1a-1, the Sltom1b-1, the Sltom1c-1 and the Sltom1d-1 are shown using a, b, c, and d, respectively. As a specific example, when the test line is Δaa, both alleles of SITOM1a are mutant alleles (Sltom1a-1) in the test line.

As shown in FIG. 1A, when one of the SITOM1a to d genes was lost in function, the degree of ToMV CP accumulation was comparable to that of a wild-type individual and had no significant effect. Also, as shown in FIGS. 1A and 1B, when two of the SITOM1a to d genes were lost in function, the degree of ToMV CP accumulation was slightly decreased compared to that of the wild-type strain. Furthermore, as shown in FIGS. 1B and 1C, among the triple-mutants, the ToMV CP accumulation became higher in the order of Δaaccdd<Δaabbcc<Δaabbdd<Δbbccdd. In particular, slight CP accumulation was observed in the triple-mutant Δaaccdd. In addition, CP accumulation was not observed in the quadruple mutant Δaabbccdd. These results showed that the contribution to the growth of ToMV became smaller in the order of SITOM1a>SITOM1c>SITOM1d>SITOM1b. It should be noted that the CP accumulation in the Δaadd strain was significantly higher than the CP accumulation in the Δaabbdd strain, and that the CP accumulation in the Δaacc strain was significantly higher than the CP accumulation in the Δaabbcc strain, indicating that SITOM1b considered to have the smallest contribution also had a non-zero contribution to the growth of ToMV. Also, consistent with the above discussion, in the double-mutant Δaabb, Δaacc, and Δaadd strains, the ToMV CP accumulation was slightly lower than that of the wild-type strain.

From the above, it was found that the triple-mutant Δaaccdd or the quadruple mutant Δaabbccdd had strong resistance to Tobamovirus.

Next, the resistance was examined in the same manner using ToBRFV. First, a gene cassette having a full-length cDNA of ToBRFV genome (Non-Patent Literature 2, Genbank Accession Number: KX619418) was prepared at the downstream of the T7 RNA polymerase promoter, and infectious RNA was synthesized by in vitro transcription. Incidentally, the full-length cDNA was produced by chemical synthesis. The resulting infectious RNA was then inoculated into Nicotiana benthamiana. Eight days after inoculation, viral growth was examined. Inoculated leaves and upper leaves were harvested and ground with 2 times the raw weight of phosphate buffer solution (0.1 mol/l, pH7). Further, the resulting product was diluted with 18 times the raw weight of water, and used as an inoculum source.

The cotyledons of the test lines were inoculated in the same manner as ToMV inoculation, except that ToBRFV was inoculated instead of ToMV. The coat protein accumulation in the inoculated leaves 7 days after inoculation was examined in the same manner. In addition, instead of the test line, the GCR26 line was used as the wild-type strain, and the GCR267 line was used as the ToMV resistance (Tm-2²)

strain. The CP accumulation was examined in the same manner except that ToMV was used in addition to ToBRFV as a virus. The results are shown in FIG. 2.

Figure 2A:
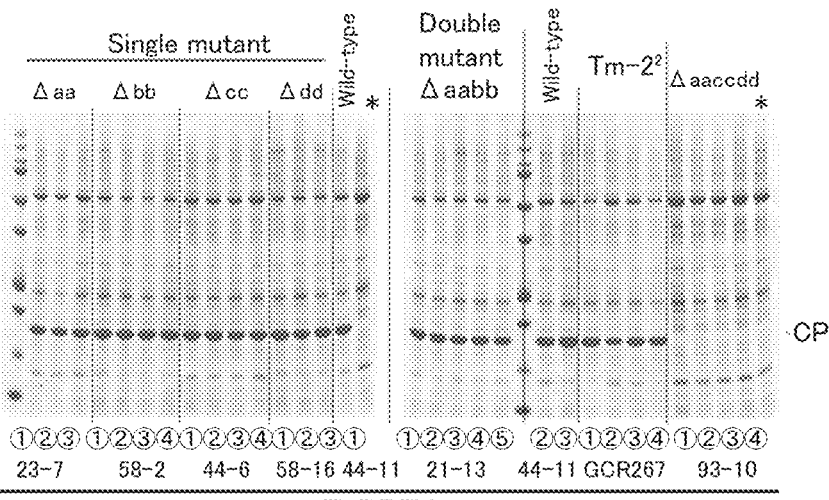
FIGS. 2A to 2C are photographs each showing a staining diagram after CBB staining in Example 1.
Figure 2B:
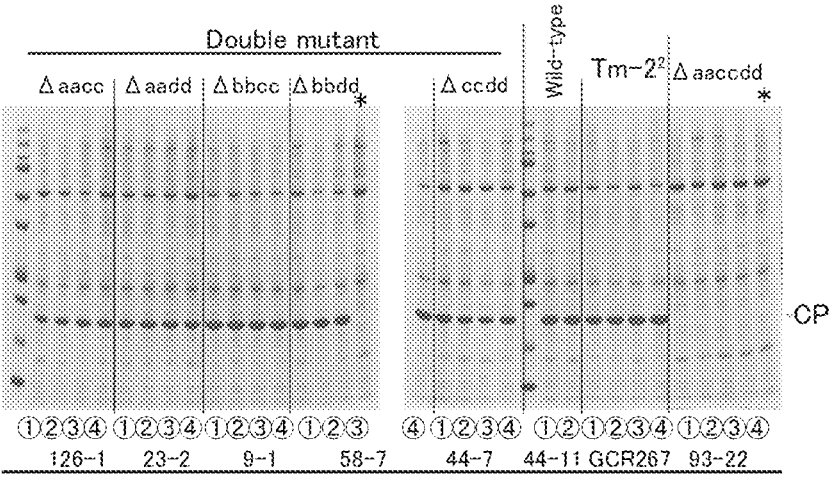
Figure 2C:
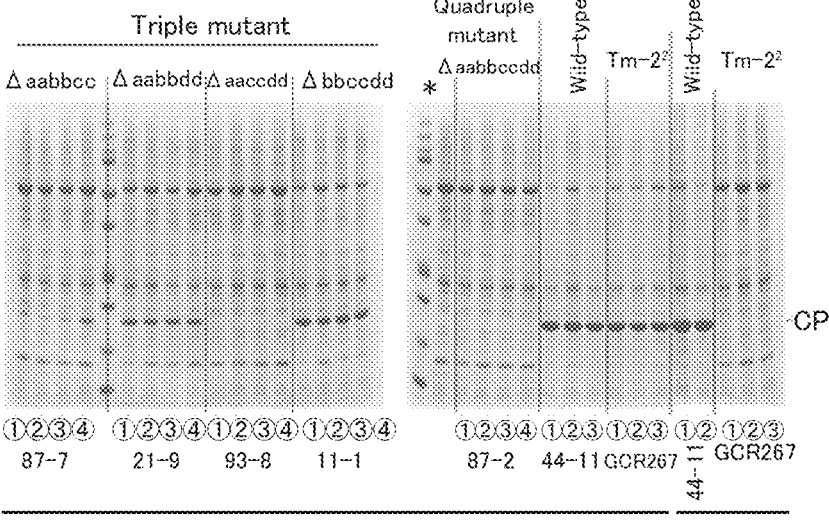

FIGS. 2A to 2C are photographs each showing a staining diagram after CBB staining. FIG. 2A shows the results of the single mutant, the double-mutant, the wild-type, the Tm-2² strain, and the triple-mutant. FIG. 2B shows the results of the double-mutant, the wild-type, the Tm-2² strain, and the triple-mutant. FIG. 2C shows the results of the triple-mutant, the quadruple mutant, the wild-type, and the Tm-2² strain. In FIGS. 2A to 2C, the genotypes of each test line and non-inoculation (*) are written above the photograph, and the strain names of the test lines from which the samples were derived and the type of virus inoculated are written below the photograph. In FIGS. 2A to 2C, the genotypes of each test line and non-inoculation (asterisk) are written above the photograph, and the strain names of the test line from which the sample was derived are written below the photograph. Note that in FIG. 2A to 2C, the test lines with mutant alleles of the Sltom1a-1, the Sltom1b-1, the Sltom1c-1 and the Sltom1d-1 are shown using a, b, c, and d, respectively. As a specific example, when the test line is Δaa, both alleles of SITOM1a are mutant alleles (Sltom1a-1) in the test line.

As shown in FIGS. 2A to 2C, in the case of being inoculated with ToMV, no CP accumulation was observed in the Tm-2² strain and the Tm-2² strain showed resistance. On the other hand, in the case of being inoculated with ToBRFV, CP accumulation was observed in the Tm-2² strain, indicating that ToBRFV defeats the Tobamovirus resistance of the Tm-2² strain. In addition, as shown in FIGS. 2A to 2C, in the case of being inoculated with ToBRFV, no CP accumulation was observed in the quadruple mutant Δaabbccdd and the triple-mutant Δaaccdd. On the other hand, in the case of being inoculated with ToBRFV, CP accumulation was observed in the triple-mutant Δaabbcc, Δaabbdd or Δbbccdd and the CP accumulation was higher in the order of Δaabbcc<Δaabbdd<Δbbccdd. When the CP accumulation in the triple-mutant Δaaccdd was compared with the CP accumulation in the triple-mutant Δaabbcc by Western blotting, it was found that the CP accumulation in the triple-mutant Δaaccdd was below the detection limit, and was 1/100 to 1/10 or less with the CP accumulation in the triple-mutant Δaabbcc as a reference. The detection limit of the CP accumulation in the Western blotting was about 1/100 of the CP accumulation of the fourth plant of 87-7 (triple-mutant Δaabbcc) shown in FIG. 2C.

Although data are not shown, when examining uninoculated upper leaves 21 days after the inoculation, no CP accumulation was observed in any of the six inoculated plants of the quadruple mutant Δaabbccdd. Further, in the triplicate mutant Δaaccdd, very low level of accumulation was observed in three of six inoculated plants and CP was not detected in the other three. Also, CP was significantly accumulated in the triple-mutant Δaabbcc, Δaabbdd or Δbbccdd. Furthermore, when the CP accumulation amount in three plants of the triple-mutant Δaaccdd in which CP accumulation was observed was compared with the CP accumulation amount in the triple-mutant Δaabbcc in which CP accumulation was observed, the CP accumulation amount in the triple-mutant Δaaccdd did not exceed the CP accumulation amount in the triple-mutant Δaabbcc.

These results showed that the contribution to the growth of ToBRFV became smaller in the order of SITOM1a gene>SITOM1c gene>SITOM1d gene>SITOM1b gene as in the case of ToMV. The results also showed that the plants were strongly resistant to ToBRFV when they were the triple-mutant Δaaccdd or the quadruple mutant Δaabbccdd.

(3) Examination of Disease Symptom

The wild-type strain, the triple-mutants Δaabbcc, Δaabbdd, Δaaccdd, and Δbbccdd, the quadruple mutant Δaabbccdd, and the Tm-2² strain were allowed to absorb water and then sown in the same manner as in Example 1(2). Then, in the same manner as in Example 1 (2), ToBRFV was inoculated on day 10 after water absorption. Then, resultants were further cultivated for 20 days, and it was examined to determine whether or not the disease symptom of *Tobamovirus* appeared. In addition, the disease symptom of *Tobamovirus* was examined in the same manner except that the Tm-2² strain was inoculated with ToMV. The results are shown in FIG. 3.

Figure 3A:
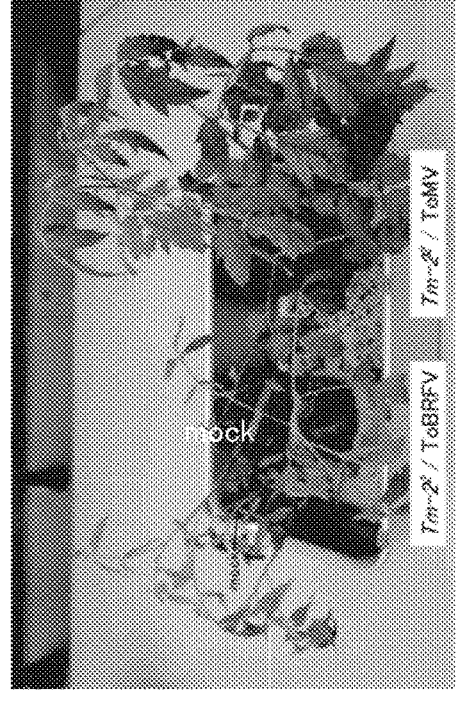
FIGS. 3A to 3D are photographs each showing plants 20 days after *Tobamovirus* inoculation in Example 1.
Figure 3B:
Figure 3C:
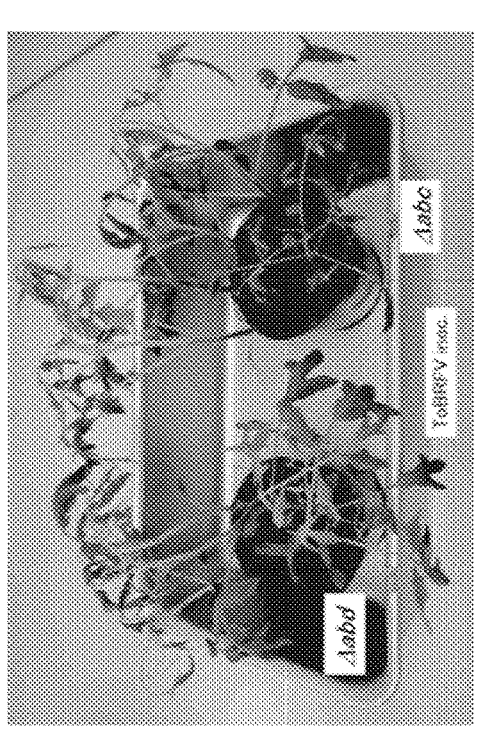
Figure 3D:
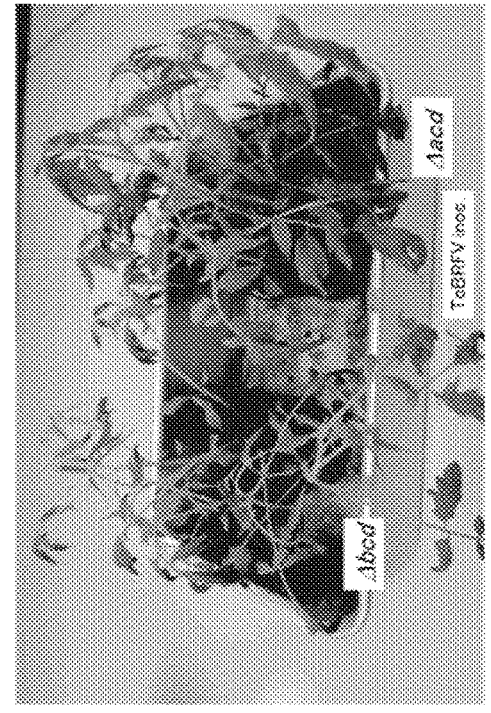

FIGS. 3A to 3D are photographs each showing plants 20 days after *Tobamovirus* inoculation. FIG. 3A shows the results of the Tm-2² strain inoculated with ToMV or ToBRFV, FIG. 3B shows the results of the wild-type strain inoculated with ToBRFV and the quadruple mutant Δaabbccdd (Δabcd), FIG. 3C shows the results of the triple-mutant Δaabbcc (Δabc) and the triple-mutant Δaabbdd (Δabd) inoculated with ToBRFV, and FIG. 3D shows the results of the triple-mutant Δbbccdd (Δbcd) and the triple-mutant Δaaccdd (Δaccd) inoculated with ToBRFV. As shown in FIGS. 3A and 3B, the wild-type strain and the Tm-2² strain inoculated with ToBRFV showed severe disease symptom, and typical filiform leaf symptom. Also, the triple-mutants Δaabbcc, Δaabbdd, and Δbbccdd on day 20 after inoculation showed typical filiform leaf symptom. On the other hand, the triple-mutant Δaaccdd and the quadruple mutant Δaabbccdd in which no or very low level of ToBRFV growth was observed showed no disease symptom even 20 days after inoculation. These results showed that the triple-mutant Δaaccdd or the quadruple mutant Δaabbccdd can suppress the development of disease symptoms of ToBRFV.

(4) Examination of Mutant Growth

The triple-mutant Δaaccdd and the quadruple mutant Δaabbccdd were found to be strongly resistance to *Tobamovirus*. Therefore, it was examined whether or not these mutants grow normally and bear fruits under normal cultivation conditions.

The wild-type strain and the triple-mutant Δaaccdd, and the quadruple mutant Δaabbccdd were allowed to absorb water and then sown in the same manner as in Example 1(2). After the sowing, seedling raising and planting in pots were carried out and cultivated. The appearance of the plants at 24, 39, 70 and 79 days after water absorption and fruiting on day 79 after water absorption were examined. The results are shown in FIG. 4.

Figure 4A:
FIGS. 4A to 4E are photographs each showing the growth and fruiting of wild-type strains and mutants in Example 1.
Figure 4B:
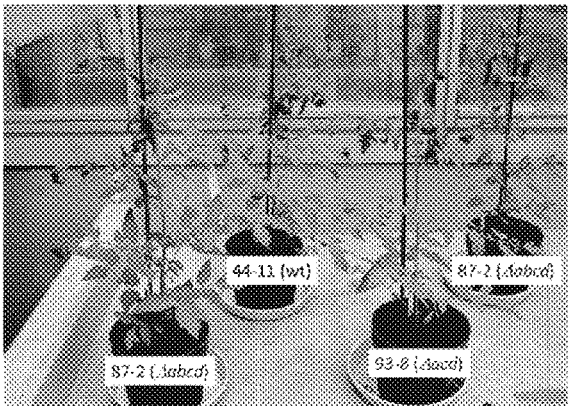
Figure 4C:
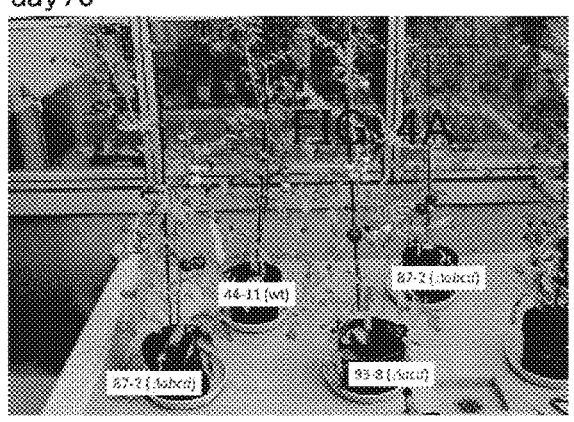
Figure 4D:
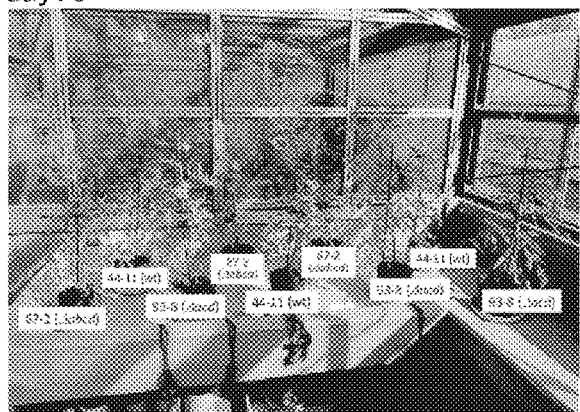
Figure 4E:
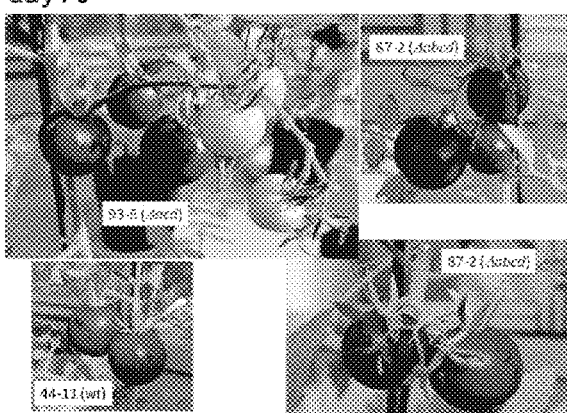

FIGS. 4A to 4E are photographs each showing the growth and fruiting of wild-type strains and mutants. FIG. 4A shows the state on day 24 after water absorption, FIG. 4B shows the state on day 39 after water absorption, FIG. 4C shows the state on day 70 after water absorption, FIG. 4D shows the state on day 79 after water absorption, and FIG. 4E shows the state of fruit formation on day 79 after water absorption. As shown in FIGS. 4A to 4D, the growth of all mutants was generally similar to that of the wild-type strain. Also, as shown in FIGS. 4D and 4E, the fruting of any mutant was generally similar to that of the wild-type strain.

From the above, it was found that the tomato plant of the present invention is resistant to *Tobamovirus*.

Example 2

It was examined that the tomato plant of the present invention is resistant to *Tobamovirus*.

(1) Evaluation of Resistance by Disease Index-1

The wild-type strain, the triple-mutants Δaabbcc, Δaabbdd, Δaaccdd, and Δbbccdd, and the quadruple mutant Δaabbccdd were allowed to absorb water and then sown in the same manner as in Example 1(2). Then, the plants on day 10 after water absorption were inoculated with ToBRFV in the same manner as in Example 1 (2). Then, the tomato plants were grown by cultivating for 21 to 22 days under the above-mentioned conditions, and disease investigation was carried out in the following manner.

Figure 5:
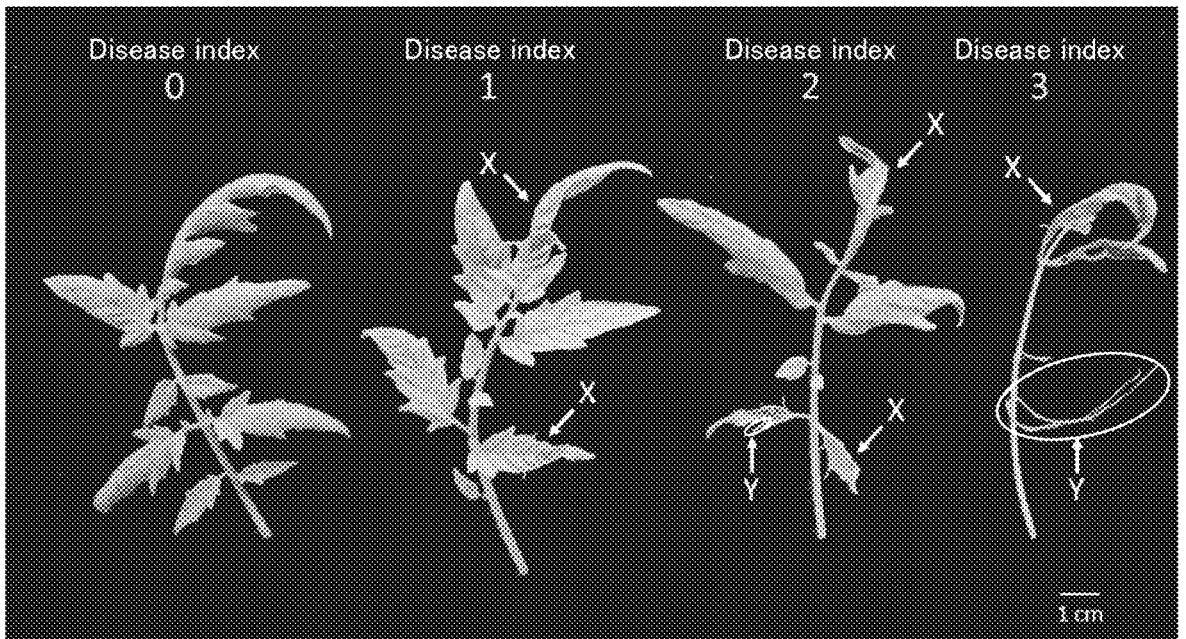
FIG. 5 is a photograph showing the criteria for evaluating the disease index of tomato plants in Example 2.

In the disease investigation, the disease index was evaluated in accordance with the following criteria. As the evaluation criteria for the disease index, the photographs of FIGS. 5A to 5C show representative examples of individuals with disease indices of 0 to 3 (each of the photographs was obtained by inoculating the cotyledons of tomatoes with ToBRFV and taking photographs of the non-inoculated upper leaves 21 days later). In FIGS. 5A to 5C, portions indicated by the arrows X are portions where atrophy of leaves are observed, and regions indicated by the arrows Y are regions where filiform leaf symptoms are observed.

Disease index 0: no symptoms are observed
Disease index 1: slight leaf atrophy
Disease index 2: slight filiform leaf and leaf atrophy
Disease index 3: distinct filiform leaf and leaf atrophy Then, the disease indices of the respective individuals were investigated in accordance with the above-described criteria, and the severity of each line was determined according to the following equation.

$$\text{Severity}(N) = [(0 \times n_0) + (1 \times n_1) + (2 \times n_2) + (3 \times n_3)]/\text{the number of the investigated individuals}$$

In the above equation, "0, 1, 2, and 3" each indicate the disease index, and "$n_0$, $n_1$, $n_2$, and $n_3$" indicate the number of individuals evaluated as having a disease index of 0, a disease index of 1, a disease index of 2, and a disease index of 3, respectively.

The results are summarized in Table 2 below. Table 2 shows the number of individuals and severity for each disease index in a tomato plant of each genotype. As summarized in Table 2, it was found that the tomato plants had a severity of less than 1 and were strongly resistant to ToBRFV when they were the triple-mutant Δaaccdd or the quadruple mutant Δaabbccdd.

TABLE 2

| Genotype | Disease index | | | | Severity |
| | 0 | 1 | 2 | 3 | |
|---|---|---|---|---|---|
| Δaabbcc | 0 | 3 | 5 | 0 | 1.6 |
| Δaabbdd | 0 | 0 | 0 | 4 | 3 |
| Δaaccdd | 8 | 0 | 0 | 0 | 0 |
| Δbbccdd | 0 | 2 | 2 | 0 | 1.5 |
| Δaabbccdd | 8 | 0 | 0 | 0 | 0 |
| Wild-type | 0 | 0 | 0 | 6 | 3 |

(2) Evaluation of Resistance by Disease Index-2

Next, the severity was evaluated in the same manner as in Example 2(1), except that the mutations ΔaaBBccDD (ww), ΔaaBbccDD (hw), ΔaabbccDD (mw), ΔaaBBccDd (wh), ΔaaBbccDd (hh), ΔaabbccDd (mh), ΔaaBBccdd (wm), and ΔaaBbccdd (hm) were used instead of the wild-type strain and the triple-mutants Δaabbcc, Δaabbdd, Δaaccdd, and Δbbccdd. Note that A means the wild-type SlTOM1a gene, B means the wild-type SlTOM1b gene, C means the wild-type SlTOM1c gene, and D means the wild-type SlTOM1d gene. The results are summarized in Table 3 below.

TABLE 3

| Genotype | Disease index | | | | Severity |
|---|---|---|---|---|---|
| | 0 | 1 | 2 | 3 | |
| ΔaaBBccDD (ww) | 0 | 0 | 0 | 7 | 3 |
| ΔaaBbccDD (hw) | 0 | 0 | 1 | 4 | 2.8 |
| ΔaabbccDD (mw) | 0 | 2 | 7 | 2 | 2 |
| ΔaaBBccDd (wh) | 0 | 0 | 4 | 2 | 2.3 |
| ΔaaBbccDd (hh) | 0 | 5 | 3 | 0 | 1.4 |
| ΔaabbccDd (mh) | 15 | 0 | 0 | 0 | 0 |
| ΔaaBBccdd (wm) | 15 | 0 | 0 | 0 | 0 |
| ΔaaBbccdd (hm) | 7 | 0 | 0 | 0 | 0 |
| Δaabbccdd (mm) | 4 | 0 | 0 | 0 | 0 |

Table 3 shows the number of individuals and severity for each disease index in a tomato plant of each genotype. As summarized in Table 3, it was found that the tomato plants had a severity of less than 1 and were strongly resistant to ToBRFV when they were the mutants ΔaabbccDd (mh), ΔaaBBccdd (wm), ΔaaBbccdd (hm), and Δaabbccdd (mm).
(3) Evaluation of ToBRFV Genomic RNA Accumulation Amount One non-inoculated upper leaf was collected from each individual of the wild-type strain on day 14 after inoculation with ToBRFV in Example 2(1). In addition, one non-inoculated upper leaf was cut from each individual of each mutant on day 14 after inoculation with ToBRFV in Example 2(2), and collected into a 1.5 ml centrifuge tube containing two zirconia balls (3 mm in diameter). The non-inoculated upper leaf was frozen in liquid nitrogen for each tube, then grinding (Qiagen Tissue Lyser, one set of "28 times per second for 15 seconds" was performed 2 times) was performed, and total RNA was extracted using an RNA-extracting reagent (RNAiso Plus, manufactured by TaKaRa Co., Ltd.), then purified, and recovered. Total RNA was dissolved in water and the concentration of total RNA was calculated from the absorbance at 260 nm.

Figure 6:
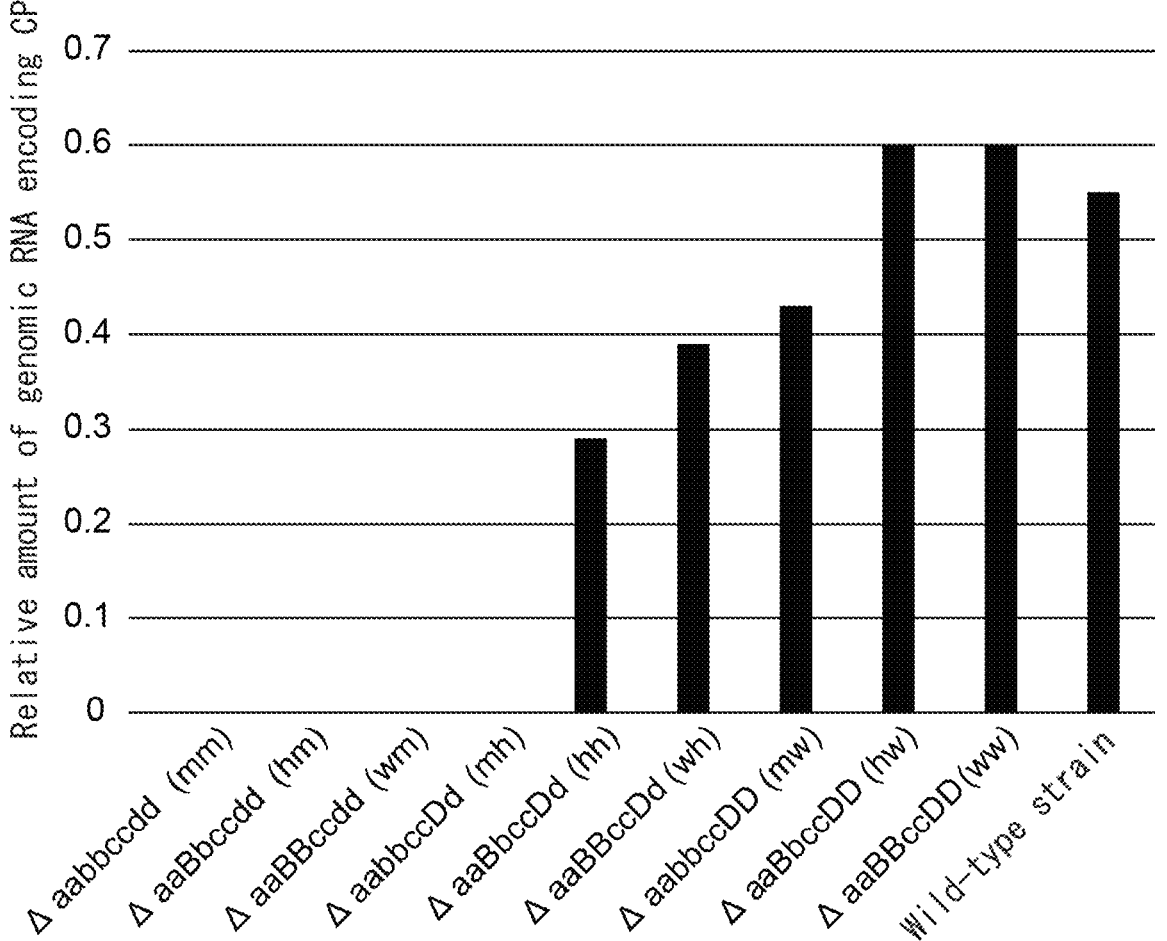
FIG. 6 is a graph showing the relative amount of genomic RNA encoding CP in Example 2.

Next, for the total RNA obtained, ToBRFV genomic RNA was quantified by Northern blotting using the following probe complementary to the regions encoding coat proteins (CPs). Note that the probe corresponds to a complementary strand of 5713rd to 6019th nucleotides of ToBRFV genomic RNA (GenBank: KX619418), and the region is a part of the region encoding the coat protein (CP). The probe is labeled with $^{32}$P as described below. The Northern blotting was specifically performed by the following procedure: First, the purified RNA was denatured by glyoxal, and after fractionation by 1% agarose gel electrophoresis, the resultant was transferred to a nylon membrane (Hybond N+, manufactured by GE Healthcare Co., Ltd.) and fixed by ultraviolet irradiation (Sambrook et al., ed. Molecular Cloning: A Laboratory Manual 2$^{nd}$ Ed.) [Cold Spring Harbor Laboratory Press (1989)]). Then, the resultant was hybridized with the RNA probe labeled with 32P in a hybridization buffer (PerfectHyb Plus manufactured by Sigma) at 68° C. for 16 hours, followed by washing in 2×SSC with 1% SDS at 68° C., and the 32P signal was detected and quantified using an image analyzer (Typhoon, manufactured by GE Healthcare). The RNA probe labeled with $^{32}$P was synthesized with T7 RNA polymerase in the presence of $^{32}$P-CTP using a template DNA fragment that was amplified by PCR from a plasmid containing ToBRFV cDNA synthesized from ToBRFV genomic RNA (GenBank: KX619418) using the following primer set. The underlined base sequence in T7_ToBRFV6019R below is the promoter of T7 RNA polymerase, and the G at the 3' end is the base at the reading start position (6019th nucleotide of ToBRFV genomic RNA). The total RNA amount subjected to Northern blotting was then used to correct $^{32}$P signal in the non-inoculated upper leaf of each mutant. With respect to the resulting correction value, the average value of each individual of each genotype was calculated. The results are shown in FIG. 6.
(Probe for CP Detection)

(SEQ ID NO: 24)
5'-GGGUUCGCCUGAUUUUCGACUUCUAUAAUCCU

AUUUCUAGUAUCGAAAGCUCCUAACAAAGCAGUAA

CUAGAGGAUCUAGUACCGCAUUGUACCUAUACACC

UUAAAACCACUGUCAGGAAACCUAACAGUGACUUG

AGGGACAGGUUUCCACACUUCGCUAAAUUGCCGUU

GAACGGUUGUUCUAGCUUGUUGUGUUUGGAACUGA

UUACCUAGUGAAUUAGUACAUAAAUUUAUUAAUUC

UAUAGGGUCGGCCCAUGCUGAUGACAAAAACACAA

AUUGCGAUGGAGUUGCGAUUGUGUAAGACA-3'

(Primer Set for Probe)
Forward primer: ToBRFV 5713 F (SEQ ID NO: 25)
5'-TGTCTTACACAATCGCAACTCC-3'

Reverse primer: T7_ToBRFV6019R (SEQ ID NO: 26)
5'-CGTACGTAATACGACTCACTATAG

GGTTCGCCTGATTTTCGACTT-3'

FIG. 6 is a graph showing the relative amount of genomic RNA encoding CP. In FIG. 6, the horizontal axis indicates the type of the mutant, and the vertical axis indicates the relative amount of the genomic RNA. As shown in FIG. 6, genomic RNA encoding CP of ToBRFV was not observed in the tomato plants when they were mutants ΔaabbccDd (mh), ΔaaBBccdd (wm), ΔaaBbccdd (hm), and Δaabbccdd (mm). The results were in good agreement with the disease symptoms of Examples 2(1) and 2(2).

From the above, it was found that the tomato plant of the present invention is resistant to Tobamovirus.

While the present invention has been described above with reference to illustrative embodiments, the present invention is by no means limited thereto. Various changes and variations that may become apparent to those skilled in the art may be made in the configuration and specifics of the present invention without departing from the scope of the present invention.

This application claims priority from Japanese Patent Application No. 2020-021960 filed on Feb. 12, 2020 and Japanese Patent Application No. 2020-087665 filed on May 19, 2020. The entire disclosure of these Japanese patent applications is incorporated herein by reference.

SUPPLEMENTARY NOTES

Some or all of the above embodiments and examples may be described as in the following Supplementary Notes, but are not limited thereto.

Supplementary Note 1

A *Tobamovirus* resistant tomato plant with loss of function for a SlTOM1a gene, a SlTOM1c gene, and a SlTOM1d gene.

Supplementary Note 2

The tomato plant according to Supplementary Note 1, wherein
the SlTOM1a gene is a *Tobamovirus* resistance control gene including the following polynucleotide (NA):
(NA) any of the following polynucleotides (NA1) to (NA7):
(NA1) a polynucleotide consisting of a base sequence of SEQ ID NO: 1 or 2;
(NA2) a polynucleotide consisting of a base sequence obtained by deletion, substitution, insertion, and/or addition of one or several bases in a base sequence of the polynucleotide (NA1), and encoding a protein having *Tobamovirus* resistance control activity;
(NA3) a polynucleotide consisting of a base sequence having at least 90% sequence identity to the base sequence of the polynucleotide (NA1), and encoding a protein having *Tobamovirus*
(NA4) a polynucleotide consisting of a base sequence complementary to a polynucleotide that hybridizes to a polynucleotide consisting of the base sequence of the polynucleotide (NA1) under stringent conditions, and encoding a protein having *Tobamovirus* resistance control activity;
(NA5) a polynucleotide encoding a protein consisting of an amino acid sequence of SEQ ID NO: 3;
(NA6) a polynucleotide consisting of an amino acid sequence obtained by deletion, substitution, insertion, and/or addition of one or several amino acids in the amino acid sequence of SEQ ID NO: 3, and encoding a protein having *Tobamovirus* resistance control activity; and
(NA7) a polynucleotide consisting of an amino acid sequence having at least 90% sequence identity to the amino acid sequence of SEQ ID NO: 3, and encoding a protein having *Tobamovirus* resistance control activity.

Supplementary Note 3

The tomato plant according to Supplementary Note 1 or 2, wherein
the SlTOM1c gene is a *Tobamovirus* resistance control gene including the following polynucleotide (NC):
(NC) any of the following polynucleotides (NC1) to (NC7):
(NC1) a polynucleotide consisting of a base sequence of SEQ ID NO:7 or 8;
(NC2) a polynucleotide consisting of a base sequence obtained by deletion, substitution, insertion, and/or addition of one or several bases in a base sequence of the polynucleotide (NC1), and encoding a protein having *Tobamovirus* resistance control activity;
(NC3) a polynucleotide consisting of a base sequence having at least 90% sequence identity to the base sequence of the polynucleotide (NC1), and encoding a protein having *Tobamovirus* resistance control activity;
(NC4) a polynucleotide consisting of a base sequence complementary to a polynucleotide that hybridizes to a polynucleotide consisting of the base sequence of the polynucleotide (NC1) under stringent conditions, and encoding a protein having *Tobamovirus* resistance control activity;
(NC5) a polynucleotide encoding a protein consisting of an amino acid sequence of SEQ ID NO: 9;

(NC6) a polynucleotide consisting of an amino acid sequence obtained by deletion, substitution, insertion, and/or addition of one or several amino acids in the amino acid sequence of SEQ ID NO: 9, and encoding a protein having *Tobamovirus* resistance control activity; and
(NC7) a polynucleotide consisting of an amino acid sequence having at least 90% sequence identity to an amino acid sequence of SEQ ID NO: 9, and encoding a protein having *Tobamovirus* resistance control activity.

Supplementary Note 4

The tomato plant according to any one of Supplementary Notes 1 to 3, wherein
the SlTOM1d gene is a *Tobamovirus* resistance control gene including the following polynucleotide (ND):
(ND) any of the following polynucleotides (ND1) to (ND7):
(ND1) a polynucleotide consisting of a base sequence of SEQ ID NO: 10;
(ND2) a polynucleotide consisting of a base sequence obtained by deletion, substitution, insertion, and/or addition of one or several bases in a base sequence of the polynucleotide (ND1), and encoding a protein having *Tobamovirus* resistance control activity;
(ND3) a polynucleotide consisting of a base sequence having at least 90% sequence identity to the base sequence of the polynucleotide (ND1), and encoding a protein having *Tobamovirus* resistance control activity;
(ND4) a polynucleotide consisting of a base sequence complementary to a polynucleotide that hybridizes to a polynucleotide consisting of the base sequence of the polynucleotide (ND1) under stringent conditions, and encoding a protein having *Tobamovirus* resistance control activity;
(ND5) a polynucleotide encoding a protein consisting of an amino acid sequence of SEQ ID NO: 11;
(ND6) a polynucleotide consisting of an amino acid sequence obtained by deletion, substitution, insertion, and/or addition of one or several amino acids in the amino acid sequence of SEQ ID NO: 11, and encoding a protein having *Tobamovirus* resistance control activity; and
(ND7) a polynucleotide consisting of an amino acid sequence having at least 90% sequence identity to the amino acid sequence of SEQ ID NO: 11, and encoding a protein having *Tobamovirus* resistance control activity.

Supplementary Note 5

The tomato plant according to any one of Supplementary Notes 1 to 4, including:
a loss-of-function gene for a SlTOM1a gene, a loss-of-function gene for a SlTOM1c gene, and a loss-of-function gene for a SlTOM1d gene in a homozygous form.

Supplementary Note 6

The tomato plant according to any one of Supplementary Notes 1 to 5 with loss of function for a SlTOM1b gene.

Supplementary Note 7

The tomato plant according to Supplementary Note 6, wherein
the SlTOM1b gene is a *Tobamovirus* resistance control gene including the following polynucleotide (NB):
(NB) any of the following polynucleotides (NB1) to (NB7):

(NB1) a polynucleotide consisting of a base sequence of SEQ ID NO: 4 or 5;

(NB2) a polynucleotide consisting of a base sequence obtained by deletion, substitution, insertion, and/or addition of one or several bases in a base sequence of the polynucleotide (NB1), and encoding a protein having *Tobamovirus* resistance control activity;

(NB3) a polynucleotide consisting of a base sequence having at least 90% sequence identity to the base sequence of the polynucleotide (NB1), and encoding a protein having *Tobamovirus* resistance control activity;

(NB4) a polynucleotide consisting of a base sequence complementary to a polynucleotide that hybridizes to a polynucleotide consisting of the base sequence of the polynucleotide (NB1) under stringent conditions, and encoding a protein having *Tobamovirus* resistance control activity;

(NB5) a polynucleotide encoding a protein consisting of an amino acid sequence of SEQ ID NO: 6;

(NB6) a polynucleotide consisting of an amino acid sequence obtained by deletion, substitution, insertion, and/or addition of one or several amino acids in the amino acid sequence of SEQ ID NO: 6, and encoding a protein having *Tobamovirus* resistance control activity; and (NB7) a polynucleotide consisting of an amino acid sequence having at least 90% sequence identity to the amino acid sequence of SEQ ID NO: 6, and encoding a protein having *Tobamovirus* resistance control activity.

Supplementary Note 8

The tomato plant according to Supplementary Note 6 or 7, including:
   a loss-of-function gene for a SlTOM1b gene in a homozygous form.

Supplementary Note 9

The tomato plant according to any one of Supplementary Notes 6 to 8, including:
   a loss-of-function gene for a SlTOM1a gene, a loss-of-function gene for a SlTOM1b gene, and a loss-of-function gene for a SlTOM1c gene in a homozygous form, and
   a loss-of-function gene for a SlTOM1d gene in a heterozygous form.

Supplementary Note 10

The tomato plant according to any one of Supplementary Notes 1 to 9, including:
   the loss-of-function gene(s) for the SlTOM1a gene, the SlTOM1b gene, the SlTOM1c gene, and/or the SlTOM1d gene, wherein
   the loss-of-function gene is a gene generated by deletion, substitution, insertion and/or addition of one or several bases with respect to a normal gene of each of the SlTOM1a gene, the SlTOM1b gene, the SlTOM1c gene, and/or the SlTOM1d gene.

Supplementary Note 11

The tomato plant according to any one of Supplementary Notes 1 to 10, including:
   the loss-of-function gene(s) for the SlTOM1a gene, the SlTOM1b gene, the SlTOM1c gene, and/or the SlTOM1d gene, wherein the loss-of-function gene is a gene generated by introducing a frameshift mutation into a normal gene of each of the SlTOM1a gene, the SlTOM1b gene, the SlTOM1c gene, and/or the SlTOM1d gene.

Supplementary Note 12

The tomato plant according to any one of Supplementary Notes 1 to 11, including:
   the loss-of-function gene(s) for the SlTOM1a gene, the SlTOM1b gene, the SlTOM1c gene, and/or the SlTOM1d gene, wherein
   the loss-of-function gene is a gene generated by partial deletion or complete deletion of a normal gene of each of the SlTOM1a gene, the SlTOM1b gene, the SlTOM1c gene, and/or the SlTOM1d gene.

Supplementary Note 13

The tomato plant according to any one of Supplementary Notes 1 to 12, including:
   the loss-of-function gene(s) for the SlTOM1a gene, the SlTOM1b gene, the SlTOM1c gene, and/or the SlTOM1d gene, wherein
   the loss-of-function gene is a gene generated by introducing a mutation into an exon region in a normal gene of each of the SlTOM1a gene, the SlTOM1b gene, the SlTOM1c gene, and/or the SlTOM1d gene.

Supplementary Note 14

The tomato plant according to any one of Supplementary Notes 1 to 13, wherein
   the *Tobamovirus* resistant tomato plant is a plant body or a part thereof.

Supplementary Note 15

The tomato plant according to any one of Supplementary Notes 1 to 14, wherein
   the *Tobamovirus* resistant tomato plant is a seed.

Supplementary Note 16

A method for producing a *Tobamovirus* resistant tomato plant, including the following step (a):
   (a) crossing the *Tobamovirus* resistant tomato plant according to any one of Supplementary Notes 1 to 15 with another tomato plant.

Supplementary Note 17

The production method according to Supplementary Note 16, including the following step (b):
   (b) selecting a *Tobamovirus* resistant tomato plant from one or more tomato plants obtained in the step (a) or one or more progeny lines thereof.

Supplementary Note 18

The production method according to Supplementary Note 17, wherein
   the selection in the step (b) is the selection of a *Tobamovirus* resistant tomato plant with loss of function for a SlTOM1a gene, a SlTOM1c gene, and a SlTOM1d gene.

Supplementary Note 19

The production method according to Supplementary Note 17 or 18, wherein the selection in the step (b) is the selection of a *Tobamovirus* resistant tomato plant including a loss-of-function gene for a SlTOM1a gene, a loss-of-function gene for a SlTOM1c gene, and a loss-of-function gene for a SlTOM1d gene in a homozygous form.

Supplementary Note 20

The production method according to any one of Supplementary Notes 17 to 19, wherein the selection in the step (b) is the selection of a *Tobamovirus* resistant tomato plant with loss of function for a SlTOM1b gene.

Supplementary Note 21

The production method according to Supplementary Note 20, wherein the selection in the step (b) is the selection of a *Tobamovirus* resistant tomato plant including a loss-of-function gene for a SlTOM1b gene in a homozygous form.

Supplementary Note 22

The production method according to Supplementary Note 20 or 21, wherein the selection in the step (b) is the selection of a *Tobamovirus* resistant tomato plant including a loss-of-function gene for a SlTOM1a gene, a loss-of-function gene for a SlTOM1b gene, and a loss-of-function gene for a SlTOM1c gene in a homozygous form, and a loss-of-function gene for a SlTOM1d in a heterozygous form.

Supplementary Note 23

The production method according to any one of Supplementary Notes 16 to 22, further including the following step (x) prior to the step (a):

(x) selecting the *Tobamovirus* resistant tomato plant according to any one of Supplementary Notes 1 to 15 from one or more tomato plants to be examined.

Supplementary Note 24

The production method according to Supplementary Note 23, wherein the selection in the step (x) is the selection of a *Tobamovirus* resistant tomato plant with loss of function for a SlTOM1a gene, SlTOM1c gene, and SlTOM1d gene.

Supplementary Note 25

The production method according to Supplementary Note 23 or 24, wherein the selection in the step (x) is the selection of a *Tobamovirus* resistant tomato plant including a loss-of-function gene for a SlTOM1a gene, a loss-of-function gene for a SlTOM1c gene, and a loss-of-function gene for a SlTOM1d gene in a homozygous form.

Supplementary Note 26

The production method according to any one of Supplementary Notes 23 to 25, wherein the selection in the step (x) is the selection of a *Tobamovirus* resistant tomato plant with loss of function for a SlTOM1b gene.

Supplementary Note 27

The production method according to Supplementary Note 26, wherein the selection in the step (x) is the selection of a *Tobamovirus* resistant tomato plant including a loss-of-function gene for a SlTOM1b gene in a homozygous form.

Supplementary Note 28

The production method according to Supplementary Note 26 or 27, wherein the selection in the step (x) is the selection of a *Tobamovirus* resistant tomato plant including a loss-of-function gene for a SlTOM1a gene, a loss-of-function gene for a SlTOM1b gene, and a loss-of-function gene for a SlTOM1c gene in a homozygous form, and a loss-of-function gene for a SlTOM1d gene in a heterozygous form.

Supplementary Note 29

The production method according to any one of Supplementary Notes 18, 19, 22, 24, and 25, wherein the SlTOM1a gene is a *Tobamovirus* resistance control gene including the following polynucleotide (NA):

(NA) any of the following polynucleotides (NA1) to (NA7):

(NA1) a polynucleotide consisting of a base sequence of SEQ ID NO: 1 or 2;

(NA2) a polynucleotide consisting of a base sequence obtained by deletion, substitution, insertion, and/or addition of one or several bases in a base sequence of the polynucleotide (NA1), and encoding a protein having *Tobamovirus* resistance control activity;

(NA3) a polynucleotide consisting of a base sequence having at least 90% sequence identity to the base sequence of the polynucleotide (NA1), and encoding a protein having *Tobamovirus* resistance control activity;

(NA4) a polynucleotide consisting of a base sequence complementary to a polynucleotide that hybridizes to a polynucleotide consisting of the base sequence of the polynucleotide (NA1) under stringent conditions, and encoding a protein having *Tobamovirus* resistance control activity;

(NA5) a polynucleotide encoding a protein consisting of an amino acid sequence of SEQ ID NO: 3;

(NA6) a polynucleotide consisting of an amino acid sequence obtained by deletion, substitution, insertion, and/or addition of one or several amino acids in the amino acid sequence of SEQ ID NO: 3, and encoding a protein having *Tobamovirus* resistance control activity; and (NA7) a polynucleotide consisting of an amino acid sequence having at least 90% sequence identity to the amino acid sequence of SEQ ID NO: 3, and encoding a protein having *Tobamovirus* resistance control activity.

Supplementary Note 30

The production method according to any one of Supplementary Notes 18, 19, 22, 24, and 25, wherein the SITOM1c gene is a *Tobamovirus* resistance control gene including the following polynucleotide (NC):
(NC) any of the following polynucleotides (NC1) to (NC7):
(NC1) a polynucleotide consisting of a base sequence of SEQ ID NO:7 or 8;
(NC2) a polynucleotide consisting of a base sequence obtained by deletion, substitution, insertion, and/or addition of one or several bases in the base sequence of the polynucleotide (NC1), and encoding a protein having *Tobamovirus* resistance control activity;
(NC3) a polynucleotide consisting of a base sequence having at least 90% sequence identity to the base sequence of the polynucleotide (NC1), and encoding a protein having *Tobamovirus* resistance control activity;
(NC4) a polynucleotide consisting of a base sequence complementary to a polynucleotide that hybridizes to a polynucleotide consisting of the base sequence of the polynucleotide (NC1) under stringent conditions, and encoding a protein having *Tobamovirus* resistance control activity;
(NC5) a polynucleotide encoding a protein consisting of an amino acid sequence of SEQ ID NO: 9;
(NC6) a polynucleotide consisting of an amino acid sequence obtained by deletion, substitution, insertion, and/or addition of one or several amino acids in the amino acid sequence of SEQ ID NO: 9, and encoding a protein having *Tobamovirus* resistance control activity; and
(NC7) a polynucleotide consisting of an amino acid sequence having at least 90% sequence identity to an amino acid sequence of SEQ ID NO: 9, and encoding a protein having *Tobamovirus* resistance control activity.

Supplementary Note 31

The production method according to any one of Supplementary Notes 18, 19, 22, 24, and 25, wherein
the SITOM1d gene is a *Tobamovirus* resistance control gene including the following polynucleotide (ND):
(ND) any of the following polynucleotides (ND1) to (ND7):
(ND1) a polynucleotide consisting of a base sequence of SEQ ID NO: 10;
(ND2) a polynucleotide consisting of a base sequence obtained by deletion, substitution, insertion, and/or addition of one or several bases in a base sequence of the polynucleotide (ND1), and encoding a protein having *Tobamovirus* resistance control activity;
(ND3) a polynucleotide consisting of a base sequence having at least 90% sequence identity to the base sequence of the polynucleotide (ND1), and encoding a protein having *Tobamovirus* resistance control activity;
(ND4) a polynucleotide consisting of a base sequence complementary to a polynucleotide that hybridizes to a polynucleotide consisting of the base sequence of the polynucleotide (ND1) under stringent conditions, and encoding a protein having *Tobamovirus* resistance control activity;
(ND5) a polynucleotide encoding a protein consisting of an amino acid sequence of SEQ ID NO: 11;
(ND6) a polynucleotide consisting of an amino acid sequence obtained by deletion, substitution, insertion, and/or addition of one or several amino acids in the amino acid sequence of SEQ ID NO: 11, and encoding a protein having *Tobamovirus* resistance control activity; and
(ND7) a polynucleotide consisting of an amino acid sequence having at least 90% sequence identity to the amino acid sequence of SEQ ID NO: 11, and encoding a protein having *Tobamovirus* resistance control activity.

Supplementary Note 32

The production method according to any one of Supplementary Notes 20 to 22 and 26 to 28, wherein
the SITOM1b gene is a *Tobamovirus* resistance control gene including the following polynucleotide (NB):
(NB) any of the following polynucleotides (NB1) to (NB7):
(NB1) a polynucleotide consisting of a base sequence of SEQ ID NO: 4 or 5;
(NB2) a polynucleotide consisting of a base sequence obtained by deletion, substitution, insertion, and/or addition of one or several bases in a base sequence of the polynucleotide (NB1), and encoding a protein having *Tobamovirus* resistance control activity;
(NB3) a polynucleotide consisting of a base sequence having at least 90% sequence identity to the base sequence of the polynucleotide (NB1), and encoding a protein having *Tobamovirus* resistance control activity;
(NB4) a polynucleotide consisting of a base sequence complementary to a polynucleotide that hybridizes to a polynucleotide consisting of the base sequence of the polynucleotide (NB1) under stringent conditions, and encoding a protein having *Tobamovirus* resistance control activity;
(NB5) a polynucleotide encoding a protein consisting of an amino acid sequence of SEQ ID NO: 6;
(NB6) a polynucleotide consisting of an amino acid sequence obtained by deletion, substitution, insertion, and/or addition of one or several amino acids in the amino acid sequence of SEQ ID NO: 6, and encoding a protein having *Tobamovirus* resistance control activity; and
(NB7) a polynucleotide consisting of an amino acid sequence having at least 90% sequence identity to the amino acid sequence of SEQ ID NO: 6, and encoding a protein having *Tobamovirus* resistance control activity.

Supplementary Note 33

The production method according to any one of Supplementary Notes 18 to 22 and 24 to 28, wherein
the *Tobamovirus* resistant tomato plant includes the loss-of-function gene(s) for the SITOM1a gene, the SITOM1b gene, the SITOM1c gene, and/or the SITOM1d gene, and
the loss-of-function gene is a gene generated by deletion, substitution, insertion and/or addition of one or several bases with respect to a normal gene of each of the SITOM1a gene, the SITOM1b gene, the SITOM1c gene, and/or the SITOM1d gene.

Supplementary Note 34

The production method according to any one of Supplementary Notes 18 to 22, 24 to 28, and 33, wherein
the *Tobamovirus* resistant tomato plant includes the loss-of-function gene(s) for the SITOM1a gene, the SITOM1b gene, the SITOM1c gene, and/or the SITOM1d gene, and
the loss-of-function gene is a gene generated by introducing a frameshift mutation into a normal gene of each of the SITOM1a gene, the SITOM1b gene, the SITOM1c gene, and/or the SITOM1d gene.

Supplementary Note 35

The production method according to any one of Supplementary Notes 18 to 22, 24 to 28, 33, and 34, wherein
the *Tobamovirus* resistant tomato plant includes the loss-of-function gene(s) for the SITOM1a gene, the SITOM1b gene, the SITOM1c gene, and/or the SITOM1d gene, and the loss-of-function gene is a gene generated by partial deletion or complete deletion of a normal gene of each of the SlTOM1a gene, the SlTOM1b gene, the SlTOM1c gene, and/or the SlTOM1d gene.

Supplementary Note 36

The production method according to any one of Supplementary Notes 18 to 22, 24 to 28, 33, and 33 to 35, wherein
 the Tobamovirus resistant tomato plant includes the loss-of-function gene(s) for the SlTOM1a gene, the SlTOM1b gene, the SlTOM1c gene, and/or the SlTOM1d gene, and
 the loss-of-function gene is a gene generated by introducing a mutation into an exon region in a normal gene of each of the SlTOM1a gene, the SlTOM1b gene, the SlTOM1c gene, and/or the SlTOM1d gene.

Supplementary Note 37

A method for imparting Tobamovirus resistance to a tomato plant, including the step of:
 causing loss of function for a SlTOM1a gene, a SlTOM1c gene, and a SlTOM1d gene of a target tomato plant.

Supplementary Note 38

The imparting method according to Supplementary Note 37, wherein
 in the causing loss of function, loss-of-function mutations are introduced into a pair of SlTOM1a genes, a pair of SlTOM1c genes, and a pair of SlTOM1d genes.

Supplementary Note 39

The imparting method according to Supplementary Note 37 or 38, wherein
 in the causing loss of function, a loss-of-function mutation is introduced into a SlTOM1b gene of a target tomato plant.

Supplementary Note 40

The imparting method according to Supplementary Note 39, wherein
 in the causing loss of function, loss-of-function mutations are introduced into a pair of SlTOM1b genes.

Supplementary Note 41

The imparting method according to Supplementary Note 39 or 40, wherein
 in the causing loss of function, loss-of-function mutation(s) is introduced into one of a pair of SlTOM1a genes, one of a pair of SlTOM1b genes, one of a pair of SlTOM1c genes, and/or one of a pair of SlTOM1d genes.

Supplementary Note 42

The imparting method according to any one of Supplementary Notes 37 to 41, wherein
 in the causing loss of function, a loss-of-function mutation is introduced by deletion, substitution, insertion and/or addition of one or several bases with respect to the base sequence of each of the SlTOM1a gene, the SlTOM1b gene, the SlTOM1c gene, and/or the SlTOM1d gene.

Supplementary Note 43

The imparting method according to any one of Supplementary Notes 37 to 42, wherein
 in the causing loss of function, a loss-of-function mutation is introduced by introducing a frameshift mutation into each of the SlTOM1a gene, the SlTOM1b gene, the SlTOM1c gene, and/or the SlTOM1d gene.

Supplementary Note 44

The imparting method according to any one of Supplementary Notes 37 to 43, wherein
 in the causing loss of function, a loss-of-function mutation is introduced by partial deletion or complete deletion of a normal gene of each of the SlTOM1a gene, the SlTOM1b gene, the SlTOM1c gene, and/or the SlTOM1d gene.

Supplementary Note 45

The imparting method according to any one of Supplementary Notes 37 to 44, wherein
 in the causing loss of function, a loss-of-function mutation is introduced by introducing a mutation into an exon region in a normal gene of each of the SlTOM1a gene, the SlTOM1b gene, the SlTOM1c gene, and/or the SlTOM1d gene.

Supplementary Note 46

The imparting method according to any one of Supplementary Notes 37 to 45, wherein
 in the causing loss of function, a mutation is introduced so as to include the loss-of-function gene(s) for the SlTOM1a gene, the SlTOM1b gene, the SlTOM1c gene, and/or the SlTOM1d gene in a homozygous form.

Supplementary Note 47

The imparting method according to any one of Supplementary Notes 37 to 46, including the step of:
 selecting a Tobamovirus resistant tomato plant from one or more tomato plants obtained in the causing loss of function or one or more progeny lines thereof.

Supplementary Note 48

A method for producing a Tobamovirus resistant tomato plant, including the step of:
 imparting Tobamovirus resistance to a target tomato plant, wherein
 the imparting is carried out by the method for imparting Tobamovirus resistance to a tomato plant according to any one of Supplementary Notes 37 to 47.

Supplementary Note 49

A method for screening a Tobamovirus resistant tomato plant, including the step of:
 selecting a tomato plant to be examined with loss of function for a SlTOM1a gene, a SlTOM1c gene, and a SITOM1d gene from one or more tomato plants to be examined as a *Tobamovirus* resistant tomato plant.

Supplementary Note 50

The screening method according to Supplementary Note 49, wherein in the selecting, a tomato plant to be examined including a loss-of-function gene for a SITOM1a gene, a loss-of-function gene for a SITOM1c gene, and a loss-of-function gene for a SITOM1d gene in a homozygous form is selected as a *Tobamovirus* resistant tomato plant.

Supplementary Note 51

The screening method according to Supplementary Note 49 or 50, wherein in the selecting, a tomato plant to be examined with loss of function for a SITOM1b gene is selected as a *Tobamovirus* resistant tomato plant.

Supplementary Note 52

The screening method according to Supplementary Note 51, wherein in the selecting, a tomato plant to be examined including a loss-of-function gene for a SITOM1b gene in a homozygous form is selected as a *Tobamovirus* resistant tomato plant.

Supplementary Note 53

The screening method according to Supplementary Note 51 or 52, wherein in the selecting, a tomato plant to be examined including a loss-of-function gene for a SITOM1a gene, a loss-of-function gene for a SITOM1b gene, and a loss-of-function gene for a SITOM1c gene in a homozygous form, and a loss-of-function gene for a SITOM1d gene in a heterozygous form is selected as a *Tobamovirus* resistant tomato plant.

Supplementary Note 54

The screening method according to any one of Supplementary Notes 49 to 53, wherein in the selecting, a tomato plant to be examined including a gene generated by deletion, substitution, insertion and/or addition of one or several bases with respect to a normal gene of each of the SITOM1a gene, the SITOM1b gene, the SITOM1c gene, and/or the SITOM1d gene is selected as a *Tobamovirus* resistant tomato plant.

Supplementary Note 55

The screening method according to any one of Supplementary Notes 49 to 54, wherein in the selecting, a tomato plant to be examined including a gene generated by introducing a frameshift mutation into a normal gene of each of the SITOM1a gene, the SITOM1b gene, the SITOM1c gene, and/or the SITOM1d gene is selected as a *Tobamovirus* resistant tomato plant.

Supplementary Note 56

The screening method according to any one of Supplementary Notes 49 to 55, wherein in the selecting, a tomato plant to be examined including a gene generated by partial deletion or complete deletion of a normal gene of each of the SITOM1a gene, the SITOM1b gene, the SITOM1c gene, and/or the SITOM1d gene is selected as a *Tobamovirus* resistant tomato plant.

Supplementary Note 57

The screening method according to any one of Supplementary Notes 49 to 56, wherein in the selecting, a tomato plant to be examined including a gene generated by introducing a mutation into an exon region in a normal gene of each of the SITOM1a gene, the SITOM1b gene, the SITOM1c gene, and/or the SITOM1d gene is selected as a *Tobamovirus* resistant tomato plant.

Supplementary Note 58

A method for producing a *Tobamovirus* resistant tomato plant, including the step of:

screening a tomato plant to be examined with loss of function for a SITOM1a gene, a SITOM1c gene, and a SITOM1d gene from one or more tomato plants to be examined, wherein the screening is carried out by the method for screening a *Tobamovirus* resistant tomato plant according to any one of Supplementary Notes 49 to 57.

Supplementary Note 59

A *Tobamovirus* resistant tomato plant obtained by the method for producing a *Tobamovirus* resistant tomato plant according to any one of Supplementary Notes 16 to 36, 48, and 58.

Supplementary Note 60

A method for detecting *Tobamovirus* resistance in a tomato plant, including the step of:

detecting whether or not a SITOM1a gene, a SITOM1c gene, and a SITOM1d gene lose function in a tomato plant to be examined.

Supplementary Note 61

The detection method according to Supplementary Note 60, wherein the detecting includes detecting whether or not a loss-of-function gene for a SITOM1a gene, a loss-of-function gene for a SITOM1c gene, and a loss-of-function gene for a SITOM1d gene are present in a homozygous form in the tomato plant to be examined.

Supplementary Note 62

The detection method according to Supplementary Note 60 or 61, wherein the detecting includes detecting whether or not the tomato plant to be examined is with loss of function for a SITOM1b gene.

Supplementary Note 63

The detection method according to Supplementary Note 62, wherein
  the detecting includes detecting whether or not a loss-of-function gene for a SlTOM1b gene is present in a homozygous form in the tomato plant to be examined.

Supplementary Note 64

The detection method according to Supplementary Note 62 or 63, wherein
  the detecting includes detecting whether or not a loss-of-function gene for a SlTOM1a gene, a loss-of-function gene for a SlTOM1b gene, and a loss-of-function gene for a SlTOM1c gene are present in a homozygous form, and a loss-of-function gene for a SlTOM1d gene is present in a heterozygous form in the tomato plant to be examined.

Supplementary Note 65

The detection method according to any one of Supplementary Notes 60 to 64, wherein
  the detecting includes detecting whether or not including a gene generated by deletion, substitution, insertion and/or addition of one or several bases with respect to a normal gene of each of the SlTOM1a gene, the SlTOM1b gene, the SlTOM1c gene, and/or the SlTOM1d gene.
(Supplementary note 66)
The detection method according to any one of Supplementary Notes 60 to 65, wherein
  the detecting includes detecting whether or not including a gene generated by introducing a frameshift mutation into a normal gene of each of the SlTOM1a gene, the SlTOM1b gene, the SlTOM1c gene, and/or the SlTOM1d gene.

Supplementary Note 67

The detection method according to any one of Supplementary Notes 60 to 66, wherein
  the detecting includes detecting whether or not including a gene generated by partial deletion or complete deletion of a normal gene of each of the SlTOM1a gene, the SlTOM1b gene, the SlTOM1c gene, and/or the SlTOM1d gene.

Supplementary Note 68

The detection method according to any one of Supplementary Notes 60 to 67, wherein
  the detecting includes detecting whether or not including a gene generated by introducing a mutation into an exon region in a normal gene of each of the SlTOM1a gene, the SlTOM1b gene, the SlTOM1c gene, and/or the SlTOM1d gene.

Supplementary Note 69

A tomato plant processed food using the *Tobamovirus* resistant tomato plant according to any one of Supplementary Notes 1 to 15 and 59.

INDUSTRIAL APPLICABILITY

As described above, the tomato plant of the present invention is also resistant to ToBRFV. Accordingly, the present invention is extremely useful in, for example, a breeding field, an agricultural field, and the like.

SEQUENCE LISTING

20200910_TF20001WO_Sequence listing_ST25.txt

The invention claimed is:

1. A method for producing a *Tobamovirus* resistant tomato plant, comprising the following step (a):
   (a) crossing a *Tobamovirus* resistant tomato plant with another tomato plant,
   wherein the *Tobamovirus* resistant tomato plant comprises a loss-of-function for a *Solanum lycopersicum* TOM1a (SlTOM1a) gene, a *Solanum lycopersicum* TOM1c (SlTOM1c) gene, and a *Solanum lycopersicum* TOM1d (SlTOM1d) gene, wherein
   the SlTOM1a gene is a *Tobamovirus* resistance control gene comprising the following polynucleotide (NA):
   (NA) any of the following polynucleotides (NA1) to (NA3) and (NA5) to (NA7):
   (NA1) a polynucleotide consisting of a base sequence of SEQ ID NO: 1 or 2;
   (NA2) a polynucleotide consisting of a base sequence obtained by deletion, substitution, insertion, and/or addition of 1 to 26 bases in a base sequence of the polynucleotide (NA1), and encoding a protein having *Tobamovirus* resistance control activity;

(NA3) a polynucleotide consisting of a base sequence having at least 98% sequence identity to the base sequence of the polynucleotide (NA1), and encoding a protein having *Tobamovirus* resistance control activity;
   (NA5) a polynucleotide encoding a protein consisting of an amino acid sequence of SEQ ID NO: 3;
   (NA6) a polynucleotide encoding a protein consisting of an amino acid sequence obtained by deletion, substitution, insertion, and/or addition of 1 to 6 amino acids in the amino acid sequence of SEQ ID NO: 3, and having *Tobamovirus* resistance control activity; and
   (NA7) a polynucleotide encoding a protein consisting of an amino acid sequence having at least 98% sequence identity to the amino acid sequence of SEQ ID NO: 3, and having *Tobamovirus* resistance control activity,
   the SlTOM1c gene is a *Tobamovirus* resistance control gene comprising the following polynucleotide (NC):

(NC) any of the following polynucleotides (NC1) to (NC3) and (NC5) to (NC7):

(NC1) a polynucleotide consisting of a base sequence of SEQ ID NO:7 or 8;

(NC2) a polynucleotide consisting of a base sequence obtained by deletion, substitution, insertion, and/or addition of 1 to 26 bases in a base sequence of the polynucleotide (NC1), and encoding a protein having *Tobamovirus* resistance control activity;

(NC3) a polynucleotide consisting of a base sequence having at least 98% sequence identity to the base sequence of the polynucleotide (NC1), and encoding a protein having *Tobamovirus* resistance control activity;

(NC5) a polynucleotide encoding a protein consisting of an amino acid sequence of SEQ ID NO: 9;

(NC6) a polynucleotide encoding a protein consisting of an amino acid sequence obtained by deletion, substitution, insertion, and/or addition of 1 to 6 amino acids in the amino acid sequence of SEQ ID NO: 9, and having *Tobamovirus* resistance control activity; and (NC7) a polynucleotide encoding a protein consisting of an amino acid sequence having at least 98% sequence identity to the amino acid sequence of SEQ ID NO: 9, and having *Tobamovirus* resistance control activity, the SITOM1d gene is a *Tobamovirus* resistance control gene comprising the following polynucleotide (ND):

(ND) any of the following polynucleotides (ND1) to (ND3) and (ND5) to (ND7):

(ND1) a polynucleotide consisting of a base sequence of SEQ ID NO: 10;

(ND2) a polynucleotide consisting of a base sequence obtained by deletion, substitution, insertion, and/or addition of 1 to 26 bases in a base sequence of the polynucleotide (ND1), and encoding a protein having *Tobamovirus* resistance control activity;

(ND3) a polynucleotide consisting of a base sequence having at least 98% sequence identity to the base sequence of the polynucleotide (ND1), and encoding a protein having *Tobamovirus* resistance control activity;

(ND5) a polynucleotide encoding a protein consisting of an amino acid sequence of SEQ ID NO: 11;

(ND6) a polynucleotide consisting of an amino acid sequence obtained by deletion, substitution, insertion, and/or addition of 1 to 6 amino acids in the amino acid sequence of SEQ ID NO: 11, and encoding a protein having *Tobamovirus* resistance control activity; and (ND7) a polynucleotide consisting of an amino acid sequence having at least 98% sequence identity to the amino acid sequence of SEQ ID NO: 11, and encoding a protein having *Tobamovirus* resistance control activity, the *Tobamovirus* is Tomato mosaic virus (ToMV), or Tomato brown rugose fruit virus (ToBRFV), and the loss of function for the SITOM1a gene, the SITOM1c gene, and the SITOM1d gene is caused by introducing deletion, substitution, insertion, and/or addition of nucleotides into said genes itself.

2. The production method according to claim 1, comprising the following step (b):

(b) selecting for a *Tobamovirus* resistant tomato plant from one or more tomato plants obtained in the step (a) or one or more progeny lines thereof.

3. The production method according to claim 1, further comprising the following step (x) prior to the step (a):

(x) selecting for the *Tobamovirus* resistant tomato plant from one or more tomato plants to be examined.

4. A method for screening a *Tobamovirus* resistant tomato plant, comprising the step of:

selecting for a tomato plant to be examined with loss of function for a SITOM1a gene, a SITOM1c gene, and a SITOM1d gene from one or more tomato plants to be examined as a *Tobamovirus* resistant tomato plant, wherein the SITOM1a gene is a *Tobamovirus* resistance control gene comprising the following polynucleotide (NA):

(NA) any of the following polynucleotides (NA1) to (NA3) and (NA5) to (NA7):

(NA1) a polynucleotide consisting of a base sequence of SEQ ID NO: 1 or 2;

(NA2) a polynucleotide consisting of a base sequence obtained by deletion, substitution, insertion, and/or addition of 1 to 26 bases in a base sequence of the polynucleotide (NA1), and encoding a protein having *Tobamovirus* resistance control activity;

(NA3) a polynucleotide consisting of a base sequence having at least 98% sequence identity to the base sequence of the polynucleotide (NA1), and encoding a protein having *Tobamovirus* resistance control activity;

(NA5) a polynucleotide encoding a protein consisting of an amino acid sequence of SEQ ID NO: 3;

(NA6) a polynucleotide encoding a protein consisting of an amino acid sequence obtained by deletion, substitution, insertion, and/or addition of 1 to 6 amino acids in the amino acid sequence of SEQ ID NO: 3, and having *Tobamovirus* resistance control activity; and (NA7) a polynucleotide encoding a protein consisting of an amino acid sequence having at least 98% sequence identity to the amino acid sequence of SEQ ID NO: 3, and having *Tobamovirus* resistance control activity, the SITOM1c gene is a *Tobamovirus* resistance control gene comprising the following polynucleotide (NC):

(NC) any of the following polynucleotides (NC1) to (NC3) and (NC5) to (NC7):

(NC1) a polynucleotide consisting of a base sequence of SEQ ID NO:7 or 8;

(NC2) a polynucleotide consisting of a base sequence obtained by deletion, substitution, insertion, and/or addition of 1 to 26 bases in a base sequence of the polynucleotide (NC1), and encoding a protein having *Tobamovirus* resistance control activity;

(NC3) a polynucleotide consisting of a base sequence having at least 98% sequence identity to the base sequence of the polynucleotide (NC1), and encoding a protein having *Tobamovirus* resistance control activity;

(NC5) a polynucleotide encoding a protein consisting of an amino acid sequence of SEQ ID NO: 9;

(NC6) a polynucleotide encoding a protein consisting of an amino acid sequence obtained by deletion, substitution, insertion, and/or addition of 1 to 6 amino acids in the amino acid sequence of SEQ ID NO: 9, and having *Tobamovirus* resistance control activity; and (NC7) a polynucleotide encoding a protein consisting of an amino acid sequence having at least 98% sequence identity to the amino acid sequence of SEQ ID NO: 9, and having *Tobamovirus* resistance control activity, and the SITOM1d gene is a *Tobamovirus* resistance control gene comprising the following polynucleotide (ND):

(ND) any of the following polynucleotides (ND1) to (ND3) and (ND5) to (ND7):

(ND1) a polynucleotide consisting of a base sequence of SEQ ID NO: 10;

(ND2) a polynucleotide consisting of a base sequence obtained by deletion, substitution, insertion, and/or addition of 1 to 26 bases in a base sequence of the polynucleotide (ND1), and encoding a protein having *Tobamovirus* resistance control activity;

(ND3) a polynucleotide consisting of a base sequence having at least 98% sequence identity to the base sequence of the polynucleotide (ND1), and encoding a protein having *Tobamovirus* resistance control activity;

(ND5) a polynucleotide encoding a protein consisting of an amino acid sequence of SEQ ID NO: 11;

(ND6) a polynucleotide consisting of an amino acid sequence obtained by deletion, substitution, insertion, and/or addition of 1 to 6 amino acids in the amino acid sequence of SEQ ID NO: 11, and encoding a protein having *Tobamovirus* resistance control activity; and (ND7) a polynucleotide consisting of an amino acid sequence having at least 98% sequence identity to the amino acid sequence of SEQ ID NO: 11, and encoding a protein having *Tobamovirus* resistance control activity, the *Tobamovirus* is Tomato mosaic virus (ToMV), or Tomato brown rugose fruit virus (ToBRFV), and the loss of function for the SITOM1a gene, the SITOM1c gene, and the SITOM1d gene is caused by introducing deletion, substitution, insertion, and/or addition of nucleotides into said genes itself.

5. The method according to claim 1, wherein the *Tobamovirus* resistant tomato plant comprises the loss-of-function gene for a SITOM1a gene, the loss-of-function gene for a SITOM1c gene, and the loss-of-function gene for a SITOM1d gene in a homozygous form.

6. The method according to claim 1, wherein the *Tobamovirus* resistant tomato plant is a plant body or a part thereof.

7. The method according to claim 1, wherein the *Tobamovirus* resistant tomato plant is a seed.

8. The method according to claim 1, wherein the *Tobamovirus* is Tomato mosaic virus (ToMV).

9. The method according to claim 1, wherein the *Tobamovirus* is Tomato brown rugose fruit virus (ToBRFV).

10. The method according to claim 1, wherein the *Tobamovirus* resistant tomato plant comprises a loss-of-function for a *Solanum lycopersicum* TOM1b (SITOM1b) gene, wherein the SITOM1b gene is a *Tobamovirus* resistance control gene comprising the following polynucleotide (NB):

(NB) any of the following polynucleotides (NB1) to (NB3) and (NB5) to (NB7):

(NB1) a polynucleotide consisting of a base sequence of SEQ ID NO: 4 or 5;

(NB2) a polynucleotide consisting of a base sequence obtained by deletion, substitution, insertion, and/or addition of 1 to 26 bases in a base sequence of the polynucleotide (NB1), and encoding a protein having *Tobamovirus* resistance control activity;

(NB3) a polynucleotide consisting of a base sequence having at least 98% sequence identity to the base sequence of the polynucleotide (NB1), and encoding a protein having *Tobamovirus* resistance control activity;

(NB5) a polynucleotide encoding a protein consisting of an amino acid sequence of SEQ ID NO: 6;

(NB6) a polynucleotide encoding a protein consisting of an amino acid sequence obtained by deletion, substitution, insertion, and/or addition of 1 to 6 amino acids in the amino acid sequence of SEQ ID NO: 6, and encoding a protein having *Tobamovirus* resistance control activity; and (NB7) a polynucleotide encoding a protein consisting of an amino acid sequence having at least 98% sequence identity to the amino acid sequence of SEQ ID NO: 6, and encoding a protein having *Tobamovirus* resistance control activity, and the loss of function for the SITOM1b gene is caused by introducing deletion, substitution, insertion, and/or addition of nucleotides into said genes itself.

11. The method according to claim 10, wherein the *Tobamovirus* resistant tomato plant comprises the loss-of-function gene for a SITOM1b gene in a homozygous form.

12. The method according to claim 10, wherein the *Tobamovirus* resistant tomato plant comprises:

the loss-of-function gene for a SITOM1a gene, the loss-of-function gene for a SITOM1b gene, and the loss-of-function gene for a SITOM1c gene in a homozygous form, and the loss-of-function gene for a SITOM1d gene in a heterozygous form.

* * * * *